US012589122B2

(12) United States Patent
Nagler et al.

(10) Patent No.: US 12,589,122 B2
(45) Date of Patent: Mar. 31, 2026

(54) METHODS AND COMPOSITIONS FOR TREATING INFECTIOUS, AUTOIMMUNE, AND ALLERGIC DISEASE

(71) Applicants: The University of Chicago, Chicago, IL (US); ClostraBio, Chicago, IL (US)

(72) Inventors: Cathryn R. Nagler, Chicago, IL (US); Riyue Bao, Chicago, IL (US); Dionysios Antonopoulos, Chicago, IL (US); John W. Colson, Chicago, IL (US); Lauren Anders Hesser, Chicago, IL (US)

(73) Assignees: The University of Chicago, Chicago, IL (US); ClostraBio, Chicago, IL (US)

( * ) Notice: Subject to any disclaimer, the term of this patent is extended or adjusted under 35 U.S.C. 154(b) by 279 days.

(21) Appl. No.: 17/309,185

(22) PCT Filed: Nov. 5, 2019

(86) PCT No.: PCT/US2019/059865
    § 371 (c)(1),
    (2) Date: May 4, 2021

(87) PCT Pub. No.: WO2020/097077
    PCT Pub. Date: May 14, 2020

(65) Prior Publication Data
    US 2021/0386796 A1      Dec. 16, 2021

Related U.S. Application Data

(60) Provisional application No. 62/755,945, filed on Nov. 5, 2018.

(51) Int. Cl.
| | |
|---|---|
| A61K 35/741 | (2015.01) |
| A23L 33/135 | (2016.01) |
| A23L 33/21 | (2016.01) |
| A61K 45/06 | (2006.01) |
| A61P 37/02 | (2006.01) |

(52) U.S. Cl.
    CPC .......... A61K 35/741 (2013.01); A23L 33/135 (2016.08); A23L 33/21 (2016.08); A61K 45/06 (2013.01); A61P 37/02 (2018.01)

(58) Field of Classification Search
    CPC ..... A61K 35/741; A23L 33/135; A23L 33/21; A61P 37/02; A61P 17/00; A61P 37/08
    See application file for complete search history.

(56) References Cited

U.S. PATENT DOCUMENTS

| | | | |
|---|---|---|---|
| 10,369,176 B2 | 8/2019 | Goodman et al. | |
| 2007/0258953 A1 | 11/2007 | Duncan et al. | |
| 2008/0275141 A1 | 11/2008 | Whiteford | |
| 2014/0341921 A1 | 11/2014 | Honda et al. | |
| 2016/0271189 A1 * | 9/2016 | Cutcliffe .............. | A61K 9/0014 |
| 2016/0317653 A1 | 11/2016 | Cook et al. | |
| 2019/0282647 A1 * | 9/2019 | Öckerman .......... | A61K 31/455 |

FOREIGN PATENT DOCUMENTS

| | | | | |
|---|---|---|---|---|
| CN | 108676774 A | 10/2018 | | |
| JP | 2015 500792 | 1/2015 | | |
| JP | 2019-511563 | 4/2019 | | |
| WO | WO 2013/080561 | 6/2013 | | |
| WO | WO 2015/095241 | 6/2015 | | |
| WO | WO 2016/070151 | 5/2016 | | |
| WO | WO 2017/079450 | 5/2017 | | |
| WO | WO 2017/134240 | 8/2017 | | |
| WO | WO 2018/057914 | 3/2018 | | |
| WO | WO-2018057914 A1 * | 3/2018 | .......... | A23L 33/135 |
| WO | WO 2018/075886 | 4/2018 | | |
| WO | WO 2018/106844 | 6/2018 | | |
| WO | WO 2018/107365 | 6/2018 | | |
| WO | WO 2018/129249 | 7/2018 | | |
| WO | WO 2018/187272 | 10/2018 | | |
| WO | WO 2018/195067 | 10/2018 | | |
| WO | WO-2018195067 A1 * | 10/2018 | ............. | A61K 47/32 |
| WO | WO 2020/097077 | 5/2020 | | |
| WO | WO 2020/109646 | 6/2020 | | |

OTHER PUBLICATIONS

Chen et al. (Role of lactic acid bacteria on the yogurt flavour: A review, International Journal of Food Properties, 2017, vol. 20, No. S1, S316-S330). (Year: 2017).*
Barczynska et al. Prebiotic properties of potato starch dextrins, Postepy Hig Med Dosw (online), 2015; 69:1031-1041 (Year: 2015).*
Bui et al. *Anaerostipes rhamnosivorans* sp. nov., a human intestinal, butyrate-forming bacterium, International Journal of Systematic and Evolutionary Microbiology (2014), 64, 787-793 (Year: 2014).*
Inoue et al. (A preliminary study of gut dysbiosis in children with food allergy, Bioscience, Biotechnology, and Biochemistry, 2017 vol. 81, No. 12, 2396-2399). (Year: 2017).*
Li, "Modern Nutrition and Food Safety", 2nd Edition, Second Military Medical University Press, pp. 56, Feb. 28, 2013 with English Translation.
Bashir et al., "Toll-like receptor 4 signaling by intestinal microbes influences susceptibility to food allergy" *J Immunol* 2004, 172, 6978-6987.

(Continued)

*Primary Examiner* — Louise W Humphrey
*Assistant Examiner* — Alexander M Duryee
(74) *Attorney, Agent, or Firm* — Norton Rose Fulbright US LLP

(57)          ABSTRACT

Provided herein are methods and compositions for treating food allergies, infections, autoimmune conditions, and other allergic conditions. Also provided are methods for treating an infectious, autoimmune, or allergic disease in a subject comprising administering a composition comprising bacterium *Anaerostipes caccae* to the subject. Further aspects relate to a method for treating a food allergy or for reducing an allergic response to an allergen or for treating or preventing an anaphylactic response in a subject comprising administering a composition comprising bacterium *Anaerostipes caccae* and a prebiotic to the subject.

13 Claims, 25 Drawing Sheets

Specification includes a Sequence Listing.

(56) References Cited

OTHER PUBLICATIONS

Berni Canani et al., "Lactobacillus rhamnosus GG-supplemented formula expands butyrate-producing bacterial strains in food allergic infants" *The ISME Journal* 2016, 10, 742-750.

Bunyavanich et al., "Early-life gut microbiome composition and milk allergy resolution" *J Allergy Clin Immunol* 2016, 138, 1122-1130.

Cahenzli et al., "Intestinal microbial diversity during early-life colonization shapes long-term IgE levels" *Cell Host Microbe* 2013, 14, 559-570.

Dominguez-Bello et al. "Delivery mode shapes the acquisition and structure of the initial microbiota across multiple body habitats in newborns" *Proc Natl Acad Sci U S A* 2010, 107, 11971-11975.

Duncan et al., "Lactate-utilizing bacteria, isolated from human feces, that produce butyrate as a major fermentation product" *Appl Environ Microbiol* 2004, 70, 5810-5817.

International Search Report and Written Opinion issued in Corresponding PCT Application No. PCT/US2019/059865, dated Feb. 20, 2020.

Ivory et al., "Oral delivery of Lactobacillus casei Shirota modifies allergen-induced immune responses in allergic rhinitis" *Clinical and Experimental Allergy* 2008, 38, 1282-1289.

Mueller et al., "The infant microbiome development: mom matters" *Trends Mol Med* 2015, 21, 109-117.

Pascal et al., "Microbiome and Allergic Diseases" *Frontiers in Immunology* 2018, 9(1584), 1-9.

Planer et al., "Development of the gut microbiota and mucosal IgA responses in twins and gnotobiotic mice" *Nature* 2016, 534, 263-266.

Plunkett et al., "The Influence of the Microbiome on Allergic Sensitization to Food" *J Immunol* 2017, 198, 581-589.

Schwiertz et al., "*Anaerostipes caccae* gen. nov., sp. nov., a new saccharolytic, acetate-utilising, butyrate-producing bacterium from human faeces" *Systematic and applied microbiology* 2002, 25, 46-51.

Stefka et al., "Commensal bacteria protect against food allergen sensitization" *Proc Natl Acad Sci U S A* 2014, 111, 13145-13150.

Wesemann et al., "The Microbiome, Timing, and Barrier Function in the Context of Allergic Disease" *Immunity* 2016, 44, 728-738.

Extended European Search Report issued in Corresponding European Application No. 19882127.4, dated Jul. 22, 2022.

Van den Abbeele et al., "Arabinoxylans and inulin differentially modulate the mucosal and luminal gut microbiota and mucin-degradation in humanized rats" *Environmental Microbiology* 2011, 13(10), 2667-2680.

English translation of Office Communication issued in Chinese Patent Application No. 201980087923.6, dated Aug. 9, 2023.

English translation of Office Communication issued in Japanese Patent Application No. 2021-524290, dated Sep. 4, 2023.

Sato et al., "Isolation of lactate-utilizing butyrate-producing bacteria from human feces and in vivo administration of Anaerostipes caccae strain L2 and galacto-oligosaccharides in a rat model," FEMS Microbiol Ecol., 66(3):528-536, 2008.

Feehley et al., "Healthy infants harbor intestinal bacteria that protect against food allergy," Nat Med. 25(3):448-53, 2019.

PCT International Search Report and Written Opinion issued in corresponding International Application No. PCT/US2021/070926 mailed Dec. 7, 2021.

Stefka et al., "Commensal bacteria protect against food allergen sensitization," Proc Natl. Acad. Sci. U.S.A., 111(36):13145-50, 2014.

Belengeur et al., "Two Routes of Metabolic Cross-Feeding between Bifidobacterium adolescentis and Butyrate-Producing Anaerobes from the Human Gut," Applied and Environmental Microbiology, 72(5):3593-3599, 2006.

English translation of Office Communication issued in Japanese Patent Application No. 2021-524290, dated Apr. 15, 2024.

People's Medical Publishing House, "Lecture Series on Antibiotics", Institute of Antibiotics, Chinese Academy of Medical Sciences, Oct. 31, 1959, p. 108 (with English Translation).

Chia et al., "Bacteroides thetaiotaomicron Fosters the Growth of Butyrate-Producing Anaerostipes caccae in the Presence of Lactose and Total Human Milk Carbohydrates," Microorganisms, Oct. 1, 2020, 8(10):1-13.

Li, et al., "Anaerobic Bacteria," Anhui Science and Technology Publishing House, Dec. 31, 1983, p. 165 (with English Translation).

Office Communication issued in Chinese Patent Application No. 201980087923.6, dated Jun. 5, 2024 (with English Translation).

Bircher et al., "Effect of cryopreservation and lyophilization on viability and growth of strict anaerobic human gut microbes," Microbial Biotechnology, 11:721-733, 2018.

Falony et al., "Cross-feeding between Bifidobacterium longum BB536 and acetate-converting, butyrate-producing colon bacteria during growth on oligofructose," Applied and Environmental Microbiology, 72:7835-7841, 2006.

Office Communication issued in Australian Patent Application No. 2019374773, dated Aug. 28, 2025.

Ose et al., "The ability of human intestinal anaerobes to metabolize different oligosaccharides: Novel means for microbiota modulation?" Anaerobe, 51:110-119, 2018.

* cited by examiner

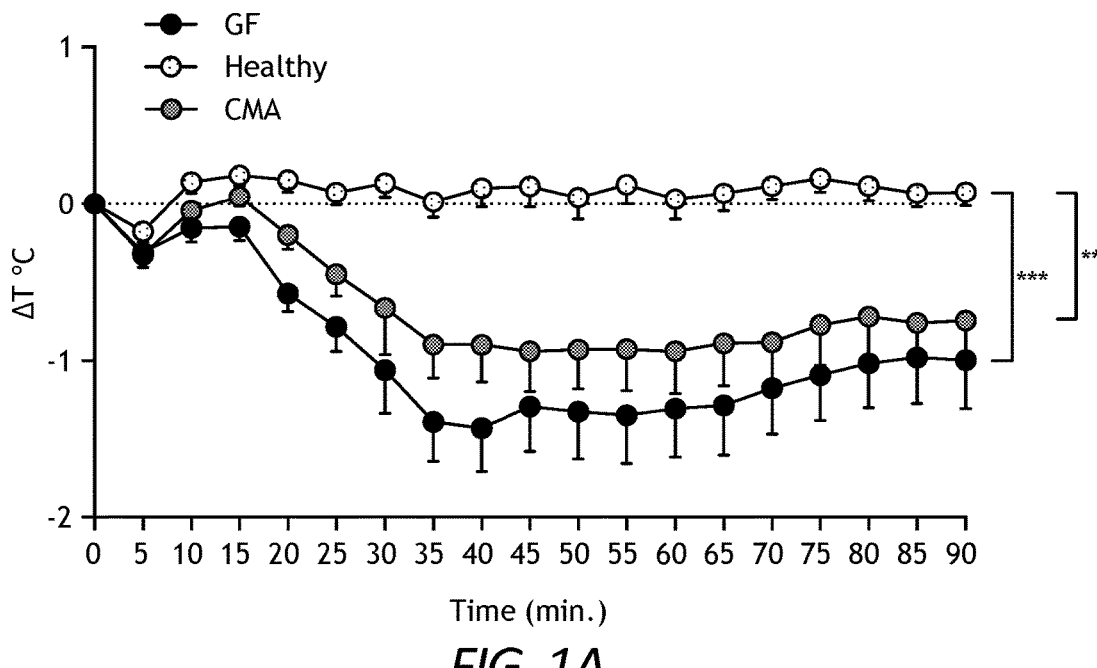
*FIG. 1A*
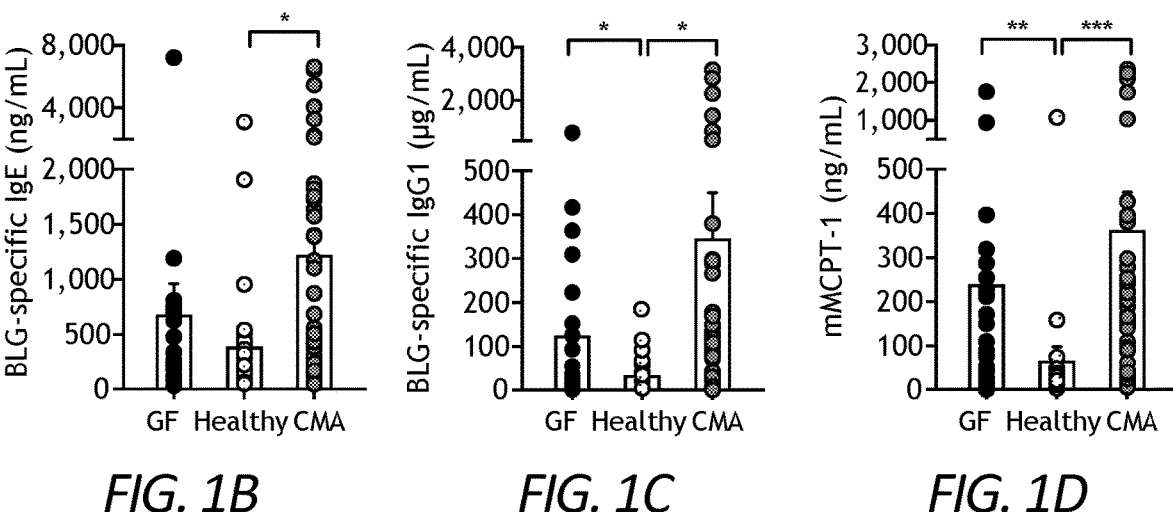
*FIG. 1B*         *FIG. 1C*         *FIG. 1D*

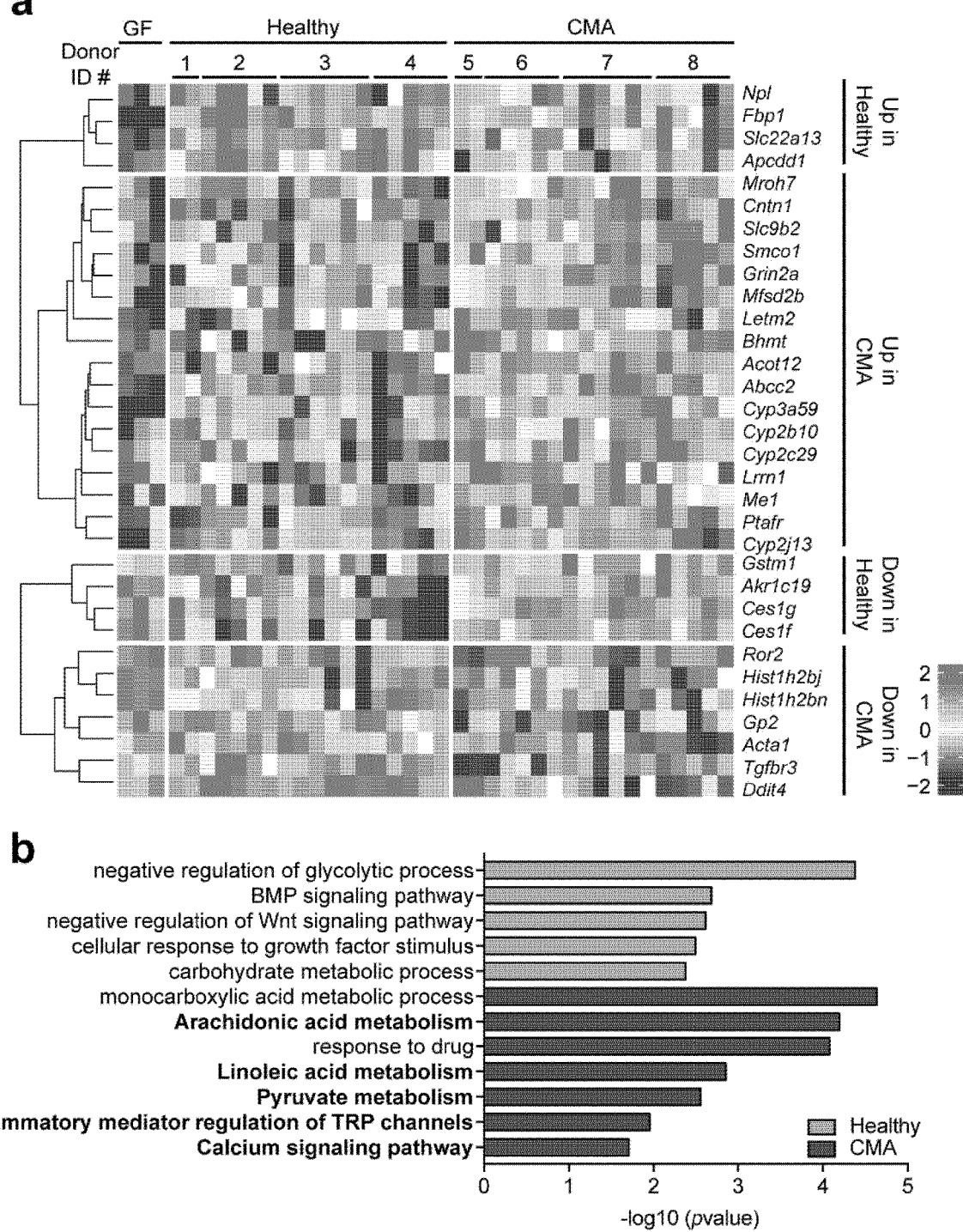
FIG. 3A-B

*FIG. 4C*
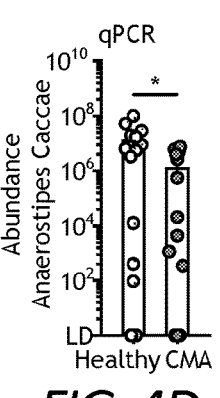
*FIG. 4D*
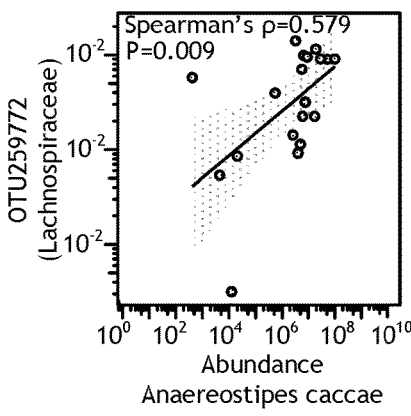
*FIG. 4E*
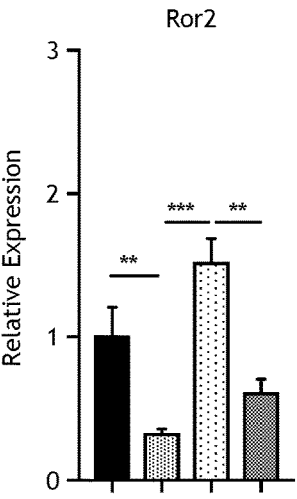
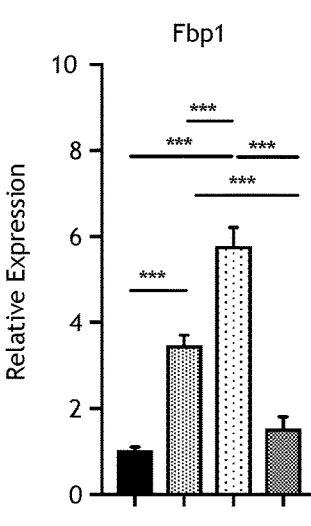
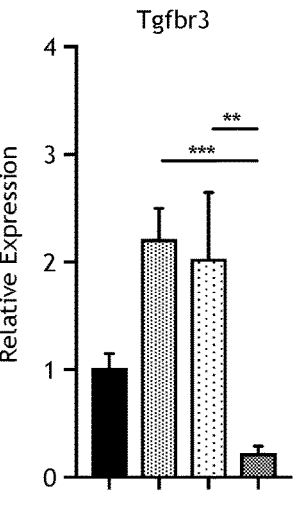
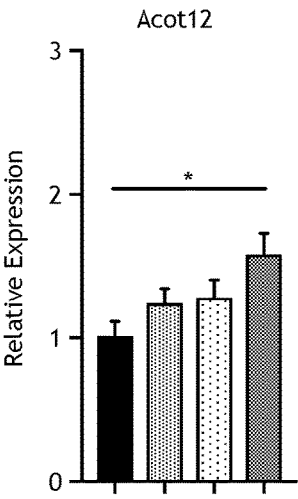
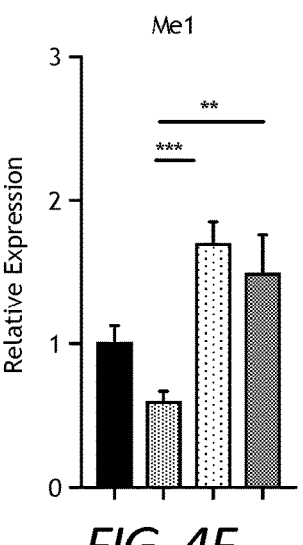
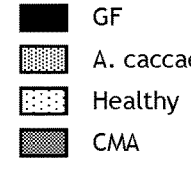
*FIG. 4F*

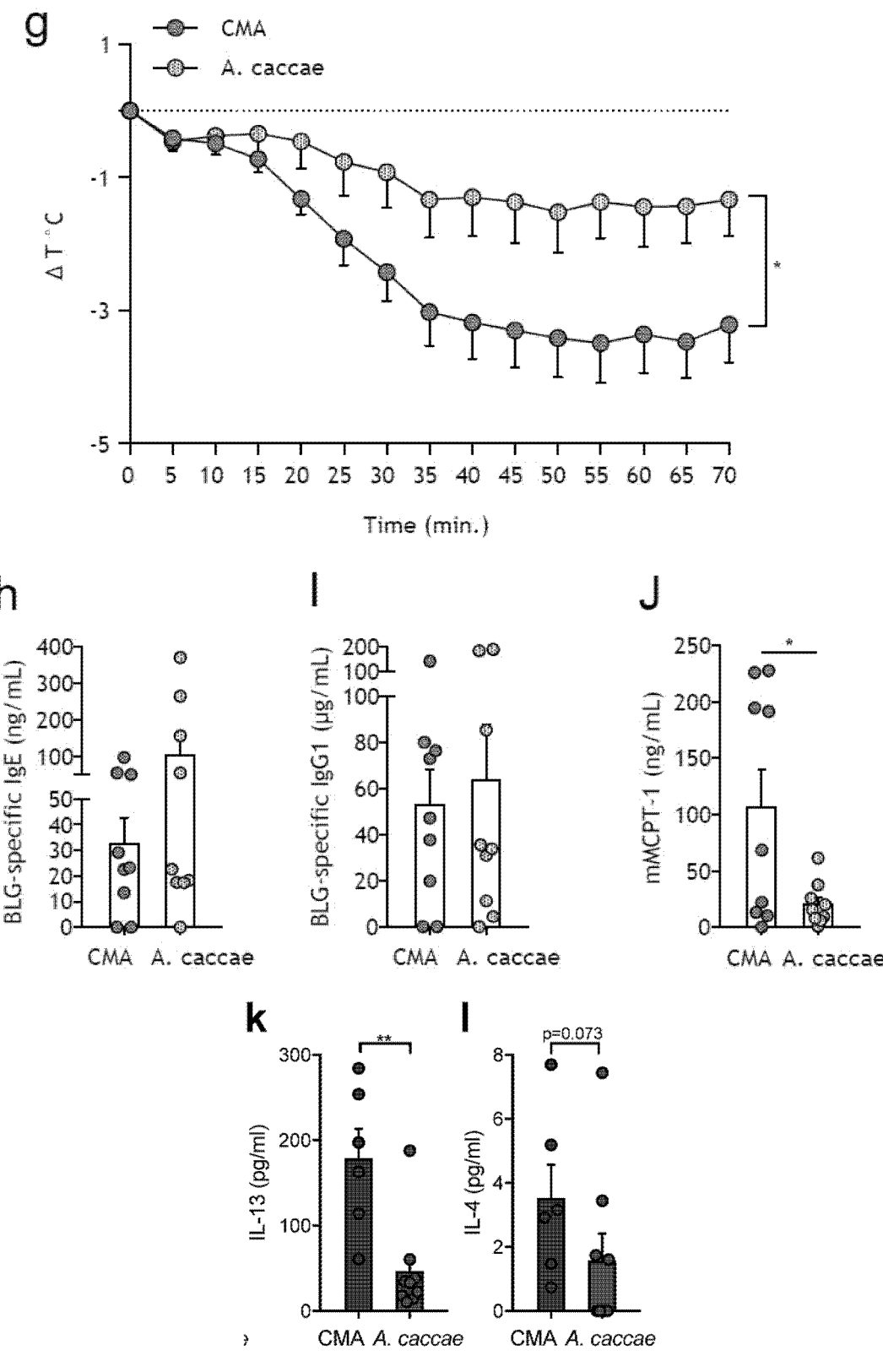
FIG. 4G-L

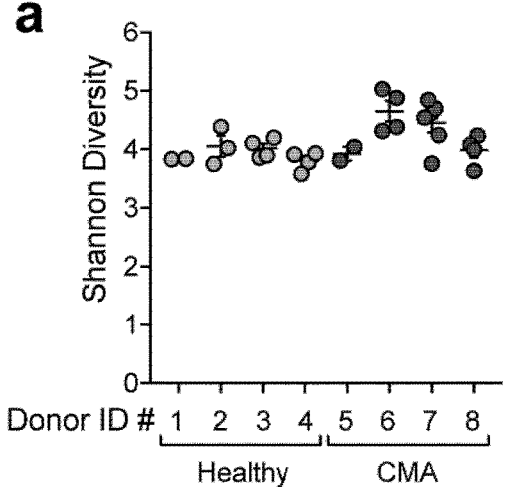
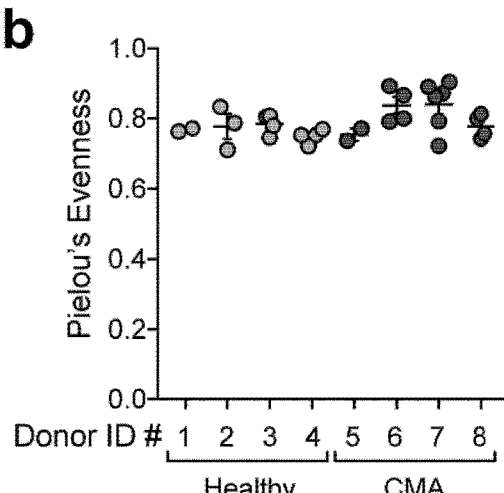
FIG. 7A-B

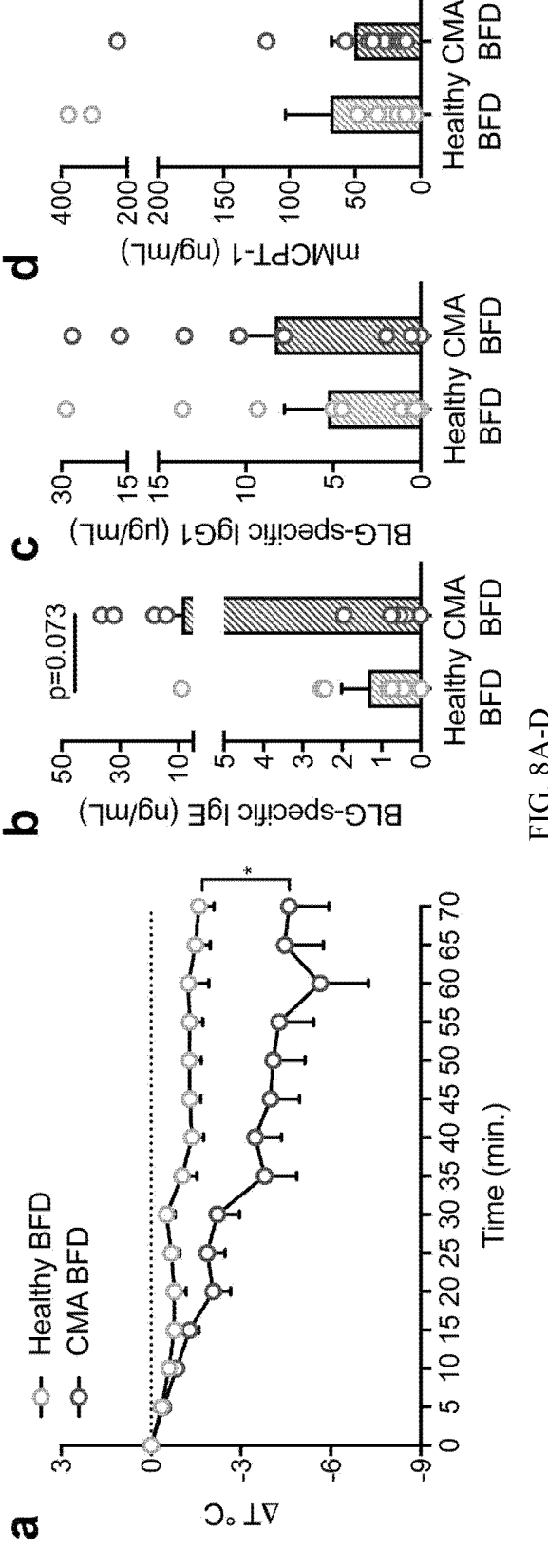
FIG. 8A-D

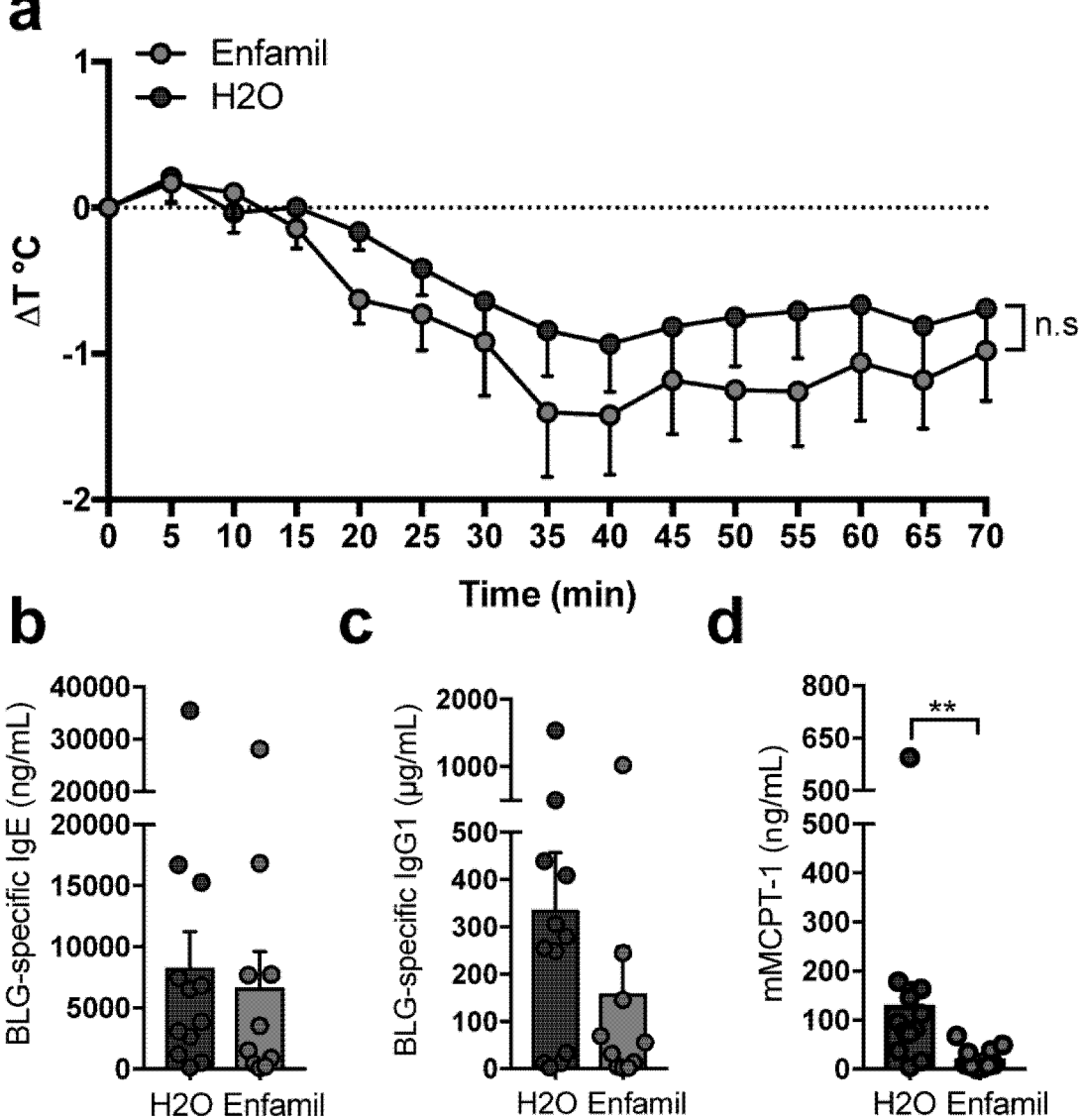
FIG. 9A-D

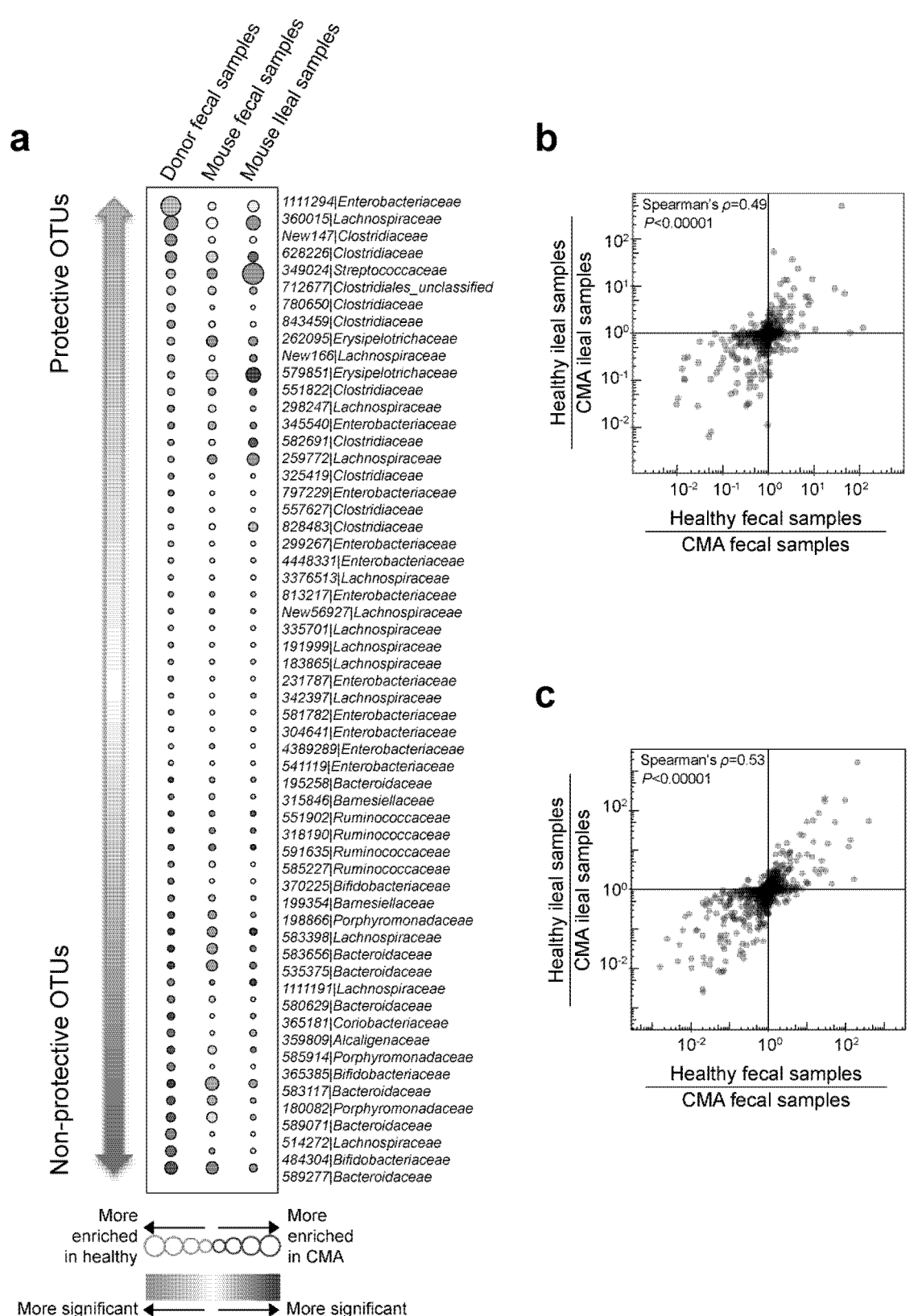
FIG. 12A-C

FIG. 13A-C

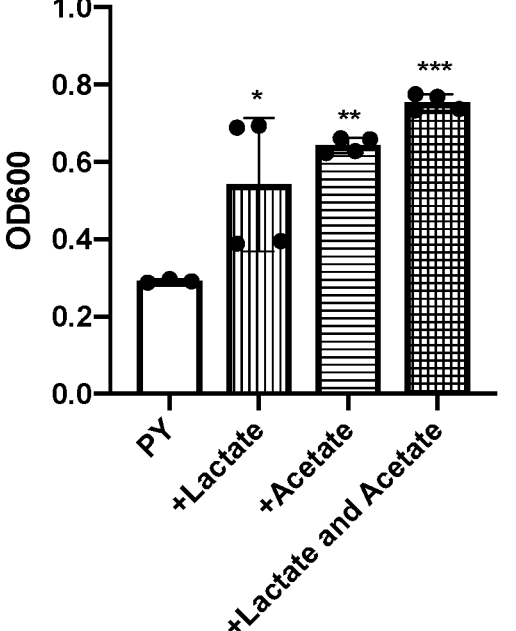
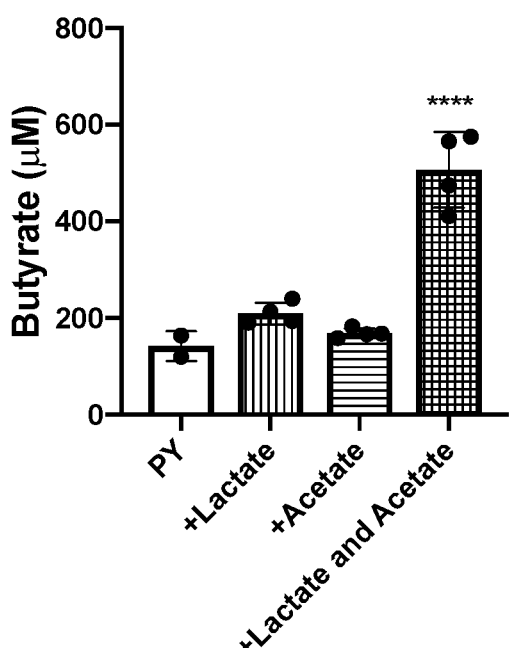
FIG. 18

METHODS AND COMPOSITIONS FOR TREATING INFECTIOUS, AUTOIMMUNE, AND ALLERGIC DISEASE

CROSS-REFERENCE TO RELATED APPLICATIONS

This application is a national phase application under 35 U.S.C. § 371 of International Application No. PCT/US2019/059865 filed Nov. 5, 2019, which claims the benefit of priority of U.S. Provisional Patent Application No. 62/755,945 filed Nov. 5, 2018, all of which are hereby incorporated by reference in their entirety.

BACKGROUND OF THE INVENTION

1. Field of the Invention

This invention relates to the field of molecular biology and medicine.

2. Background

A marked generational increase in disease prevalence in Westernized societies has made food allergy a major public health concern (1, 2). One hypothesis for this rapid rise in incidence proposes that recent lifestyle factors, including frequent use of antibiotics, changes in diet, and higher rates of Caesarean birth and formula feeding, have altered the composition of the intestinal commensal microbiota, increasing susceptibility to allergic diseases. Host-microbiota interactions are essential for establishing appropriate immune homeostasis and perturbations of naturally-selected bacterial populations, often referred to as dysbiosis, have been linked to many different pathologies; several studies suggest that early life dysbiosis may be particularly detrimental (3, 4).

There is a need in the art for compositions that modify the microbiome for the effective treatment of allergies and other related conditions.

SUMMARY OF THE INVENTION

The current disclosure fulfills the need in the art by providing methods and compositions for treating food allergies, infections, autoimmune conditions, and other atopic conditions. Accordingly, the current disclosure relates to a method for treating an infectious, autoimmune, or allergic disease in a subject comprising administering a composition comprising bacterium *Anaerostipes caccae* to the subject. Further aspects relate to a method for treating a food allergy or for reducing an allergic response to an allergen or for treating or preventing an anaphylactic response in a subject comprising administering a composition comprising bacterium *Anaerostipes caccae* and a prebiotic to the subject. In some aspects, the method relates to treating a food allergy in a subject comprising administering a composition comprising bacterium *Anaerostipes caccae* and a prebiotic to the subject. In some aspects, the method relates to treating a subject at risk for having or for developing a food allergy or anaphylactic response comprising administering a composition comprising bacterium *Anaerostipes caccae* and a prebiotic to the subject. For example, the subject may be at risk due to having a family history of a food allergy or a genetic pre-disposition to a food allergy or at risk of anaphylactic response due to accidental exposure to an allergen. In some aspects, the subject is one that has a microbial profile that is unfavorable or an indication that a food allergy may be present or may develop in the subject. In other aspects, the methods relate to reducing an allergic response to an allergen in a subject comprising administering a composition comprising bacterium *Anaerostipes caccae* and a prebiotic to the subject. In further aspects, the methods relate to treating or preventing an anaphylactic response in a subject comprising administering a composition comprising bacterium *Anaerostipes caccae* and a prebiotic to the subject. Yet further aspects relate to a method for treating an atopic disease in a subject in need thereof, the method comprising administering a composition comprising bacterium *Anaerostipes caccae* and a prebiotic to the subject. In some aspects, the method is for treating atopy in a subject by administration of a composition comprising bacterium *Anaerostipes caccae* and a prebiotic to the subject.

Further aspects relate to a method for diagnosing a subject with a food allergy, the method comprising determining the ratio of protective/non-protective operational taxonomic units (OTUs); wherein the subject is diagnosed with a food allergy when the ratio is less than 3. Further aspects relate to a method for diagnosing a subject with an allergic condition, infection, or autoimmune condition, the method comprising determining the ratio of protective/non-protective operational taxonomic units (OTUs); wherein the subject is diagnosed with an allergic condition, infection, or autoimmune condition when the ratio is less than 3. In some embodiments, the ratio of protective/non-protective operational taxonomic units (OTUs) is less than, greater than, or about 6, 5.5, 5, 4.5, 4, 3.5, 3, 2.5, 2, 1.5, 1, or 0.5 (or any derivable range therein).

Further aspects of the disclosure relate to a composition comprising bacterium *Anaerostipes caccae* and a prebiotic. Further aspects relate to a tablet, capsule, or powder comprising the composition of the disclosure.

Described below are specific embodiments that may be used with any of the aspects described above and herein.

In some embodiments of the above-disclosed aspects, the methods relate to treating an atopic disease. In some embodiments, the atopic disease comprises eczema, atopic dermatitis, asthma, or allergic rhinitis.

In some embodiments, the method is for reducing an allergic response to an allergen in a subject. In some embodiments, the subject has been determined to exhibit an allergic response to the allergen. Allergic responses can take multiple forms and have multiple levels of severity or intensity. These allergic responses can vary from person to person, but they also vary over time for any individual. Systems for scoring severity or intensity of response are known and described in the art. For example, a scoring system is described in Sampson et al, *J. Allergy Clin. Immunol.* Vol 130 (6) p. 1260 (2012), which is incorporated by reference for all purposes. It should be understood that the phrase reducing an allergic response means reducing the severity or intensity of an allergic response as measured by one of the scoring systems known in the art. In some embodiments, reducing an allergic response relates to a statistically significant reduction of the allergic response. In some embodiments, the average severity or intensity of allergic response over a population of multiple people or animals is reduced. In some embodiments, allergic response can mean response to any atopic disease including eczema, asthma, and allergic rhinitis in addition to food allergy. In some embodiments, the allergic response is reduced by at least a grade, as scored according to the scoring system described in Sampson et al. For example, in certain embodiments, the allergic response is reduced from a grade 3 to a grade 2. In some embodiments, the allergic response is reduced from a grade 2 to a grade 1. In some embodiments, the allergic response is reduced from a grade 1 to a grade 0. In some embodiments, the allergic response is reduced from a grade 3 to a grade 1. In some embodiments, the allergic response is reduced from a grade 3 to a grade 0. In some embodiments, the allergic response is reduced from a grade 2 to a grade 0.

The term "prebiotic" refers to an oligosaccharide or polysaccharide with a degree of polymerization of two or more that is not susceptible to digestion or degradation prior to entering the upper gastrointestinal tract, such as the small intestine, and is fermentable or digestible by microbes or other processes within the colon in which the fermented or digested oligosaccharides or their byproducts of digestion alter the microbiome or provide benefit to human or animal In some embodiments, the methods are for treating an anaphylactic response. In some embodiments, the anaphylactic response is from a food allergy. In some embodiments, the anaphylactic response is from a drug allergy. In some embodiments, the anaphylactic response is from an insect bite.

In some embodiments, the short-chain oligosaccharide has a polymerization degree of at least, at most, or about 1, 2, 3, 4, 5, 6, 7, 8, 9, 10, 11, 12, 13, 14, 15, 16, 17, 18, 19, 20, 21, 22, 23, 24, 25, 30, 40, 50, 60, 65, 70, 75. In some embodiments, the prebiotic comprises galactooligosaccharide (GOS). GOS can often be found in abundance in human breast milk which contains a significant quantity of lactose and may be degraded by beta-galactosideases. Specific examples of GOS include stachyose, raffinose, verbascose, β(1-4)-galactosyl-lactose (4'-galacto-oligosaccharide) and β(1-6)-galactosyl-lactose (6'-galacto-oligosaccharide) and lactulose. In some embodiments, the prebiotic comprises fructan (including short-chain fructooligosaccharides (scFOS), fructo-oligosaccharides (FOS), and inulin), galactans, glucans, and other oligosaccharides. Examples of such include short-chain FOS (shorter chains of fructose below, with degree of polymerization from 2-4); fructooligosaccharides (with degree of polymerization of 4-20); inulin (with degree of polymerization >20) or phlein; soybeanoligosaccharide (SOS); galactooligosacchararide (GOS); iso-maltooligosaccharide (IMOS) (derived from starches in wheat, barley, corn, oats, tapioca, rice, potato) including isomaltose, isomaltotriose, and panose; soybeanoligosaccharides (SOS) (from soybean) including raffinose and tetrasaccharide stachyose; xylooligosaccharides (XOS) including xylan, xylobiose, xylothiose, and xylotetraose (derived from starches found in bamboo shoots, fruits, vegetables, milk, and honey); pecticoligosaccharides (POS) including pectin; chitooligosaccharides including chitin; lactulose; beta-glucans (from cereal grains, such as oat, barley, wheat, and rye); and Type III resistant starch, which includes resistant starch that is formed when starch-containing foods are cooled (ex. pasta, potatoes, and rice). Further examples include polyols such as isomalt, maltitol, mannitol, sorbitol, xylitol, lactitol, erythritol, and polyglycitol. Sources of polyols include apples, apricots, avocados, blackberries, cherries, lychees, nectarines, peaches, pears, plums, prunes, watermelon, cauliflower, and mushrooms. Even further examples include non-fructans such as dextrins, including maltodextrins, cyclodextrins, and pirodextrins (derived from potato and maize starch), wheat dextrin, high-amylose corn-starch (and maizestarch), amylose, and amylopectin. In some embodiments, the prebiotic comprises one or more of wherein the prebiotic comprises one or more of galactooligosacchararide, lactulose, lactitol, erythritol, isomalt, polyglycitol, acetate and lactate. In some embodiments, the prebiotic comprises one or more of galactooligosaccharide, lactulose, lactate, acetate, and lactitol.

Also included are derivatives and processed forms of the compounds described herein. Derivatives or processed forms may be modified to alter the fermentation properties of the prebiotic, for example, by making the prebiotic more readily digestible, more specific to a certain type of bacterium, or to increase yield of fermentation products, such as short-chain fatty acids (SCFAs) and/or other metabolites. Also included are foods and food derivatives known to contain quantities of these compounds and/or which are capable of having a prebiotic effect. These foods may be processed to isolate their starches, or may be administered without isolation of their starches, e.g. by grinding the food whole for consumption. Examples of such foods include: onion, artichoke, garlic, wheat, banana, asparagus, chicory, leek, tomato, bamboo shoots, fruits, vegetables, milk, honey, wheat, rye, barley, corn, oats, tapioca, rice, and potato.

The term "prebiotic derivative" refers to modified forms of the prebiotic made prior to consumption to increase fermentation properties, digestibility, or increase fermentation by products such as short-chain fatty acids and other metabolites.

In some embodiments, the prebiotic comprises one or both of digestible and non-digestible oligosaccharides. In some embodiments, the prebiotic comprises at least 6 grams of non-digestible oligosaccharides. In some embodiments, the prebiotic comprises at least, at most, or about 1, 2, 3, 4, 5, 6, 7, 8, 9, 10, 11, 12, 13, 14, 15, 16, 17, 18, 19, 20, 21, 22, 23, 24, 25, 30, or 40 grams (or any derivable range therein) of digestible and/or non-digestible oligosaccharides. The term "non-digestible oligosaccharides" as used herein refers to the part of a plant that is indigestible to the animal. The non-digestible oligosaccharides may be water-soluble (can be dissolved in water) or water-insoluble (does not dissolve in water). Specific examples of suitable non-digestible oligosaccharides useful in the methods and compositions of the disclosure include one or more of inulin (from chicory or agave), flax fiber, soy fiber, oat fiber, corn fiber, guar gum, gum Arabic, Larch bark, bean gum, gum acacia, pumpkin fiber, chia fiber, and combinations thereof.

In some embodiments, the oligosaccharide comprises a modified oligosaccharide. In some embodiments, the modified oligosaccharide comprises an *A. caccae* fermentable butyrate-releasing oligosaccharide. Butyrate-releasing means the generation of the metabolite butyrate as a by-product of fermentation. In some embodiments, the oligosaccharide is one that increases the concentration, mass or amount of lactate in the gastrointestinal tract following fermentation or digestion. Examples include wheat, rye, corn/maize, oats, rice, and potato. In some embodiments, the *A. caccae* fermentable butyrate-releasing oligosaccharide comprises a compound capable of being fermented by *A. caccae* into butyrate.

In some embodiments, the method further comprises administration of a butyrate carrying compound. In some embodiments, the butyrate carrying compound comprises pHPMA-b-pBMA, which is further described in WO 2018/195067. In some embodiments, the butyrate carrying compound comprises one that is disclosed in WO 2018/195067, which is incorporated by reference. In some embodiments, the butyrate carrying compound is administered by intra-gastric gavage.

In some embodiments, $1\times10^6$ to $1\times10^{15}$ cells or CFU of *A. caccae* is administered to the subject. In some embodiments, at least, at most, or about $1\times10^6$, $1\times10^7$, $1\times10^8$, $1\times10^9$,

5

$1 \times 10^{10}$, $1 \times 10^{11}$, $1 \times 10^{12}$, $1 \times 10^{13}$, $1 \times 10^{14}$, or $1 \times 10^{15}$ (or any derivable range therein) cells or CFU of *A. caccae* is administered.

In some embodiments, the *A. caccae*, the prebiotic, and/or butyrate carrying compound are administered simultaneously. In some embodiments, the *A. caccae* is administered at least 1 hour before the prebiotic and/or butyrate carrying compound. In some embodiments, the *A. caccae* and/or butyrate carrying compound is administered at least 1, 2, 3, 4, 5, 6, 7, 8, 9, 10, 12, or 18 hours or 1, 2, 3, 4, 5, or 6 days, or 1, 2, 3, 4, 5, 6, 7, or 8 weeks (or any range derivable therein) before or after the prebiotic and/or butyrate carrying compound. In some embodiments, at least 10 grams of prebiotic is administered to the subject. In some embodiments, at least, at most, or about 1, 2, 3, 4, 5, 6, 7, 8, 9, 10, 11, 12, 13, 14, 15, 16, 17, 18, 19, 20, 21, 22, 23, 24, 25, 30, 40, or 50 grams (or any derivable range therein) of prebiotic is administered to the subject. In some embodiments, the ratio of the colony forming units of *A. caccae* to grams of prebiotic and/or butyrate carrying compound is 1000:1-10000:1. In some embodiments, the ratio is at least, at most, or about 1:1, 2:1, 4:1, 5:1, 8:1, 10:1, 20:1, 40:1, 50:1, 80:1, 100:1, 150:1, 200:1, 250:1, 300:1, 400:1, 500:1, 1000:1, 1500:1, 2000:1, 2500:1, 3000:1, 3500:1, 4000:1, 4500:1, 5000:1, 7500:1, 10000:1, 1:2, 1:4, 1:5, 1:8, 1:10, 1:20, 1:40, 1:50, 1:80, 1:100, 1:150, 1:200, 1:250, 1:300, 1:400, 1:500, 1:1000, 1:1500, 1:2000, 1:2500, 1:3000, 1:3500, 1:4000, 1:4500, 1:5000, 1:7500, or 1:10000 (or any derivable range therein). In some embodiments the butyrate carrying compound is administered after the prebiotic. In some embodiments, the butyrate carrying compound and the prebiotic are in the same composition. In some embodiments, the butyrate carrying compound is administered immediately after or less than 5, 10, 20, 30, or 60 minutes (or any derivable range therein) after administration of the prebiotic.

In some embodiments, the food allergy comprises a cow's milk allergy. In some embodiments, the food allergy comprises a peanut or egg allergy. In some embodiments, the subject has been diagnosed with a food allergy, cow's milk allergy, peanut allergy, egg allergy, soy allergy, wheat/gluten allergy, shellfish allergy, sesame allergy, tree nut (pistachio, cashew, walnut, almond, hazelnut, macadamia nut) allergy, allergic condition, autoimmune disease, or infection. In some embodiments, the subject has previously been treated for a food allergy, allergic condition, autoimmune disease, or infection. In some embodiments, the subject has been determined to be resistant to the previous treatment. In some embodiments the subject has not been diagnosed with a food allergy, allergic condition, autoimmune disease, or infection and/or has not exhibited symptoms of a food allergy, allergic condition, autoimmune disease, or infection.

In some embodiments, the subject is a human. In some embodiments, the subject is a newborn, less than one year old, less than five years old, less than twelve years old or less than eighteen years old. In some embodiments, the subject is less than 20, 19, 18, 17, 16, 15, 14, 13, 12, 11, 10, 9, 8, 7, 6, 5, 4, 3, 2, or 1 years or 11, 10, 9, 8, 7, 6, 5, 4, 3, 2, or 1 months, or, 14, 13, 12, 11, 10, 9, 8, 7, 6, 5, 4, 3, 2, or 1 days old (or any derivable range therein). In specific embodiments, the patient is a pediatric patient—i.e., under 18 years of age. In other embodiments, the patient is an adult patient.

In some embodiments, the *A. caccae* comprises a live bacterial product. In some embodiments, the bacteria are lyophilized or freeze-dried. In some embodiments, the *A. caccae* and/or prebiotic are administered orally. In some embodiments, the *A. caccae* and/or prebiotic are administered in a tablet or capsule. In some embodiments, the *A.*

6

*caccae* and/or prebiotic are administered by a route of administrated described herein.

The term "food" or "food derivatives" refers to cooked or uncooked edible items comprising prebiotics found in the whole item or processed to further isolate the prebiotic.

In some embodiments, the method further comprises administration of a lactate-containing formula or food. In some embodiments, the food is apples, apricots, avocados, blackberries, cherries, lychees, nectarines, peaches, pears, plums, prunes, watermelon, cauliflower, and mushrooms, onion, artichoke, garlic, wheat, banana, asparagus, chicory, leek, tomato, bamboo shoots, fruits, vegetables, milk, honey, wheat, rye, barley, corn or maize, oats, tapioca, rice, and potato.

In some embodiments, the subject is determined to have a ratio of protective/non-protective operational taxonomic units (OTUs) of less than 3. In some embodiments, the ratio of protective/non-protective operational taxonomic units (OTUs) is less than, greater than, or about 6, 5.5, 5, 4.5, 4, 3.5, 3, 2.5, 2, 1.5, 1, or 0.5 (or any derivable range therein).

In some embodiments, the protective OTUs comprise one or more OTUs selected from 1111294, 360015, New Reference OTU147, 628226, 349024, 712677, 780650, 843459, 262095, New Reference OTU166, 579851, 551822, 298247, 345540, 582691, 259772, 325419, 797229, 557627, 828483, 299267, 4448331, 3376513, 813217, New.CleanUp.Reference OTU56927, 335701, 191999, 183865, 231787, 342397, 581782, 304641, 4389289, or 541119 as described in Supplementary Table 3. In some embodiments, the non-protective OTUs comprise one or more OTUs selected from 195258, 315846, 551902, 318190, 591635, 585227, 370225, 199354, 198866, 583398, 583656, 535375, 1111191, 580629, 365181, 359809, 585914, 365385, 583117, 180082, 589071, 514272, 484304, or 589277 as described in Supplementary Table 3.

In some embodiments, the composition further comprises a pharmaceutical excipient. In some embodiments, the composition is formulated for oral administration.

Throughout this application, the term "about" is used to indicate that a value includes the inherent variation of error for the measurement or quantitation method.

The use of the word "a" or "an" when used in conjunction with the term "comprising" may mean "one," but it is also consistent with the meaning of "one or more," "at least one," and "one or more than one."

The phrase "and/or" means "and" or "or". To illustrate, A, B, and/or C includes: A alone, B alone, C alone, a combination of A and B, a combination of A and C, a combination of B and C, or a combination of A, B, and C. In other words, "and/or" operates as an inclusive or.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. Compositions and methods "consisting essentially of" any of the ingredients or steps disclosed limits the scope of the claim to the specified materials or steps which do not materially affect the basic and novel characteristic of the claimed invention.

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-D. Transfer of healthy, but not CMA, infants' microbiota protects against an allergic response to food. (a) Change in core body temperature at indicated time points following first challenge with β lactoglobulin (BLG) in germ-free mice and in mice colonized with feces from each of 8 donors (4 healthy, 4 CMA, see Supplementary Table 1) that had been sensitized with BLG plus cholera toxin (CT); n=42 CMA, 31 healthy and 24 GF mice with 4-12 mice for each of the 8 donors, collected from two independent experiments. (b) Serum BLG-specific IgE, (c) BLG-specific IgG1 and (d) mMCPT-1 from mice in a. For a, circles represent mean, error bars represent s.e.m. For b-d, circles represent individual mice, bars represent mean+s.e.m. Linear mixed-effect models were used to compare groups in a-d with the Benjamini-Hochberg FDR (BH-FDR) method for multiple testing correction. *P<0.05, P<0.01 *P<0.001.

FIG. 3A-B. Unique ileal transcriptome signatures distinguish healthy- and CMA-colonized mice. (a) Heatmap of 32 differentially expressed genes (DEGs) in ileal IECs isolated from GF (n=3), healthy-colonized (n=18) or CMA-colonized (n=18) mice pooled from at least 2 independent experiments at seven days post-colonization (see Supplementary Table 4). Each column depicts an individual mouse colonized with donor feces as indicated. Four types of gene expression changes are shown: (1) up in healthy: genes that are up-regulated in healthy mice relative to both CMA and GF; (2) up in CMA: genes that are up-regulated in CMA mice relative to both healthy and GF; (3) down in healthy: genes that are down-regulated in healthy mice relative to both CMA and GF; and (4) down in CMA: genes that are down-regulated in CMA mice relative to healthy and GF. (b) Gene Ontology (GO) terms and KEGG pathways (bold) significantly enriched in DEGs from a that are associated with healthy-colonized (orange) or CMA-colonized (blue) mice. Hypergeometric testing was used in b with the Benjamini-Hochberg FDR (BH-FDR) method for multiple testing correction (see Methods).

FIG. 4A-L. Correlation of ileal OTUs with DEGs in the ileum of healthy-colonized mice identifies a Clostridial species, A. caccae, that protects against an allergic response to food. (a) Heatmap showing Spearman's rank correlation coefficient between relative abundance of ileal OTUs (row) and expression of DEGs (column) from CMA vs healthy mouse ileal IEC samples (see FIG. 3a and Methods). (b) Spearman's correlation between abundance of OTU259772 (Lachnospiraceae) from the ileal 16S dataset (see Supplementary Table 5) and RNA-Seq expression in ileal IECs of Ror2, Fbp1, Tgfbr3, Acot12 and Me1. Circles represent individual mice and shaded bands indicate 95% confidence interval fitted by linear regression (c,d) Abundance of OTU259772 (Lachnospiraceae) by 16S sequencing (c) and abundance of Anaerostipes caccae by qPCR (d) in ileal samples from healthy- and CMA-colonized mice. LD indicates samples that were below the limit of detection for the assay. (e) Spearman's correlation between abundance of OTU259772 (Lachnospiraceae; 16S sequencing) and abundance of Anaerostipes caccae (qPCR) in ileal samples from healthy- and CMA-colonized mice. Circles represent individual mice and shaded bands indicate 95% confidence interval fitted by linear regression. Ileal samples that were above LD in both 16S and qPCR experiments are shown (n=19). (f) Gene expression of Ror2, Fbp1, Tgfbr3, Acot12 and Me1 in ileal IECs isolated from GF mice and from healthy- and CMA-colonized mice or mice monocolonized with A. caccae by qPCR. Data is normalized to Hprt as the housekeeping gene and shown as the fold change in expression from GF, set as 1. (g) Change in core body temperature at indicated time points following first challenge with BLG in BLG plus CT sensitized CMA and A. caccae-monocolonized mice. h-j, serum BLG-specific IgE (h) BLG-specific IgG1 and (i) mMCPT-1 (j) from mice in g. k,l IL-13 (k) and IL-4 (l) in culture supernatants of splenocytes from CMA or A. caccae colonized mice sacrificed 24 h post challenge and stimulated for 72 h with BLG. For c, d, f, and h-l circles represent individual mice, bars represent mean+s.e.m. For g, circles represent mean, bars represent s.e.m. For a-b, n=18 healthy-colonized or 18 CMA-colonized mice per group. For c and d, n=19 healthy-colonized or 21 CMA-colonized mice per group. For f, n=14 GF, 20 A. caccae-colonized, 18 healthy-colonized or 23 CMA-colonized mice per group.

For g-j n=16 CMA-colonized and 16 *A. caccae*-colonized mice collected from three independent experiments with two different CMA donors (5 and 6) and bars represent mean+ s.e.m. For k and l n=6 CMA-colonized and 9 *A. caccae*-colonized mice from one experiment, circles represent individual mice, bars represent mean+s.e.e. The DS-FDR method was used to compare groups in c, two-sided Student's t-test in d, one-way analysis of variance (ANOVA) with Bonferroni multiple testing correction in f or linear mixed-effect models in g, and two-sided t-tests in h-l after log transformation. *P<0.05, P<0.01, *P<0.001.

Figure 5:
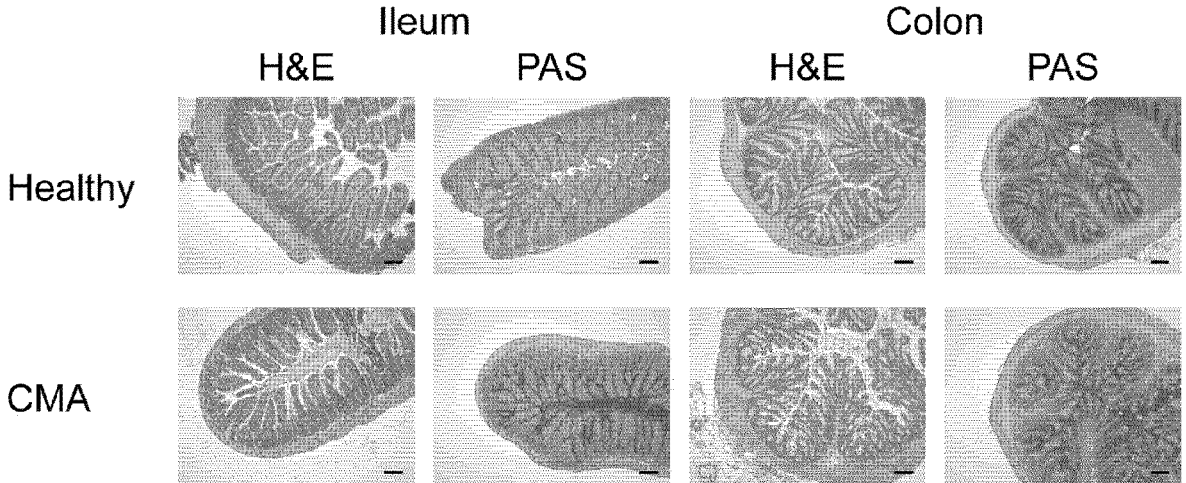

FIG. 5. Sensitization of healthy- or CMA-colonized mice with BLG plus cholera toxin does not result in intestinal pathology. Representative images of histological samples from BLG plus cholera toxin-sensitized healthy- or CMA-colonized mice 24 hours post-challenge for donors 1 (healthy) and 5 (CMA, see Supplementary Table 1). All sections stained with H&E or PAS, as indicated. Scale bars=100 m.

Figure 6:
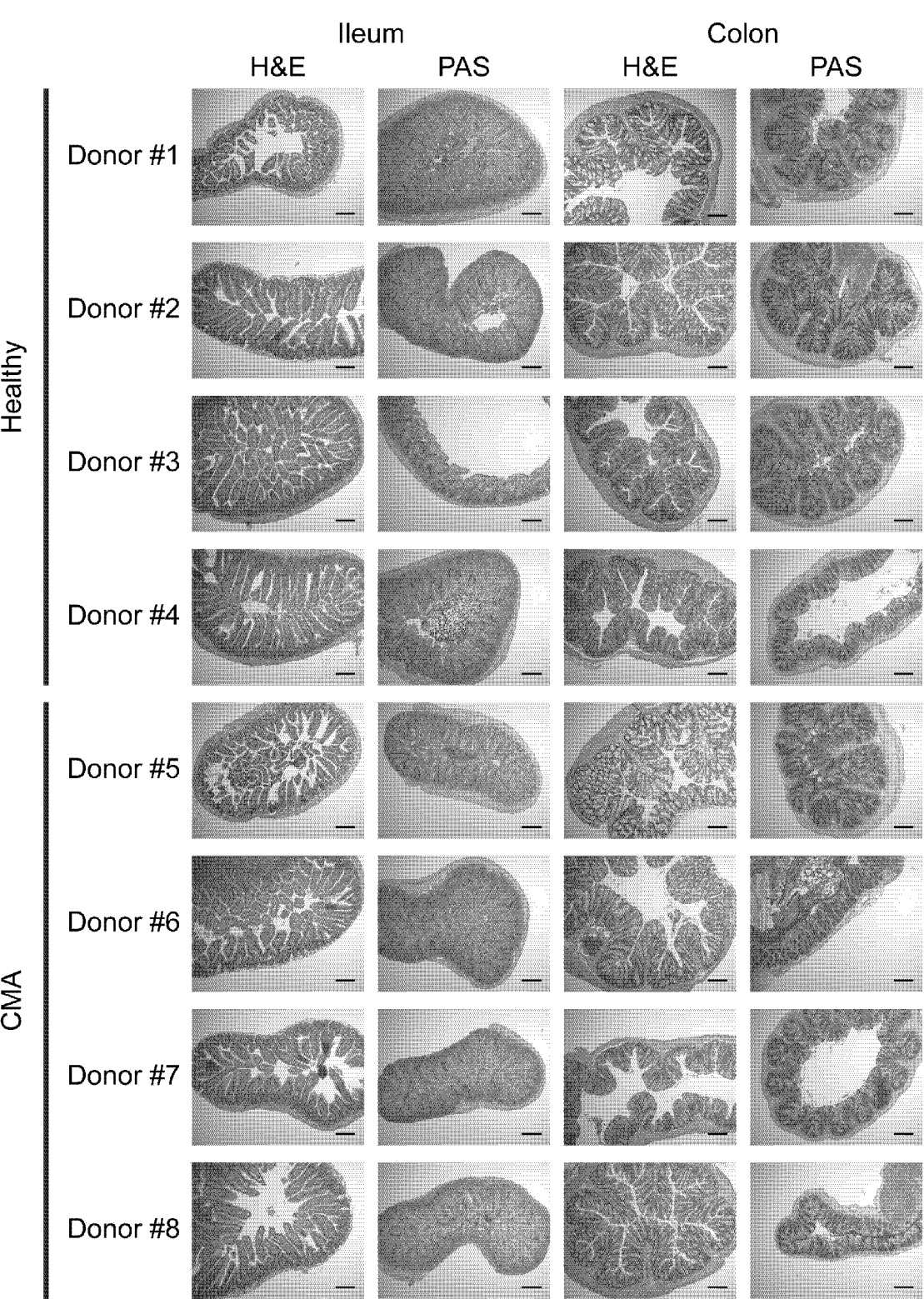

FIG. 6. Long term colonization of GF mice with feces from healthy or CMA infants does not lead to intestinal pathology. Representative images of histological samples from unsensitized healthy- or CMA-colonized mice collected 5 to 6 months post-colonization for donors described in Supplementary Table 1. All sections stained with H&E or PAS, as indicated. Scale bars=100 m.

FIG. 7A-B. Diversity analysis of fecal samples from healthy- or CMA-colonized mice. (a) Shannon Diversity index and (b) Pielou's Evenness index in feces from healthy-colonized (orange) and CMA-colonized (blue) mice from FIG. 2A. n=1-4 mice per colonized mouse group with feces taken at 2 and 3 weeks post-colonization (see Methods). Each circle represents one fecal sample, bars represent mean±s.e.m. The eight human formula-fed fecal donors are described in Supplementary Table 1.

FIG. 8A-D. Transfer of a healthy, exclusively breast-fed infant microbiota protects against an anaphylactic response to sensitization with BLG plus cholera toxin. (a) Change in core body temperature at indicated time points following first challenge with BLG of mice colonized with feces from breast-fed healthy or CMA infant donors (n=13 mice per group, collected from at least 2 independent experiments). (b-d) Serum BLG-specific IgE, (b) BLG-specific IgG1 (c) and mMCPT-1 (d) from mice in a. Four of the BLG+CT sensitized CMA-colonized mice died of anaphylaxis following challenge. For a, symbols represent mean, bars represent s.e.m. For b-d, symbols represent individual mice and bars represent mean+s.e.m. Linear mixed-effect models were used to compare groups in a and two-sided Student's t-test in b after log transformation. The two human breast-fed fecal donors are described in Supplementary Table 2. *P<0.05.

FIG. 9A-D. Continuous exposure to cow's milk does not induce tolerance to BLG in germ free mice fed with water or Enfamil® and sensitized with BLG plus cholera toxin. (a) Change in core body temperature at indicated time points following first challenge with BLG of mice fed with water (n=12) or Enfamil® (n=10) collected from three independent experiments. b-d, serum BLG-specific IgE, (b) BLG-specific IgG1 (c) and mMCPT-1 (d) from mice in a. For a, circles represent mean, error bars represent s.e.m. For b-d, circles represent individual mice, bars represent mean+ s.e.m. Linear mixed-effect models were used to compare groups in a and two-sided Student's t-tests in b-d after log transformation. **P<0.01. n.s.=not significant (P=0.36).

Figure 10A:
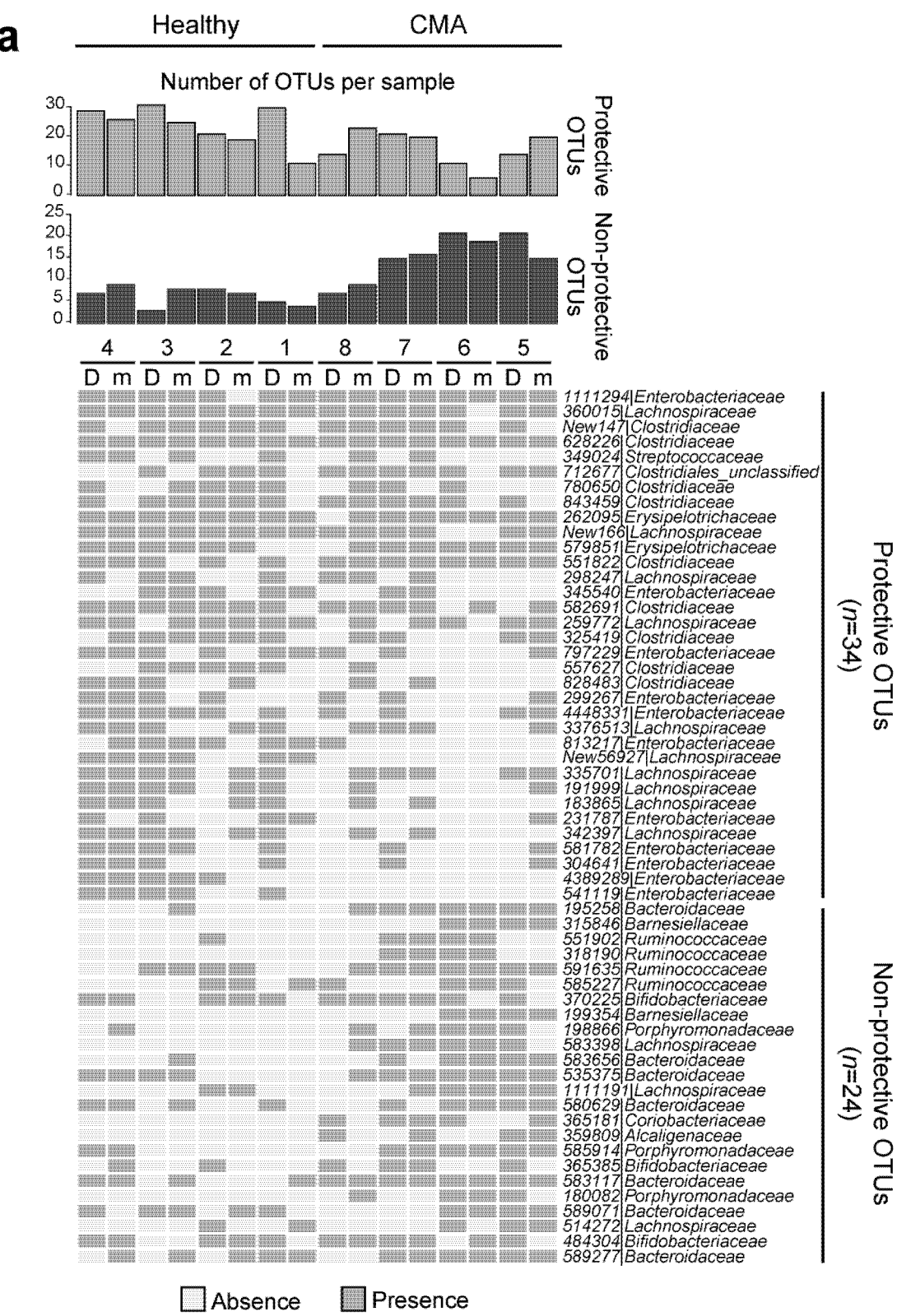
Figure 10B:
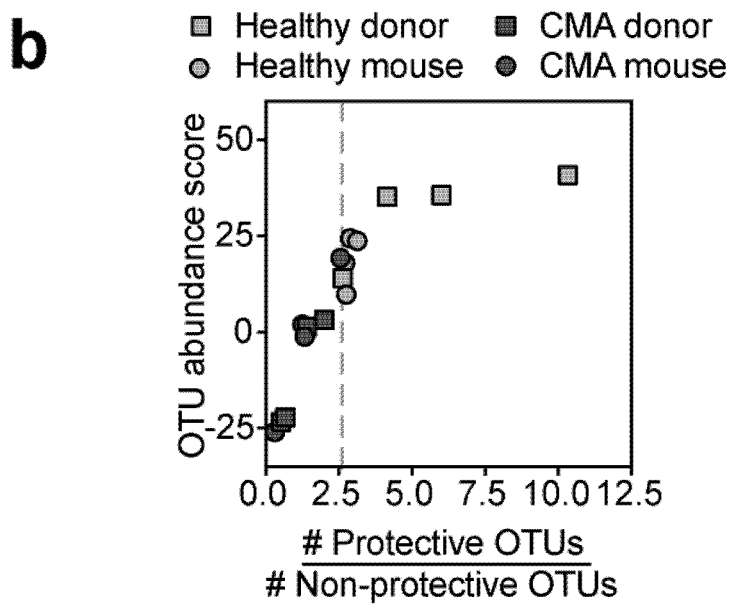

FIG. 10A-B. Binary representation of protective and non-protective OTUs in CMA and healthy donors and colonized mouse groups (a) Binary map of the presence/ absence ratio of protective/non-protective OTUs in CMA and healthy donors with the same layout as FIG. 2a. Columns depict each donor (D) or colonized mouse group (m). n=2-3 technical replicates per donor and n=1-4 mice per colonized mouse group with feces taken at 2 and 3 weeks post-colonization, see Methods). Rows show 58 OTUs FDR controlled at 0.10 (see Methods) in human CMA vs healthy donor comparison, present in at least 4 human fecal samples and at least two groups of colonized mice (see Supplementary Table 3). The bar graphs above the grid map represent the total number of potentially protective (more abundant in healthy donors; orange) and potentially non-protective (more abundant in CMA donors; blue) OTUs in each individual donor or mouse group. The grid map represents presence (green) or absence (white) of protective and non-protective OTUs in each sample. (b) A protective/non-protective OTU ratio was computed per individual donor or mouse group from a taking into consideration the presence or absence of 58 OTUs. The donors and their murine transfer recipients are shown in squares and circles, respectively. Vertical dashed line represents a ratio of 2.6.

Figure 11:
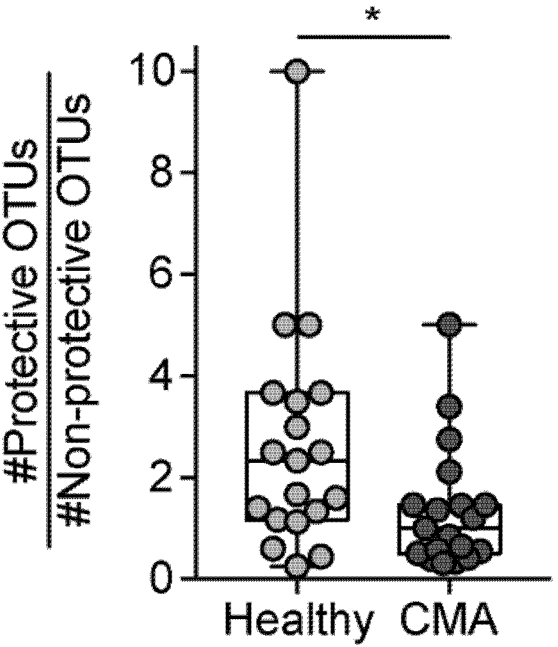

FIG. 11. Validation of protective/non-protective OTU ratio using a larger, independent cohort of healthy and CMA infant donors. Analysis of protective/non-protective OTU ratio (see FIG. 2 and FIG. 10) in fecal samples from healthy (n=19) and CMA (n=19) infants as previously isolated and described from reference 5. The horizontal center line indicates the median, the boxes represent the $25^{th}$ and $75^{th}$ percentiles, and the whiskers extend to the farthest data point within a maximum of 1.5 times the interquartile range (IQR). All individual points are shown, with each circle denoting a subject. Out of the 58 OTUs shown in FIG. 2A, 55 OTUs were assigned with known reference IDs and 3 with new reference IDs. The new reference OTU IDs are not comparable across the different analysis cohorts, therefore the inventors focused on the OTUs with known reference IDs. Among the 55 known OTUs, 52 (29 protective OTUs and 23 non-protective OTUs) were detected in this cohort and used for the ratio calculation (see Methods). The other 3 were not detected. Two-sided Wilcoxon rank sum test was used. *P<0.05.

FIG. 12A-C. The healthy vs CMA OTU abundance ratio is significantly correlated between mouse fecal and ileal samples. (a) Bubble plots show a similar pattern in fecal (n=8 mice in healthy group, n=9 mice in CMA group, with fecal samples collected at 2 and 3 weeks post-colonization, same as in FIG. 2A) and ileal samples (n=22 mice in healthy group, n=25 mice in CMA group) from healthy- and CMA-colonized mice. 58 OTUs significantly differentially abundant between CMA and healthy donors are shown in the same order as in FIG. 2A. The size of the circle indicates the magnitude of relative abundance enrichment towards either CMA or healthy. Color intensity indicates the statistical significance computed using the DS-FDR permutation test (see Methods). (b and c) The healthy versus CMA OTU abundance ratio is significantly correlated between mouse fecal and ileal samples. Each dot represents one individual OTU. For b, for each OTU, its average abundance was calculated at the group level among 8 healthy-colonized and 9 CMA-colonized mice for the fecal samples, and among 22 healthy-colonized and 25 CMA-colonized mice for the ileal samples. The ratios of OTU abundance in the feces are plotted on the x-axis with the ratio of OTU abundance in the ileum on the y-axis. For c, n=35 (15 healthy-colonized and 20 CMA-colonized) mice pooled from at least two independent experiments were used for the calculation of both the fecal and ileal OTU abundance ratio, where fecal and ileal samples were collected from the same individual mice. For further detail see Methods.

FIG. 13A-C. Abundance of OTU259772 (Lachno-spiraceae) and *Anaerostipes caccae* are correlated in fecal samples from healthy- and CMA-colonized mice. Abundance of OTU259772 (Lachnospiraceae) from the 16S data set and (a) abundance of *Anaerostipes caccae* by qPCR (b) in fecal samples from healthy-colonized (n=7) and CMA-colonized (n=8) mice from FIG. 2. For each individual mouse, 1-2 fecal samples were collected at 2 and 3 weeks post colonization. LD indicates samples that were below the limit of detection for the assay (c) Spearman's correlation between abundance of OTU259772 (Lachnospiraceae; 16S sequencing) and abundance of *Anaerostipes caccae* (qPCR) in fecal samples from healthy- and CMA-colonized mice from FIG. 2. Fecal samples that were above LD in both 16S and qPCR experiments are shown (n=13). Each circle represents one fecal sample. For a and b bars show mean+s.e.m. For c, shaded bands indicate 95% confidence interval fitted by linear regression. The DS-FDR method was used to compare groups in a and two-sided Student's t-test in b. ***P<0.001.

Figure 14:
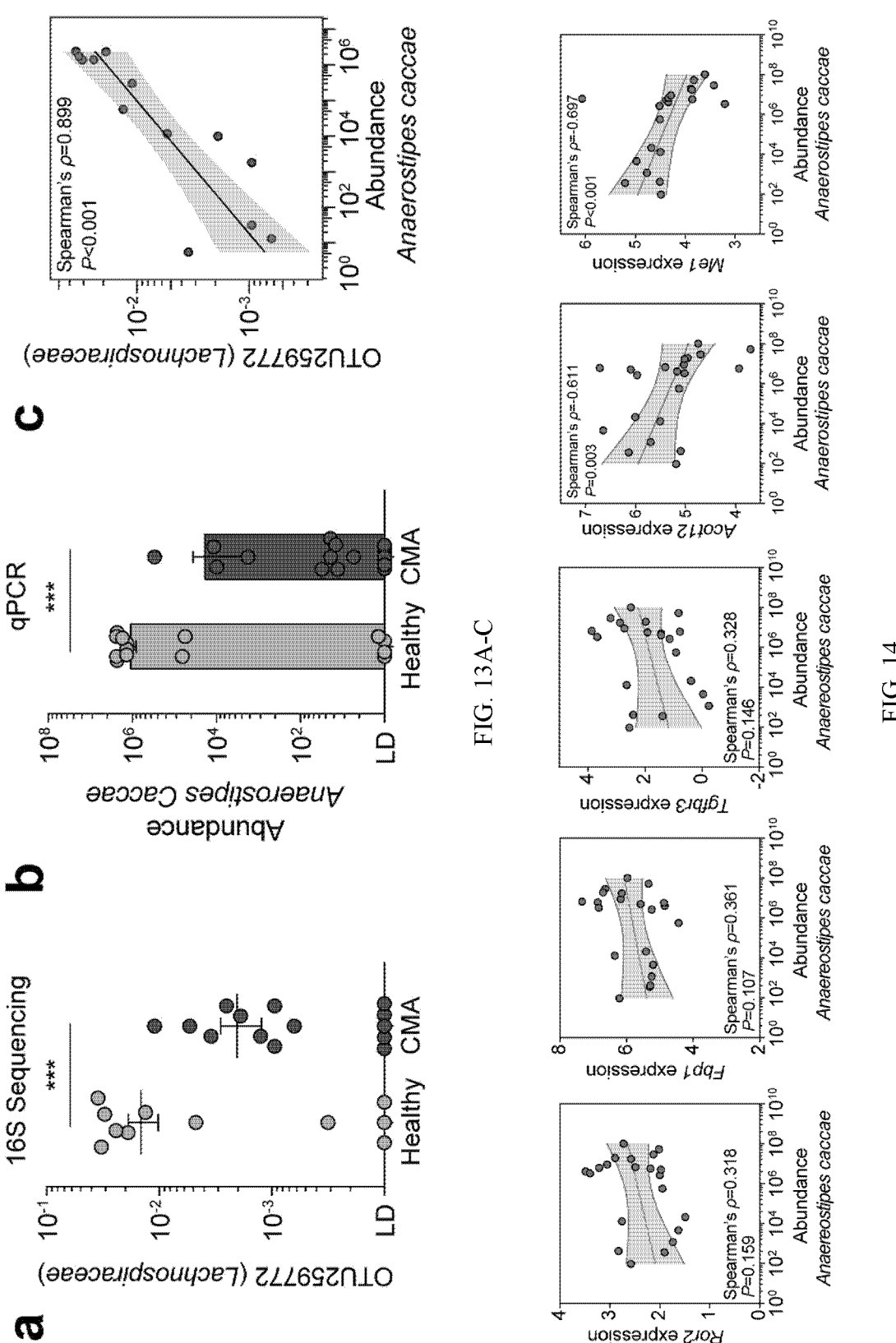

FIG. 14. Abundance of *Anaerostipes caccae* in ileal samples correlates with gene expression in ileal IECs. Spearman's correlation between abundance of *Anaerostipes caccae* by qPCR and RNA-Seq expression of Ror2, Fbp1, Tgfbr3, Acot12 and Me1 in ileal IECs (see FIG. 3A). Circles show individual mice and shaded bands indicate 95% confidence interval fitted by linear regression. n=36 (18 healthy- and 18 CMA-colonized) mice collected from at least two independent experiments. Samples with values above the limit of detection are shown (*A. caccae* abundance >0).

Figure 15:
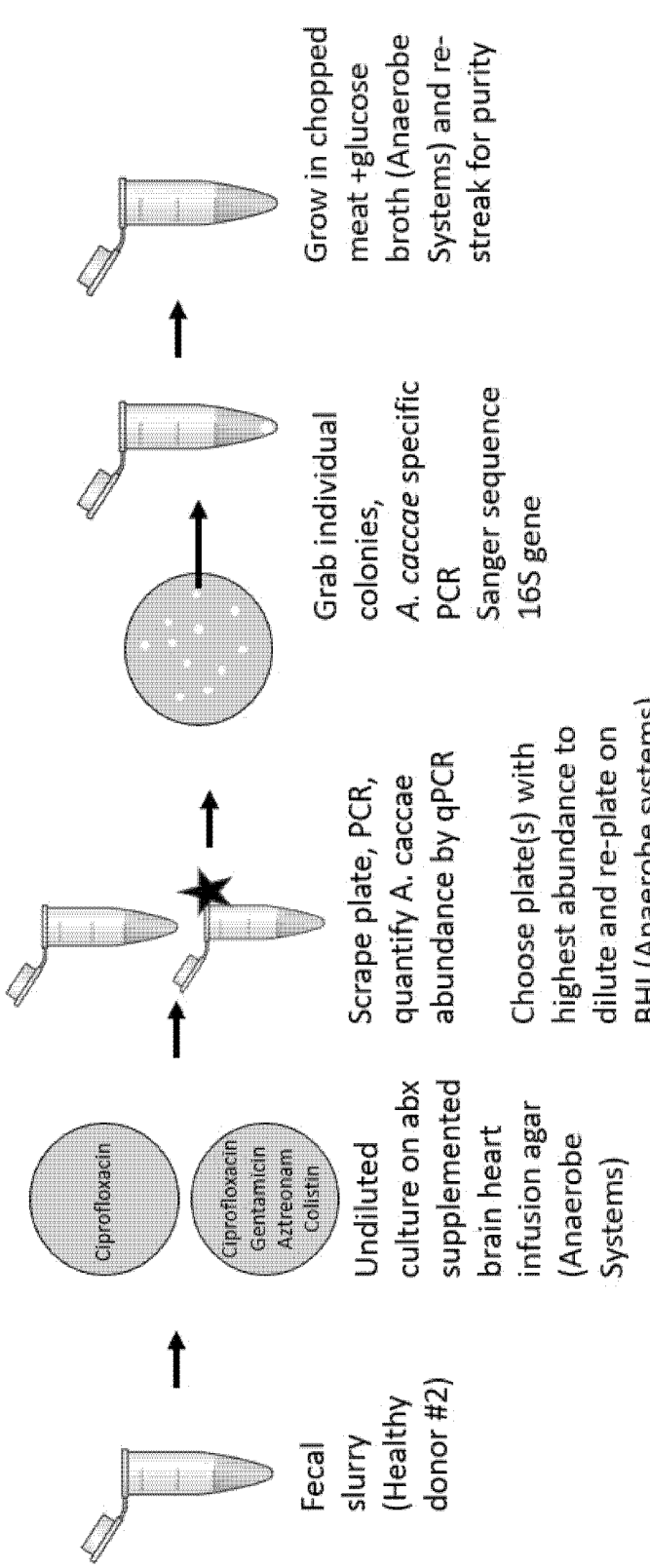

FIG. 15 shows *A. caccae* isolation and characterization schema.

Figure 16:
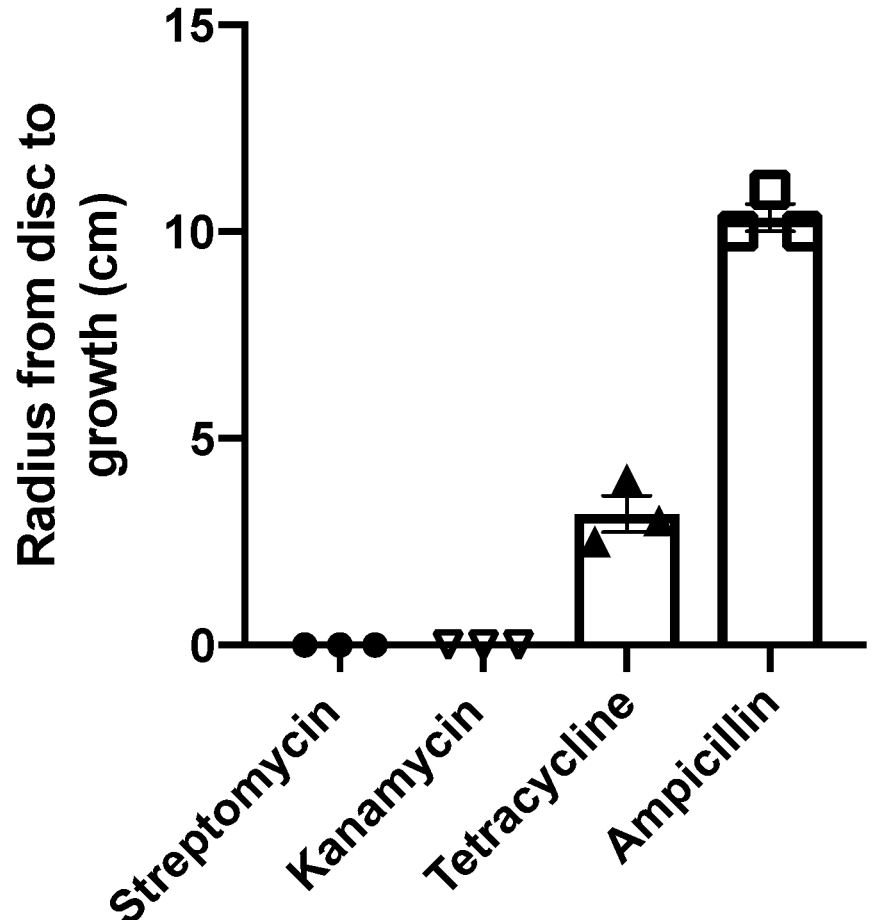

FIG. 16. *A. caccae*_lah is highly susceptible to ampicillin. It is also somewhat susceptible to tetracycline.

Figure 17:
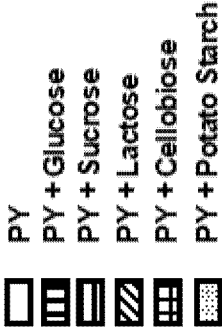

FIG. 17. *A. caccae*_lah is not able to ferment complex carbohydrates in monoculture but can ferment simple sugars like those in infant formula, including lactose. *A. caccae*_lah was grown from frozen stock for 24 h in CMG broth, then 10 ul was transferred into minimal peptone yeast (PY) broth supplemented with 10 mg/ml carbohydrates. Growth and butyrate production were measured after 48 h. All experiments were performed in duplicate and groups were analyzed by one way ANOVA. *P<0.05, P<0.01, *P<0.001, ****P<0.0001 versus PY alone.

FIG. 18. *A. caccae*_lah is able to use lactate and acetate together to produce butyrate. *A. caccae*_lah was grown from frozen glycerol stock for 24 h in CMG broth, then 10 µl was transferred into minimal PY broth supplemented with 33 mM acetate and/or 40 mM lactate. Growth and butyrate production was measured after 48 h. All experiments were performed in duplicate and groups were analyzed by one way ANOVA. *P<0.05, P<0.01, *P<0.001, ****P<0.0001 versus PY alone.

Figure 19:
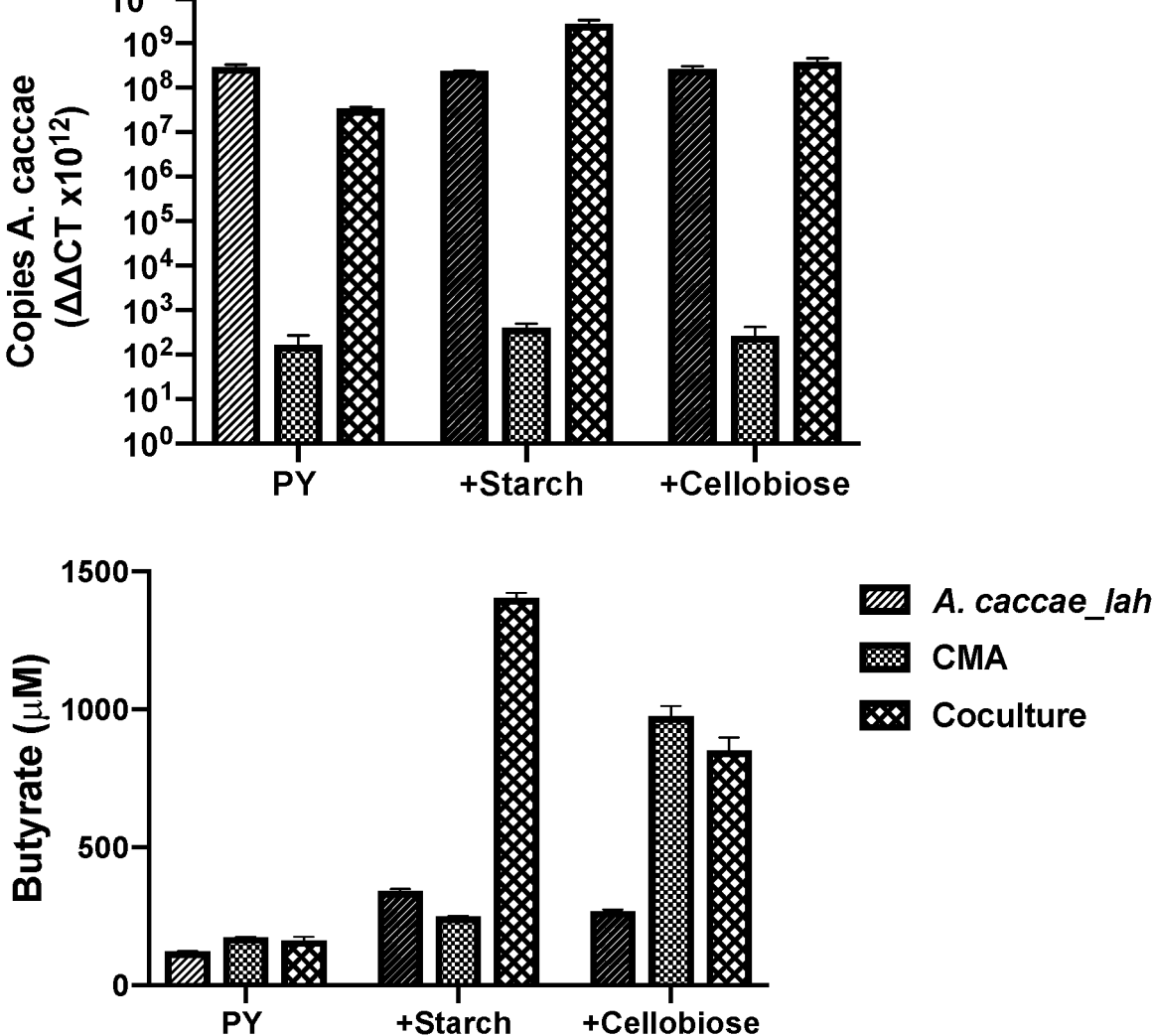

FIG. 19. *A. caccae*_lah produces substantially greater butyrate from fibers in co-culture with a complex bacterial mix from an allergic (CMA) infant donor. *A. caccae*_lah or human CMA fecal sample were grown from frozen glycerol stocks separately for 24 h in CMG broth, then 10 µl total was transferred into minimal PY broth supplemented with 10 mg/ml potato starch or cellobiose. Growth and butyrate production were measured after 48 h. All experiments were performed in duplicate.

Figure 20A:
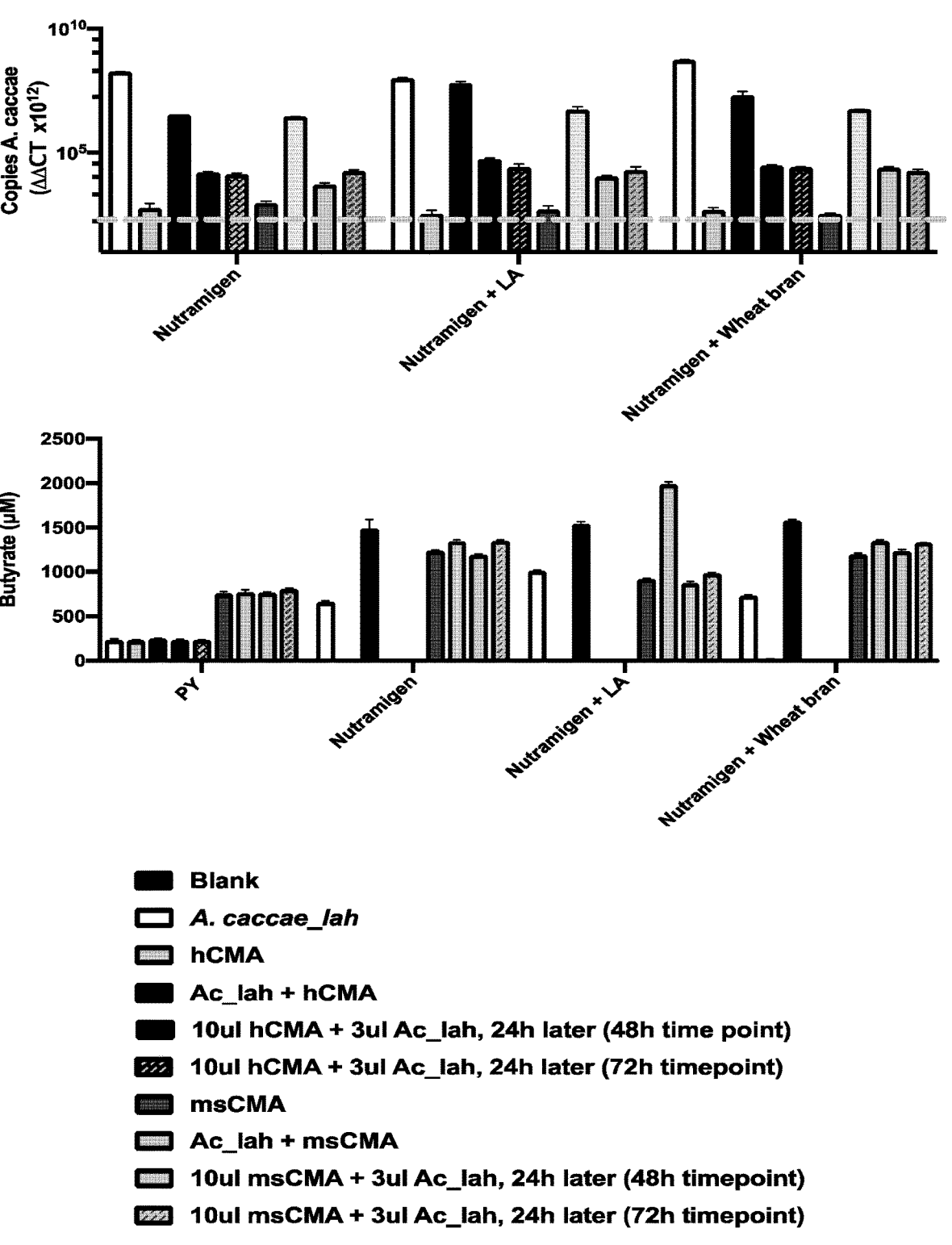
Figure 20B:
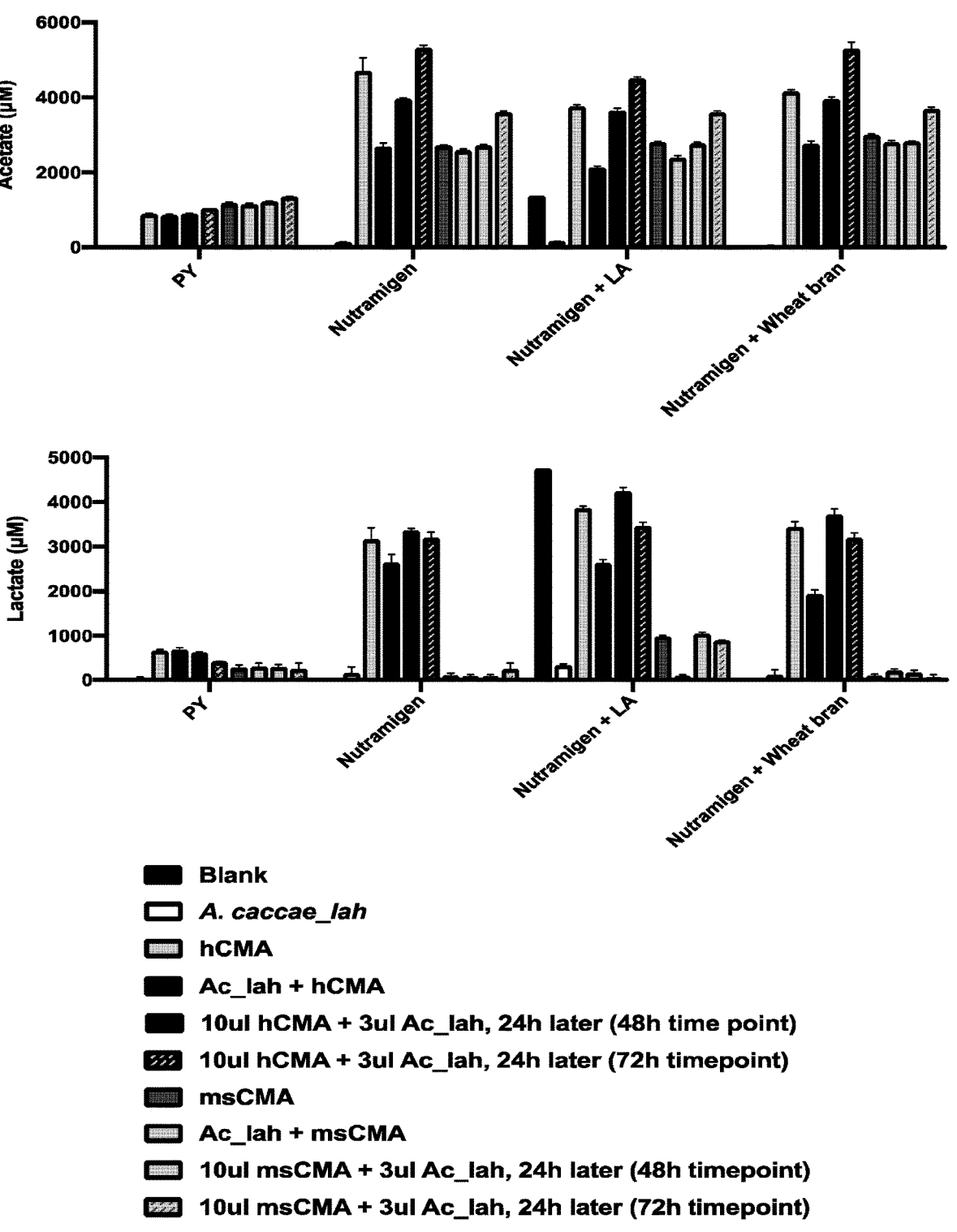

FIG. 20A-B. The bacterial mix from the CMA repository mouse feces produces more butyrate at baseline than human CMA feces from frozen glycerol stock (A), but addition of *A. caccae*_lah with lactate and acetate still results in a notable difference in butyrate levels (B). *A. caccae*_lah or the CMA mix, derived from human or mouse feces, were grown from frozen glycerol stocks for 24 h separately in CMG broth, then 10 µl total were transferred into minimal PY broth supplemented with 10 mg/ml carbohydrates. In the 24 h later group, CMA was transferred at time=0, *A. caccae*_lah and carbohydrates were transferred at time=24 h. Growth and butyrate production were measured after 48 h or 72 h. All experiments were performed in duplicate.

Figure 21:
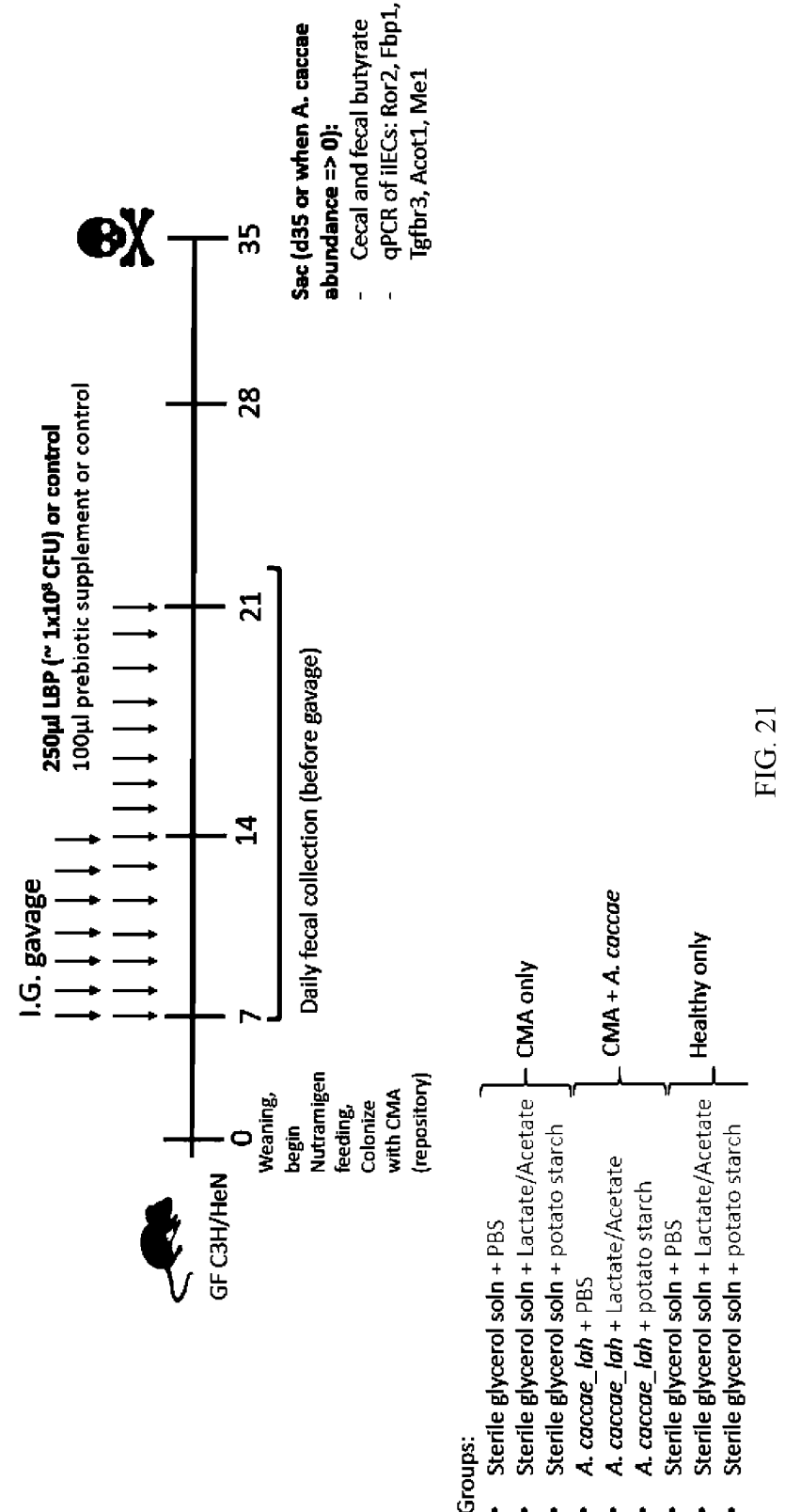

FIG. 21 depicts the experimental design to determine colonization of *A. caccae*_lah into CMA-colonized mice and dependence on prebiotic supplements.

DESCRIPTION OF ILLUSTRATIVE EMBODIMENTS

To better understand the role of the microbiota in regulating allergic disease in humans the inventors colonized germ free (GF) mice with bacteria derived from the feces of healthy or cow's milk allergic (CMA) infants. The inventors show here that colonization of germ-free mice with bacteria from healthy infants protected against sensitization to the cow's milk allergen β-lactoglobulin. Mice colonized with bacteria from CMA infants exhibited anaphylactic responses to BLG challenge and significantly increased serum BLG-specific IgE. Differences in bacterial composition separated the healthy and CMA populations in both the human donors and the colonized mice. RNA-Seq analysis of ileal intestinal epithelial cells revealed differentially expressed genes (DEGs) that distinguished healthy- and CMA-colonized mice across all donors. Correlation of ileal OTUs with DEGs in the ileum of healthy-colonized mice identified a Clostridial species, *Anaerostipes caccae*, that protected against an allergic response to food. The findings demonstrate that the composition of the intestinal microbiota is critical for regulating allergic responses to dietary antigens and suggest that interventions that modulate bacterial communities may be therapeutically relevant for food allergy.

I. Definitions

The term "unit dose" or "dosage" refers to physically discrete units suitable for use in a subject, each unit containing a predetermined quantity of the therapeutic composition calculated to produce the desired responses discussed herein in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any particular dose derivable therein. In non-limiting examples of a range derivable from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

"Subject" and "patient" refer to either a human or non-human, such as primates, mammals, and vertebrates. In particular embodiments, the subject is a human.

As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, and an increased lifespan as compared to that expected in the absence of treatment.

The term "isolated" encompasses a bacterium or other entity or substance that has been (1) separated from at least some of the components with which it was associated when initially produced (whether in nature or in an experimental setting), and/or (2) produced, prepared, purified, and/or manufactured by the hand of man. Isolated bacteria may be separated from at least about 10%, about 20%, about 30%, about 40%, about 50%, about 60%, about 70%, about 80%, about 90%, or more of the other components with which they were initially associated. In some embodiments, iso-lated bacteria are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

The terms "purify," "purifying" and "purified" refer to a bacterium or other material that has been separated from at least some of the components with which it was associated either when initially produced or generated (e.g., whether in nature or in an experimental setting), or during any time after its initial production. A bacterium or a bacterial popu-lation may be considered purified if it is isolated at or after production, such as from a material or environment con-taining the bacterium or bacterial population, and a purified bacterium or bacterial population may contain other mate-rials up to about 10%, about 20%, about 30%, about 40%, about 50%, about 60%, about 70%, about 80%, about 90%, or above about 90% and still be considered "isolated." In some embodiments, purified bacteria and bacterial popula-tions are more than about 80%, about 85%, about 90%, about 91%, about 92%, about 93%, about 94%, about 95%, about 96%, about 97%, about 98%, about 99%, or more than about 99% pure. In the instance of bacterial compositions provided herein, the one or more bacterial types present in the composition can be independently purified from one or more other bacteria produced and/or present in the material or environment containing the bacterial type. Bacterial com-positions and the bacterial components thereof are generally purified from residual habitat products.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional charac-teristic(s) of that embodiment of the invention. With respect to pharmaceutical compositions, the term "consisting essen-tially of" includes the active ingredients recited, excludes any other active ingredients, but does not exclude any pharmaceutical excipients or other components that are not therapeutically active.

The term "consisting of" refers to compositions, methods, and respective components thereof as described herein, which are exclusive of any element not recited in that description of the embodiment.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

As used herein, "essentially free," in terms of a specified component, is used herein to mean that none of the specified component has been purposefully formulated into a com-position and/or is present only as a contaminant or in trace amounts. The total amount of the specified component resulting from any unintended contamination of a compo-sition is therefore well below 0.01%. Most preferred is a composition in which no amount of the specified component can be detected with standard analytical methods.

The use of the term "or" in the claims is used to mean "and/or" unless explicitly indicated to refer to alternatives only or the alternatives are mutually exclusive, although the disclosure supports a definition that refers to only alterna-tives and "and/or." As used herein, the term "another" may mean at least a second or more.

Throughout this application, the term "about" is used to indicate that a value includes the inherent variation of error for the device, the method being employed to determine the value, or the variation that exists among the study subjects.

The phrase "effective amount" or "therapeutically effec-tive amount" or "sufficient amount" means a dosage of a drug or agent sufficient to produce a desired result.

II. Microbial Compositions

Embodiments of the present disclosure concern microbial compositions for the treatment of infectious, autoimmune, or allergic disease.

The present disclosure also provides a pharmaceutical composition comprising one or more microbial cultures as described above. The bacterial species therefore are present in the dose form as live bacteria, whether in dried or lyophilized form. This may be preferably adapted for suit-able administration; for example, in tablet or powder form, potentially with an enteric coating, for oral treatment.

In particular aspects, the composition is formulated for oral administration. Oral administration may be achieved using a chewable formulation, a dissolving formulation, an encapsulated/coated formulation, a multi-layered lozenge (to separate active ingredients and/or active ingredients and excipients), a slow release/timed release formulation, or other suitable formulations known to persons skilled in the art. Although the word "tablet" is used herein, the formulation may take a variety of physical forms that may commonly be referred to by other terms, such as lozenge, pill, capsule, or the like.

While the compositions of the present disclosure are preferably formulated for oral administration, other routes of administration can be employed, however, including, but not limited to, subcutaneous, intramuscular, intradermal, transdermal, intraocular, intraperitoneal, mucosal, vaginal, rectal, and intravenous.

The desired dose of the composition of the present disclosure may be presented in multiple (e.g., two, three, four, five, six, or more) sub-doses administered at appropriate intervals throughout the day, week, month or year.

In one aspect, the disclosed composition may be prepared as a capsule. The capsule (i.e., the carrier) may be a hollow, generally cylindrical capsule formed from various substances, such as gelatin, cellulose, carbohydrate or the like.

In another aspect, the disclosed composition may be prepared as a suppository. The suppository may include but is not limited to the bacteria and one or more carriers, such as polyethylene glycol, acacia, acetylated monoglycerides, carnuba wax, cellulose acetate phthalate, corn starch, dibutyl phthalate, docusate sodium, gelatin, glycerin, iron oxides, kaolin, lactose, magnesium stearate, methyl paraben, pharmaceutical glaze, povidone, propyl paraben, sodium benzoate, sorbitan monoleate, sucrose talc, titanium dioxide, white wax and coloring agents.

In some aspects, the disclosed microbial composition may be prepared as a tablet. The tablet may include the bacteria and one or more tableting agents (i.e., carriers), such as dibasic calcium phosphate, stearic acid, croscarmellose, silica, cellulose and cellulose coating. The tablets may be formed using a direct compression process, though those skilled in the art will appreciate that various techniques may be used to form the tablets.

In other aspects, the disclosed microbial composition may be formed as food or drink or, alternatively, as an additive to food or drink, wherein an appropriate quantity of bacteria is added to the food or drink to render the food or drink the carrier.

In some embodiments, the microbial composition may further comprise a food or a nutritional supplement effective to stimulate the growth of *A. caccae* present in the gastrointestinal tract of the subject. In some embodiments, the nutritional supplement is produced by another bacterium associated with a healthy human gut microbiome.

III. Administration of Therapeutic Compositions

The therapy provided herein comprises administration of a combination of therapeutic agents, such as microbial compositions and prebiotics. The therapy may be administered in any suitable manner known in the art. For example, the microbial composition and the prebiotic may be administered sequentially (at different times) or concurrently (at the same time). In some embodiments, the microbial composition and the prebiotic are in a separate composition. In some embodiments, the microbial composition and the prebiotic are in the same composition.

Embodiments of the disclosure relate to compositions and methods comprising bacteria and one or more prebiotics. The bacteria and/or prebiotic(s) may be administered in one composition or in more than one composition, such as 2 compositions, 3 compositions, or 4 compositions. Various combinations of the agents may be employed, for example, a bacterium (or composition comprising bacteria) is "A" and a prebiotic is "B":

16

| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A |
| B/A/B/A | B/A/A/B | A/A/A/B | B/A/A/A | A/B/A/A | A/A/B/A |

In some embodiments, the microbial composition is administered prior to the prebiotic. In some embodiments, the microbial composition is administered at least, at most, or about 1, 2, 3, 5, 6, 12, 24 hours or 2, 3, 4, 6, 8, 10, days or 2, 3, 4, 5, 6, 7, or 8 weeks (or any derivable range therein) prior to the prebiotic. In some embodiments, at least 1, 2, 3, 4, 5, 6, or 7 doses (or any derivable range therein) of the microbial composition is administered at least, at most, or about 1, 2, 3, 5, 6, 12, 24 hours or 2, 3, 4, 6, 8, 10, days or 2, 3, 4, 5, 6, 7, or 8 weeks (or any derivable range therein) prior to the prebiotic. In some embodiments, the microbial composition is administered after the prebiotic. In some embodiments, the microbial composition is administered at least, at most, or about 1, 2, 3, 5, 6, 12, 24 hours or 2, 3, 4, 6, 8, 10, days or 2, 3, 4, 5, 6, 7, or 8 weeks (or any derivable range therein) after the prebiotic or after at least one of the prebiotics or after at least 2 of the prebiotics. In some embodiments, at least 1, 2, 3, 4, 5, 6, or 7 doses (or any derivable range therein) of the microbial composition is administered at least, at most, or about 1, 2, 3, 5, 6, 12, 24 hours or 2, 3, 4, 6, 8, 10, days or 2, 3, 4, 5, 6, 7, or 8 weeks (or any derivable range therein) after the prebiotic or after at least one of the prebiotics or after at least 2 of the prebiotics.

In some embodiments, the microbial modulator composition is formulated for oral administration. The skilled artisan knows a variety of formulas which can encompass living or killed microorganisms and which can present as food supplements (e.g., pills, tablets and the like) or as functional food such as drinks or fermented yogurts.

The agents of the disclosure may be administered by the same route of administration or by different routes of administration. In some embodiments, the prebiotic is administered intravenously, intramuscularly, subcutaneously, topically, orally, transdermally, intraperitoneally, intraorbitally, by implantation, by inhalation, intrathecally, intraventricularly, or intranasally. In some embodiments, the microbial composition is administered intravenously, intramuscularly, subcutaneously, topically, orally, transdermally, intraperitoneally, intraorbitally, by implantation, by inhalation, intrathecally, intraventricularly, or intranasally. The appropriate dosage may be determined based on the type of disease to be treated, severity and course of the disease, the clinical condition of the individual, the individual's clinical history and response to the treatment, and the discretion of the attending physician.

For example, the therapeutically effective or sufficient amount of each of the at least one isolated or purified population of bacteria or each of the at least two, 3, 4, 5, 6, 7, 8, 9, 10 11, 12, 13, 14, or 15 isolated or purified populations of bacteria of the microbial modulator compositions of the embodiments that is administered to a human will be at least about $1\times10^3$ colony forming units (CFU) of bacteria or at least about $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ CFU (or any derivable range therein). In some embodiments, a single dose will contain bacteria (such as a specific bacteria or species, genus, or family described herein) present in an amount of least, at most, or about $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ or more CFU (or any derivable range therein). In some embodiments, a single dose will contain at least, at most, or about $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ or greater than $1\times10^{15}$ CFU (or any derivable range therein) of total bacteria.

In some embodiments, the therapeutically effective or sufficient amount of each of the at least one isolated or purified population of bacteria of the microbial compositions of the embodiments that is administered to a human will be at least about $1\times10^3$ cells of bacteria or at least about $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ cells (or any derivable range therein). In some embodiments, a single dose will contain bacteria (such as a specific bacteria or species, genus, or family described herein) present in an amount of at least, at most, or about $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ or more cells (or any derivable range therein). In some embodiments, a single dose will contain at least, at most, or about $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ or greater than $1\times10^{15}$ cells (or any derivable range therein) of total bacteria.

The treatments may include various "unit doses." Unit dose is defined as containing a predetermined-quantity of the therapeutic composition. The quantity to be administered, and the particular route and formulation, is within the skill of determination of those in the clinical arts. A unit dose need not be administered as a single injection but may comprise continuous infusion over a set period of time. In some embodiments, a unit dose comprises a single administrable dose.

The quantity to be administered, both according to number of treatments and unit dose, depends on the treatment effect desired. An effective dose is understood to refer to an amount necessary to achieve a particular effect. In the practice in certain embodiments, it is contemplated that doses in the range from 10 mg/kg to 200 mg/kg can affect the protective capability of these agents. Thus, it is contemplated that doses include doses of about 0.1, 0.5, 1, 5, 10, 15, 20, 25, 30, 35, 40, 45, 50, 55, 60, 65, 70, 75, 80, 85, 90, 100, 105, 110, 115, 120, 125, 130, 135, 140, 145, 150, 155, 160, 165, 170, 175, 180, 185, 190, 195, and 200, 300, 400, 500, 1000 µg/kg, mg/kg, µg/day, or mg/day or any range derivable therein. Furthermore, such doses can be administered at multiple times during a day, and/or on multiple days, weeks, or months.

In certain embodiments, the effective dose of the pharmaceutical composition is one which can provide a blood level of about 1 µM to 150 µM. In another embodiment, the effective dose provides a blood level of about 4 µM to 100 µM; or about 1 µM to 100 µM; or about 1 µM to 50 µM; or about 1 µM to 40 µM; or about 1 µM to 30 µM; or about 1 µM to 20 µM; or about 1 µM to 10 µM; or about 10 µM to 150 µM; or about 10 µM to 100 µM; or about 10 µM to 50 µM; or about 25 µM to 150 µM; or about 25 µM to 100 µM; or about 25 µM to 50 µM; or about 50 µM to 150 µM; or about 50 µM to 100 µM (or any range derivable therein). In other embodiments, the dose can provide the following blood level of the agent that results from a therapeutic agent being administered to a subject: about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 M or mM or any range derivable therein. In certain embodiments, the therapeutic agent that is administered to a subject is metabolized in the body to a metabolized therapeutic agent, in which case the blood levels may refer to the amount of that agent. Alternatively, to the extent the therapeutic agent is not metabolized by a subject, the blood levels discussed herein may refer to the unmetabolized therapeutic agent.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance or other therapies a subject may be undergoing.

It will be understood by those skilled in the art and made aware that dosage units of µg/kg or mg/kg of body weight can be converted and expressed in comparable concentration units of µg/ml or M or mM (blood levels), such as 4 µM to 100 µM. It is also understood that uptake is species and organ/tissue dependent. The applicable conversion factors and physiological assumptions to be made concerning uptake and concentration measurement are well-known and would permit those of skill in the art to convert one concentration measurement to another and make reasonable comparisons and conclusions regarding the doses, efficacies and results described herein.

Prebiotics may be formulated using techniques of pharmaceutical formulation known in the art. They may be formulated using specialized techniques known for delivery to specific regions of the gastrointestinal tract. Two examples known in the art are described in published PCT application WO 2018/195067 A1 and also in U.S. patent application Ser. No. 15/257,673, each of which are incorporated by reference. Other formulations for prebiotics or combinations of prebiotics and *A. caccae* are known in the art. In some embodiments, the compositions of the disclosure include a butyrate carrying compound, such as those described in WO 2018/195067.

IV. Methods of Treatment

The methods of the disclosure relate to the treatment of infectious, autoimmune, or allergic disease. In some embodiments, the method is for the treatment of a food allergy. In some embodiments, the food allergy comprises a milk allergy. In some embodiments, the milk allergy comprises cow's milk allergy. In some embodiments, the milk allergy comprises cow, goat, or sheep milk allergy. In some embodiments, the method is for treating allergies, asthma, diabetes (e.g. type 1 diabetes), graft rejection, arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and systemic juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, juvenile onset (Type I) diabetes mellitus, including pediatric insulin-dependent diabetes mellitus (IDDM), and adult onset diabetes mellitus (Type II diabetes) and autoimmune diabetes. Also contemplated are immune responses associated with acute and delayed hypersensitivity mediated by cytokines and T-lymphocytes, sarcoidosis, granulomatosis including lymphomatoid granulomatosis, Wegener's granulomatosis, agranulocytosis, vasculitides, including vasculitis, large-vessel vasculitis (including polymyalgia rheumatica and gianT cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), Addison's disease, autoimmune neutropenia, pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Behcet's disease/syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus *foliaceus*, pemphigus mucus-membrane pemphigoid, and pemphigus erythematosus), autoimmune polyendocrinopathies, Reiter's disease or syndrome, thermal injury, preeclampsia, an immune complex disorder such as immune complex nephritis, antibody-mediated nephritis, polyneuropathies, chronic neuropathy such as IgM polyneuropathies or IgM-mediated neuropathy, autoimmune or immune-mediated thrombocytopenia such as idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), experimental autoimmune encephalomyelitis, myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, gianT cell hepatitis, chronic active hepatitis or autoimmune chronic active hepatitis, lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia greata, alopecia totalis, CREST syndrome (calcinosis, Raynaud's phenomenon, esophageal dysmotility, sclerodactyl) and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis, endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, gianT cell polymyalgia, chronic hypersensitivity pneumonitis, keratoconjunctivitis sicca, epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders, aspernio-genese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, non-malignant thymoma, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism, neurological disease, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, graft versus host disease, contact hypersensitivity, asthmatic airway hyperreaction, and endometriosis.

V. Kits

Certain aspects of the disclosure also encompass kits for performing the methods of the disclosure, such as kits comprising the compositions described herein. Kits may comprise a container with a label. Suitable containers include, for example, bottles, vials, and test tubes. The containers may be formed from a variety of materials such as glass or plastic. The container may hold a composition which includes a probe that is useful for prognostic or non-prognostic applications, such as described above. The label on the container may indicate that the composition is used for a specific prognostic or non-prognostic application, and may also indicate directions for either in vivo or in vitro use, such as those described above. The kit may comprise the container described above and one or more other containers comprising materials desirable from a commercial and user standpoint, including buffers, diluents, filters, needles, syringes, and package inserts with instructions for use.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Healthy Infants Harbor Intestinal Bacteria that Protect Against Food Allergy B. Results Work from the inventors' laboratory and others demonstrated that the fecal microbial communities of infants with CMA are markedly different from those of their healthy counterparts (5, 6). Based on these results, as well as evidence that members of the microbiota can be allergy protective (7), the inventors used a gnotobiotic mouse model to investigate whether commensal bacteria play a causal role in protection against an allergic response to the cow's milk allergen β-lactoglobulin (BLG). Germ free (GF) mice were colonized with human feces from four healthy and four IgE-mediated cow's milk allergic (CMA) infant donors who were matched for age, gender and mode of birth (8, 9) (Supplementary Table 1). It has previously been reported that diet is important for the stable colonization of germ-free mice with human feces (ref. 10). To support the growth of human bacteria in the murine hosts, mice received feces from formula-fed healthy or CMA infants and were fed the same formulas consumed by their human infant donors in addition to plant-based mouse chow. The CMA infant donors received an extensively hydrolyzed casein formula (EHCF) to manage ongoing allergic symptoms while the healthy donors received a standard cow's milk-based formula (5). Initial transfer recipients were used as living repositories for subsequent experiments (see Methods).

Groups of GF mice and mice colonized with either the healthy or CMA infant microbiota were sensitized with BLG and the mucosal adjuvant cholera toxin (CT). GF mice, devoid of any bacterial colonization, were highly susceptible to anaphylactic responses to food as evidenced by a drop in core body temperature (FIG. 1A) and production of BLG-specific IgE and IgG1 (FIG. 1B, C) (7, 11). The inventors also measured a substantial reduction in core body temperature in mice colonized with fecal samples from each of the four CMA donors in response to BLG challenge (FIG. 1A). Sensitized CMA-colonized mice produced significantly higher serum concentrations of BLG-specific IgE (FIG. 1B), IgG1 (FIG. 1C) and mMCPT-1 (FIG. 1D) when compared to healthy-colonized mice. Strikingly, all of the mice that received the four healthy infant microbiotas were protected from an anaphylactic response to BLG challenge; their core body temperature post-challenge was significantly different from that measured in GF or CMA-colonized mice (FIG. 1A). Histological analysis did not reveal any evidence of pathology or inflammation in ileal or colonic tissue samples taken post-challenge (FIG. 5) or after long term colonization (FIG. 6). Microbial analysis revealed that community diversity and evenness were similar between healthy and CMA colonized mouse groups (FIG. 7). To examine whether the cow's milk containing formula contributed to microbiota-independent protection against anaphylaxis in the healthy-colonized mice, the inventors performed additional fecal transfers from breast-fed healthy and CMA donors (Supplementary Table 2). Recipient mice received only plant-based mouse chow. Mice colonized with feces from the breast-fed healthy donor were protected from an anaphylactic response to BLG sensitization and challenge. However, mice colonized with feces from a breast-fed CMA donor exhibited a significantly greater drop in core body temperature compared to healthy-colonized mice (FIG. 8A) and higher levels of BLG specific IgE (FIG. 8B). Sensitization was also compared to BLG in GF mice fed water or Enfamil®. Both groups of mice responded robustly to sensitization with BLG (FIG. 9). There was no significant difference in their drop in core body temperature post challenge or in serum concentrations of BLG-specific IgE or IgG1; serum mMCPT-1 was, however, suppressed in mice fed the cow's milk containing formula.

Figure 2A:
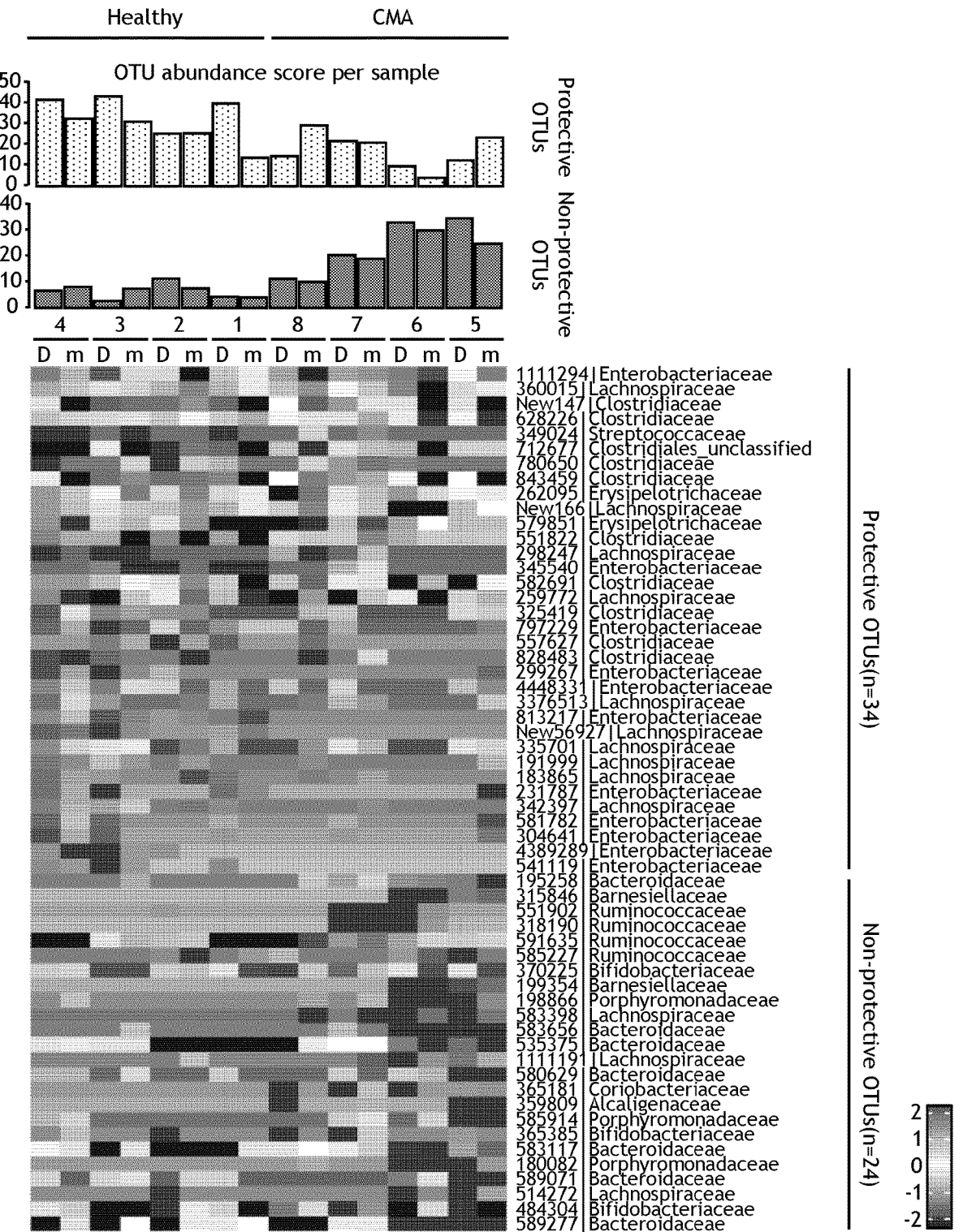
FIG. 2A-F. Analysis of fecal samples from eight human infant donors reveals taxonomic signatures that correlate with allergic phenotype. (a) Heatmap of OTUs differentially abundant between CMA and healthy donors. Rows show 58 OTUs identified as different at false-discovery rate (FDR) controlled at 0.10 and present in at least 4 human fecal samples and at least two groups of colonized mice (see Supplementary Table 3). Columns depict each donor (D) or colonized mouse group (m). n=2-3 technical replicates per donor, n=1-4 mice per colonized mouse group with feces taken at 2 and 3 weeks post-colonization (see Methods). The bar graphs above the heatmap represent the abundance score of potentially protective (orange) or non-protective (blue) OTUs calculated for each donor or mouse group. (b-d) The ratio of protective over non-protective OTUs (see FIG. 10B) derived from colonized mice in a plotted against levels of BLG-specific IgE, (b) BLG-specific IgG1 (c), and mMCPT-1 (d) from all mice in FIG. 1. Each circle represents average results from all mice colonized with each of the four healthy (orange) or CMA (blue) donor's feces. (e) LEfSe analysis of taxa that were significantly enriched in healthy-colonized mice (orange) or CMA-colonized mice (blue) from samples in a (n=8 mice in healthy group and n=9 mice in CMA group, with fecal samples collected at 2 and 3 weeks post-colonization). (f) Cladogram showing the community composition of colonized mouse samples from a, with the taxa detected as differentially abundant by LEfSe analysis colored by group (healthy=orange, CMA=blue). The discrete false discovery rate (DS-FDR) method was used to compare groups in a and the Kruskal-Wallis test was performed in e (see Methods).
Figure 2B:
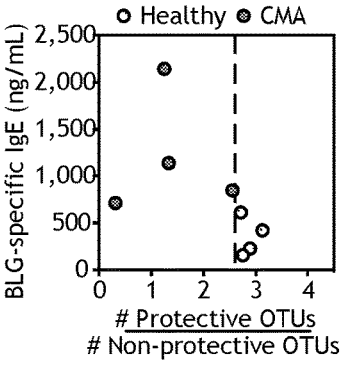
Figure 2C:
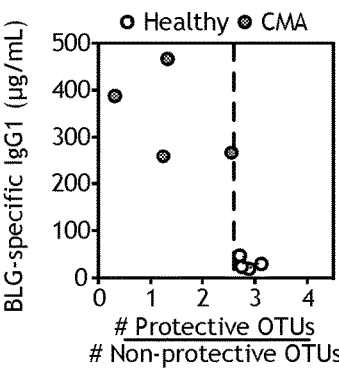
Figure 2D:
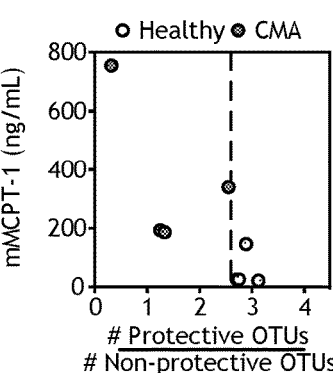
Figure 2E:
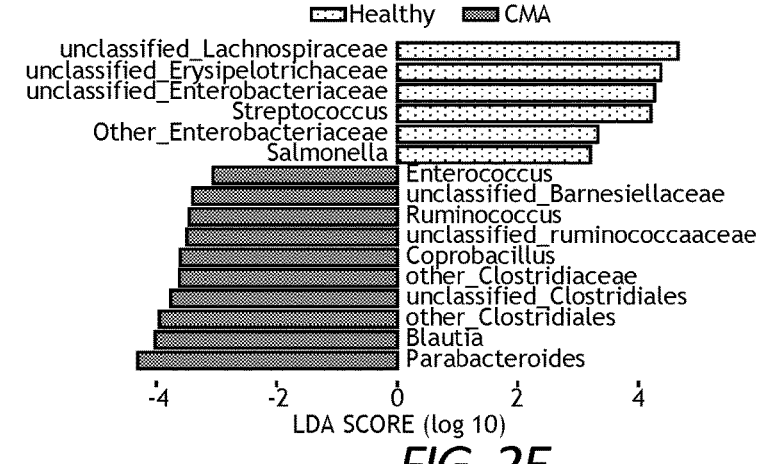
Figure 2F:
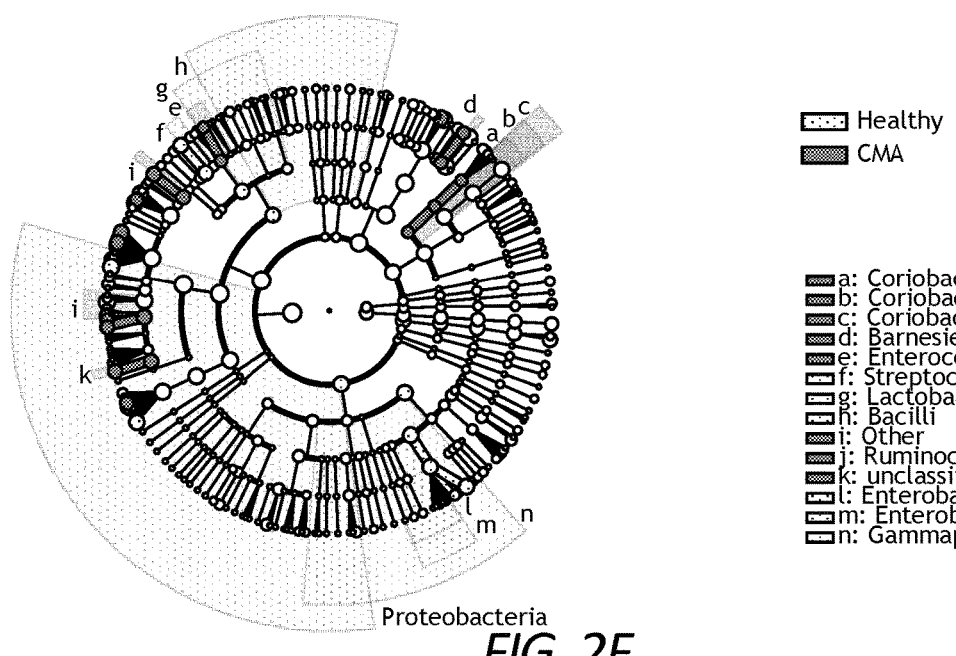

Analysis of fecal samples from the eight formula-fed human infant donors (Supplementary Table 1) identified 58 operational taxonomic units (OTUs) that were differentially abundant between healthy and CMA infants (FIG. 2A; Supplementary Table 3). Since variation exists between each donor and murine transfer recipient at the single OTU level, the inventors examined whether donor-derived microbiome composition differences were able to distinguish the colonized mouse groups. As an aggregated measure to present the data, the inventors calculated the number of potentially "protective" (more abundant in healthy donors, n=34) and potentially "non-protective" (more abundant in CMA donors, n=24) OTUs to produce a presence/absence ratio for each donor (FIG. 10A; see Methods). In addition, the inventors calculated a score weighted toward each OTU based on its relative abundance in the sample (hereafter called abundance score) (FIG. 2A; see Methods). When the OTU abundance score was plotted against the presence/absence ratio, donors segregated by ratio into the healthy and CMA groups (FIG. 10B, squares). This threshold also separated the CMA- and healthy-colonized mice by their biological phenotype (FIG. 10B, circles), demonstrating that this donor-derived aggregated microbiota signature is validated in the murine transfer recipients. The significantly higher protective/non-protective OTU ratio in healthy infants relative to those with CMA was independently corroborated in an unrelated set of samples from the same Neapolitan cohort by reanalysis of 16S fecal sample data collected in a previously published study (5) (FIG. 11). The donor-derived OTU ratio also separated healthy- and CMA-colonized mice when plotted against biomarkers of allergic disease including BLG-specific IgE (FIG. 2B), BLG-specific IgG1 (FIG. 2C) and mMCPT-1 (FIG. 2D). Interestingly, linear discriminant effect size (LEfSe) analysis (FIG. 2E, F) showed that Lachnospiraceae, a family in the Clostridia class, were enriched in the healthy colonized mice (7).

Tolerance to dietary antigens begins with their absorption in the small intestine (4, 12). Most commensal bacteria reside in the colon; in the small intestine, bacteria are most numerous in the ileum (13). The interaction of these bacteria with IECs is central to regulation of immunity at the host-microbe interface (13, 14). Ileal IECs were isolated from groups of mice colonized by each of the eight infant donors and quantified gene expression by RNASeq (FIG. 3A). Healthy-colonized mice upregulated a unique set of ileal genes compared to CMA-colonized mice (FIG. 3A; Supplementary Table 4). For example, Fbp1, which encodes a key gluconeogenic enzyme abundantly expressed in epithelial cells of the small intestine (15), was significantly upregulated across all healthy-colonized mice (FIG. 3A). Reduced expression of Fbp1 has been associated with a metabolic switch from oxidative phosphorylation to aerobic glycolysis (16, 17) which alters oxygenation of the epithelium and contributes to dysbiosis (18). Tgfbr3 and Ror2 were downregulated in the ileum of CMA-colonized mice relative to healthy-colonized mice (FIG. 3A). Tgfbr3 encodes a receptor for the growth factor TGF-β and is abundantly expressed in the small intestine of suckling rats (19). Soluble TGFβRIII and TGF-β2 are present at high concentrations in breast milk; activation of TGF-β signaling by Wnt5a is mediated through Ror2 and is important for epithelial repair (20). By contrast, Acot12 and Me1, genes involved in pyruvate metabolism, were upregulated in the ileum of CMA-colonized mice relative to healthy-colonized mice. These metabolic and molecular processes are reflected in the Gene Ontology pathways significantly altered in CMA- and healthy-colonized mice depicted in FIG. 3B.

Figures 4A, 4B:
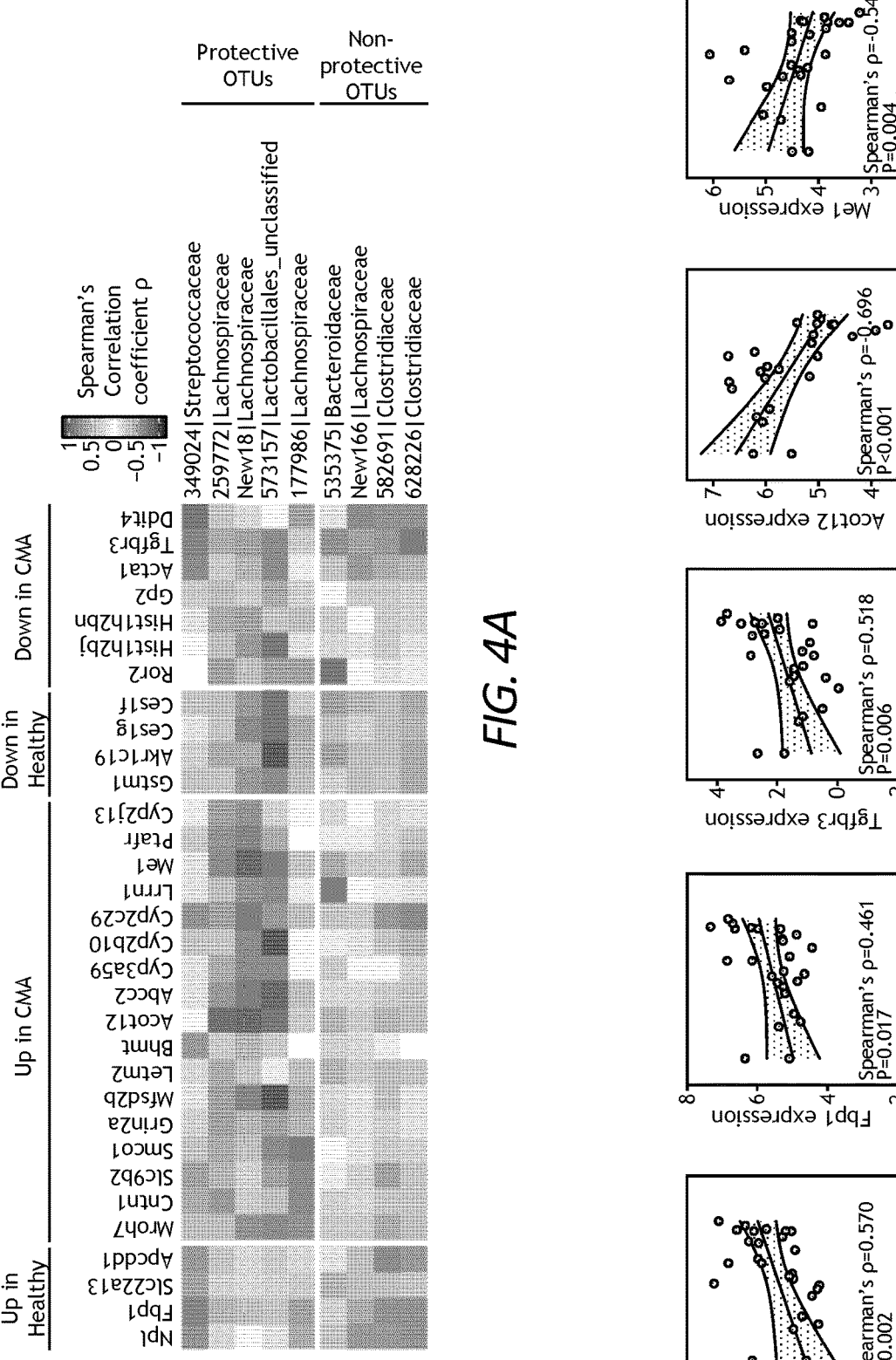

To determine whether the fecal OTU signatures identified in FIG. 2 are also reflective of ileal bacterial populations the inventors examined the correlation between ileal OTUs and the fecal signature in healthy- and CMA-colonized mice (FIG. 12A). It was found that the majority of the taxa change in the same direction (increase or decrease in abundance) in healthy relative to CMA between mouse fecal and ileal samples (FIG. 12B, C). The identification of differential gene expression in ileal IECs from healthy- and CMA-colonized mice (FIG. 3A) suggested that ileal bacteria regulate host immunity to contribute to allergic sensitization. Integrative analysis of ileal bacteria and ileal differentially expressed genes (DEGs) revealed 9 OTUs significantly and consistently correlated with genes upregulated in the ileum of healthy- or CMA-colonized mice (FIG. 4A). Interestingly, ⅗ of the protective OTUs associated with DEGs upregulated in the ileum of healthy colonized mice are members of the family Lachnospiraceae. A BLAST search of assembled 16S sequences against the NCBI database (16S ribosomal RNA, Bacteria and Archaea) revealed that all three protective Lachnospiraceae OTUs upregulated in the healthy colonized mice (259772, New 18, 177986) have *Anaerostipes caccae* as the closest matching species. In particular, OTU259772 was annotated with *A. caccae* in a previous study of human infant feces and diet (21). *A. caccae* is non-spore forming, utilizes lactate and acetate and produces butyrate (22, 23). Spearman's correlation between Lachnospiraceae OTU259772 and several highly correlated ileal DEGs of interest (Ror2, Fbp1, Tgfbr3, Acot12 and Me1) from FIG. 3A are depicted in FIG. 4B. Analysis of ileal and fecal samples using quantitative PCR (qPCR) with previously validated species-specific primers (24) provided independent confirmation of the enrichment of *A. caccae* in healthy-colonized mice (FIG. 4C-E and FIG. 13A-C). Abundance of *A. caccae* in ileal samples also correlated with DEGs from ileal IECs (FIG. 14). Of note, two of the highly correlated DEGs (Acot12 and Me1) are involved in pyruvate metabolism. Butyrate is an important energy source for colonic epithelial cells (25). Butyrate drives oxygen consumption by colonocytes through β-oxidation, thereby maintaining a locally hypoxic niche for butyrate-producing obligate anaerobes (26). Under conditions of dysbiosis, colonocytes generate energy via glycolysis, a process that includes production of pyruvate as a key intermediate (27). It is It is tempting to speculate that the negative correlation between the abundance of butyrate-producing *A. caccae* and pyruvate metabolism-related genes in IECs from CMA-colonized mice is reflective of metabolic shifts in ileal epithelial function under conditions of dysbiosis.

It was next examined whether *A. caccae* can mimic the changes in gene expression and protection against anaphylaxis associated with the healthy microbiota by monocolonizing GF mice (see Methods). Some of the genes significantly upregulated in healthy-colonized mice (Fbp1, Tgfbr3) were also significantly upregulated in *A. caccae* monocolonized mice (FIG. 4F) when compared to GF or CMA-colonized mice. Acot12 expression was significantly upregulated in CMA-colonized mice, but not in healthy-colonized or *A. caccae* monocolonized mice (FIG. 4F). BLG plus CT sensitized *A. caccae* monocolonized mice were protected against an anaphylactic response to BLG challenge. As in FIG. 1, CMA colonized mice exhibited a marked drop in core body temperature indicative of anaphylaxis (FIG. 4G). Both the changes in core body temperature and serum concentrations of mMCPT-1 were significantly reduced in *A caccae* monocolonized mice compared to CMA colonized mice (FIG. 4G, J). Antigen specific, Th2 dependent, antibody (serum BLG-specific IgE and IgG1) (FIG. 4H, I) and cytokine responses IL-13 and IL-4 (FIG. 4K, L) were all reduced in *A caccae* monocolonized mice.

The inventors have shown that anaerobic, mucosa-associated bacteria in the Clostridia class have attracted considerable interest because of their reported roles in the maintenance of intestinal homeostasis through induction of regulatory T cells (28, 29), production of immunomodulatory metabolites (30, 31), and regulation of colonization resistance (32). The inventors have shown that such immunomodulatory bacteria are present in the ileum, at the site of food absorption and have demonstrated their role in protection against an anaphylactic response to food. Mechanistic analysis of the Clostridia-associated changes in ileal gene expression described herein is likely to reveal additional pathways critical to the maintenance of tolerance to dietary antigens. The model described in this report does not address whether the allergic state drives dysbiosis (33) or dysbiosis precedes allergy. Indeed, many factors are likely to contribute to the development of food allergies. This data demonstrate that the commensal bacteria play an important role in preventing allergic responses to food and provides proof of concept for the development of microbiome-modulating strategies to prevent or treat this disease.

C. Methods

Gnotobiotic Mouse Husbandry. All mice were bred and housed in the Gnotobiotic Research Animal Facility (GRAF). Mice were maintained in Trexler style flexible film isolator housing units (Class Biologically Clean) with Ancare polycarbonate mouse cages (catalog #N10HT) and Teklad Pine Shavings (7088; sterilized by autoclave) on a 12-hour light/dark cycle at a room temperature of 20-24° C. Mice were provided with autoclaved sterile water, USP grade, at pH 5.2 ad libitum. Bedding was changed weekly; cages of formula fed mice required near daily bedding changes due to leakage of formula from the bottles. All mice were fed Purina Lab Diet® 5K67, stored in a temperature-controlled environment in accordance with The Guide for the Care and Use of Laboratory Animals (8th Edition, 2013). The diet was sterilized by autoclaving at 121° C.×30 minutes. The sterility of the isolators was checked weekly by both cultivation and 16S rRNA analysis of fecal samples by qPCR. Cultivation was in BHI, Nutrient and Sabbaroud Broth at 37° C. aerobic and anaerobic and 42° C. aerobic for 96 hours. All mice are initially screened upon rederivation or receipt for all internal and external parasites, full serology profile and/or PCR, bacteriology, and gross and histologic analysis of major organs through either IDEXX Radil or Charles River Lab using an Axenic Profile Screen. Germ free (GF) C3H/HeN mice were transferred within the facility from T. Golovkina (University of Chicago).

Preparation of human fecal samples. Healthy (non-allergic) fecal samples were obtained from participants in a vaccination program. These subjects were not at risk for atopic disorders and their clinical history was negative for any allergic condition. Infants with CMA were diagnosed at a tertiary pediatric allergy center (Pediatric Allergy Program at the Department of Translational Medical Science of the University of Naples 'Federico II'); for complete patient information see Supplementary Tables 1 and 2. All aspects of this study were conducted in accordance with the Declaration of Helsinki and approved by the Ethics Committee of the University of Naples 'Federico II'. Written informed consent was obtained from the parents/guardians of all children involved in the research. Fresh fecal samples were collected in the clinic in sterile tubes, weighed, mixed with 2 mL LB broth+30% glycerol per 100-500 mg, aliquoted into sterile cryovials and immediately stored at –80° C. Samples were shipped to the University of Chicago on dry ice where they were stored at –80° C. until homogenization. To colonize mice, frozen fecal samples were introduced into an anaerobic chamber and thawed. Thawed feces were mixed with 3 mm borosilicate glass beads in a sterile 50 mL tube with 2.5 mL pre-reduced PBS+0.05% cysteine and vortexed gently to dissociate. The resulting homogenate was filtered through a 100 μm filter. This homogenization and filtration process was repeated three more times and the final filtrate was mixed with an equal volume of 30% glycerol+ 0.05% cysteine. This solution was aliquoted into Balch tubes with rubber stoppers for transport and introduction into the gnotobiotic isolator. The remaining fecal solution was frozen in aliquots at –80° C.

Colonization of germ free mice. All mice were weaned at 3 weeks of age onto a plant-based mouse chow (Purina Lab Diet® 5K67) and colonized at weaning. GF mice received autoclaved sterile water. Both male and female mice were used for all experiments. Each experiment was littermate controlled. All mice were identified by unique 5 digit ear tags. All work was performed in accordance with the Institutional Biosafety and Animal Care and Use Committees. Each human infant donor transfer was maintained in its own flexible film isolator to avoid cross contamination. In all experiments, repository mice were created from human fecal donors by intragastric gavage of GF mice with 500 μL of freshly prepared infant fecal homogenate. These repositories were then used to colonize subsequent experimental mice via mouse to mouse transfer by intragastric gavage of mouse feces. Fecal samples from both repository and experimental mice were examined regularly by 16S rRNA analysis which demonstrated that mouse to mouse transfer from repository to experimental mice by gavage was highly reproducible and stable over time. For colonization of experimental mice, a freshly voided fecal pellet from a repository mouse was homogenized in 1 mL of sterile PBS and 250 μL of this homogenate was used to gavage one recipient mouse. For mice fed infant formula, the drinking water was replaced by formula four hours prior to colonization. Mice colonized with healthy infant feces were given Enfamil® Infant (Mead Johnson Nutrition, Evansville, IN) and CMA-colonized mice were given extensively hydrolyzed casein formula (EHCF), Nutramigen® I (Mead Johnson Nutrition) ad libitum. Both dry and liquid forms of the formulas were utilized. Dry formula was mixed with autoclaved sterile water, USP grade, according to the manufacturer's instructions. All formulas were refreshed daily.

For *Anaerostipes caccae* monocolonized mice, *A. caccae* (DSM-14662, DSMZ) was cultured in an anaerobic chamber (Coy, Model B) in reduced Schaedler's Broth (Remel) overnight at 37° C. to an optical density (OD600) of 1.08. 250 μL (approximately $2.5 \times 10^8$ CFU) was gavaged to GF mice. These mice were monitored for colonization by qPCR with species-specific primers (Supplementary Table 6) and were maintained as living repositories. For colonization of experimental mice, Enfamil® Infant formula (liquid) was added to the drinking water four hours prior to colonization. A freshly voided fecal pellet from a repository mouse was then homogenized in 1 mL of sterile PBS and 250 μL of this homogenate was used to gavage one recipient mouse. Monocolonization with *A. caccae* was confirmed by 16S rRNA-targeted sequencing of fecal samples collected at sacrifice for all experimental mice.

16S rRNA-targeted sequencing. Bacterial DNA was extracted using the Power Soil DNA Isolation Kit (MoBio). 16S rRNA gene amplicon sequencing was performed on an Illumina MiSeq at the Environmental Sample Preparation and Sequencing Facility at Argonne National Laboratory. Procedures described in reference 34 were used to generate 151 bp paired-end reads from the fecal samples with 12 bp barcodes. The V4 region of the 16S rRNA gene was PCR amplified with region-specific primers (515F-806R) that include sequencer adapter sequences used in the Illumina flowcell. The microbiota signature cohort consisting of infant donor fecal samples, and gnotobiotic mouse fecal and ileal samples (n=99) was analyzed by Quantitative Insights into Microbial Ecology (QIIME) (version 1.9) (35). Raw reads were trimmed to remove low quality bases; paired-end 3' overlapping sequences were merged using SeqPrep (found on the world wide web at github.com/jstjohn/SeqPrep). The open reference OTU picking protocol was used at 97% sequence identity against the Greengenes database (August 2013 release) (36). Sequences were aligned with PyNAST (37). Taxonomic assignments were made with the uclust consensus taxonomy assigner (38); predicted chimeric sequences were removed using ChimeraSlayer (v20110519) (found on the world wide web at microbiomeutil.sourceforge.net). Data were rarefied to an even depth of 3,160 reads for the donor and colonized mouse cohort (n=99, consisting of donor fecal samples, mouse fecal samples at 2- and 3-weeks post-colonization, and mouse ileal samples), and 10,050 reads for the mouse cohort shown in FIG. 12C (n=70, consisting of paired fecal and ileal samples from the 35 mice at 1-week post-colonization). Alpha (Shannon index) and beta diversity metrics were compared between CMA and healthy groups using two-sided Mann-Whitney-Wilcoxon test (non-parametric) and PERMANOVA with weighted UniFrac distance in R package vegan (v2.4.5) (39), respectively. Pielou's evenness index J' was computed by $$J' = \frac{H'}{\ln S}$$

where H' is Shannon index and S as the maximum number of OTUs. Discrete False-Discovery Rate (DS-FDR) (40) was used to identify differentially abundant bacterial taxa between fecal communities of the CMA and healthy groups with parameters "transform_type=normdata, method=meandiff, alpha=0.10, numperm=1000, fdr_method=dsfdr" (accessed 02262018) (https://github-.com/biocore/dsFDR). Compared to the Benjamini-Hochberg-FDR (BH-FDR) method, the DS-FDR method has increased power with limited sample size and is robust to sparse data structure (low proportion of non-zero values in microbe abundance table), therefore is uniquely suited for data analysis of microbe communities (40). The DS-FDR algorithm does not compute adjusted P-values; instead, it estimates the false-discovery rate from a permutation test (default 1000 permutations), which controls the FDR at the desired level (0.10). As such, it computes the raw P-values, test statistics and rejected hypotheses in the output (Supplementary Table 3 and Supplementary Table 5). In each comparison, OTUs present in less than 4 samples were removed prior to applying the DS-FDR test. Linear discriminant analysis effect size (LEfSe) was used to identify genera significantly enriched in CMA or healthy groups compared to the other, using the per-sample normalization value of 1,000,000 and default values for other parameters (41). In LEfSe analysis, linear discriminant analysis (LDA) score was computed for taxa differentially abundant between the two groups. A taxon at $P<0.05$ (Kruskal-Wallis test) and log $10(LDA) \geq 2.0$ (or $\leq -2.0$) was considered significant. For FIG. 2A, after differential abundance testing in donor CMA vs healthy comparison using DS-FDR, the inventors further filtered the significant OTUs by requiring presence in at least two mouse groups, leaving a total of 58 OTUs for further analysis. An OTU ratio was calculated by dividing the total number of potentially protective OTUs (more abundant in healthy) by the total number of potentially non-protective OTUs (more abundant in CMA) per sample. In addition, an OTU abundance score was computed taking into consideration the abundance of 58 OTUs identified in CMA relative to healthy donor fecal samples shown in FIG. 2A. First, data transformation was applied on the relative abundance to bring the signal close to Gaussian distribution. The relative abundance of each OTU was multiplied by a constant ($1 \times 10^6$) to bring all values to larger than 1, log 10 transformed, and scaled by dividing the value by their root mean square across samples. The abundance of potentially nonprotective OTUs was multiplied by ($-1$). Next, the sum of the transformed abundance of the 58 OTUs was calculated to generate the aggregate score. To validate the OTU ratio differences in the independent cohort, the inventors reanalyzed the 16S sequencing data of fecal samples collected from the healthy and CMA infants (n=38) in ref 5 using the same analysis protocol described above, with data rarefied to an even depth of 6,424 reads. Among the 58 OTUs shown in FIG. 2A, 55 OTUs were assigned with known reference IDs and 3 with new reference IDs (Supplementary Table 3). The new reference OTU IDs are not comparable between different analysis cohorts, hence the inventors focused on the OTUs with known reference IDs. Out of 55 known OTUs, 52 were matched in the reanalyzed independent cohort and used for calculation of protective/non-protective OTU ratio depicted in FIG. 10.

Food allergen sensitization and challenge. Protocols were adapted from reference 7. All mice were weaned onto a plant-based mouse chow (Purina Lab Diet® 5K67) at 3 weeks of age. GF mice received autoclaved sterile water. For mice colonized with feces from infant donors, or monocolonized with *A. caccae*, the drinking water was replaced by formula four hours prior to colonization. Mice colonized with healthy feces or *A. caccae* received Enfamil®; CMA colonized mice received Nutramigen® (both from Mead Johnson). On day 0, one week post weaning (GF) or colonization (healthy/*A. caccae*/CMA), all mice were fasted for 4 hours and then given a gavage of 200 mM sodium bicarbonate. 30 minutes later, mice were given 20 mg BLG (Sigma) plus 10 µg CT (List Biologicals). This protocol was repeated weekly for 5 weeks. For formula-fed mice, formula was replaced by sterile water for the week after the last sensitization. Prior to challenge on day 42, mice were fasted for 4 hours and given sodium bicarbonate by gavage. Two doses of 100 mg BLG each were then administered via intragastric gavage 30 minutes apart. Core body temperature was measured in a blinded fashion prior to allergen challenge and every 5 minutes after the first challenge until at least 30 minutes after the second challenge using a rectal probe (PhysiTemp). Serum was collected 1 hour after the second challenge to measure mMCPT-1 levels. Serum was collected 24 hours after challenge for antibody measurements.

ELISAs. mMCPT-1 was quantified in serum collected 1 hour after the second challenge according to the manufacturer's protocol (eBioscience). BLG-specific ELISAs were performed using protocols modified from reference 7. Briefly, plates were coated overnight at 4° C. with 100 µg/mL BLG in 100 mM carbonate-bicarbonate buffer (pH 9.6). Plates were blocked for 2 hours at room temperature with 3% BSA. Samples were added in 1% BSA and incubated overnight at 4° C. Assays were standardized with BLG-specific antibodies (IgE or IgG1) purified on a CNBr-Sepharose affinity column from mice immunized with BLG+alum (42). BLG-specific antibodies were detected with goat anti-mouse IgE-UNLB (Southern Biotech) and rabbit anti-goat IgG-AP (ThermoFisher) then developed with p-NPP (KPL Labs) or IgG1-HRP (Southern Biotech) and developed with TMB (Sigma).

For cytokine analysis spleens were harvested 24 h post challenge from *A. caccae* or CMA colonized mice sensitized with BLG+CT for 5 weeks. Splenocytes were stimulated at a concentration of $2 \times 10^6$ cells/ml at 37° C., 10% $CO_2$ with 10 mg/ml BLG (Sigma) in cDMEM (with 4% FCS (Hy-Clone), 10 mM HEPES (Gibco), 100 U/ml Penicillin/Streptomycin (Gibco) and 55 µM 2-mercaptoethanol (Gibco). Cytokine concentrations in 72 hr culture supernatants were determined by ELISA for IL-13 and IL-4 (both from Invitrogen).

Epithelial cell isolation. As in sensitization experiments, mice were weaned at 3 weeks of age and placed on infant formula prior to colonization. Seven days after colonization, mice were euthanized and ileum was removed. For IEC isolation, tissues were cleaned and inverted as described in ref (43). IECs were collected by inflating inverted tissue in Cell Recovery Solution (Corning) every 5 minutes for 30 minutes. IEC samples were lysed in TRIZol (ThermoFisher) and RNA was extracted with PureLink RNA Mini Kit (Ambion) plus on-column DNAse treatment (PureLink DNAse Set, Ambion).

RNASeq. RNA libraries were prepared using TruSeq Stranded Total Library Preparation Kit with Ribo-Zero human/mouse/rat (Illumina). Samples were sequenced at the University of Chicago Functional Genomics Core, using 50 bp single reads chemistry in a HiSeq2500 instrument, with sequencing replicates in two lanes. The quality of raw reads was assessed by FastQC (v0.11.5) (44). The QC30 score across 39 RNAseq samples was 96.81%±0.06% (mean±s.e.m), which represents the percentage of bases with quality score ≥Q30. Alignment to the mouse reference transcriptome was performed with Gencode gene annotation (vM16, GRCm38) by Kallisto (v0.43.1) with the strand-specific mode (45). This mode implements a kmer-based pseudoalignment algorithm to accurately quantify transcripts from RNASeq data while robustly detecting errors in the reads. The average mapping rate was 62.77%±1.10% (mean±S.E.M) based on the Kallisto pseudoalignments to the reference transcriptome. On average, 35 million raw sequencing reads were generated per sample, and 22 million were mapped to transcriptome using Kallisto. Transcript-level abundance was quantified specifying strand-specific protocol, summarized into gene level using tximport (v1.4.0) (46), normalized by trimmed mean of M values (TMM) method, and log 2-transformed. Genes expressed in at least 3 samples (counts per million of reads (CPM)>3) were kept for further analysis. Genes differentially expressed between groups were identified using limma voom algorithm with precision weights (v3.34.5) (47). duplicateCorrelation function was used to estimate the correlation among mouse samples with Donor (1 to 8) as the blocking factor. 1mFit function was used to fit all mouse samples (n=39, 18 CMA-colonized, 18 healthy-colonized, and 3 GF) into one linear model incorporating the correlation structure computed from above. Contrasts were set as CMA versus healthy, CMA versus GF and healthy versus GF to identify DEGs in each comparison. Genes that are significantly differentially expressed between CMA and healthy, and also different from GF mice were identified using a two-step procedure: (1) Genes were detected as different in CMA vs healthy comparison with fold change ≥1.5 or ≤−1.5 at false-discovery rate (FDR) corrected p-value smaller than 0.10; (2) Genes from step (1) were further filtered by fold change ≥1.5 or ≤−1.5 in CMA vs GF or healthy vs GF comparison at FDR 0.05. A more stringent FDR threshold (0.05) was applied in step (2) to prioritize potentially true positives when compared to the negative control (GF). Multiple testing correction was performed using Benjamini-Hochberg FDR (BH-FDR) method (48). A total of 32 DEGs passed these thresholds, which represent four types of gene expression changes in colonized mice: (1) Up in healthy: genes that are up-regulated in healthy mice relative to both CMA and GF; (2) Up in CMA: genes that are up-regulated in CMA mice relative to both healthy and GF; (3) Down in healthy: genes that are down-regulated in healthy mice relative to both CMA and GF; and (4) Down in CMA: genes that are down-regulated in CMA mice relative to healthy and GF. The four groups of DEGs are shown in FIGS. 3A and 4A. Gene Ontology and KEGG pathways significantly enriched in the 32 DEGs of interest were identified using clusterprofiler (v3.6.0) (49) at false-discovery rate (FDR) corrected p-value smaller than 0.10 (BH-FDR method, hypergeometric test). The DEGs were split into two groups for this analysis; (1) Healthy included all genes that were Up in healthy and Down in CMA and (2) CMA included all genes that were Up in CMA and Down in Healthy. Correlation between DEGs and ileal OTUs significantly differentially abundant between CMA and healthy samples were computed using Spearman's rank correlation method, followed by applying filters to (1) keep the OTUs that show significant correlation with at least 1 DEG from the designated group at P<0.05. For potentially protective OTUs (more abundant in healthy), they are correlated with genes from group "Up in healthy" or "Down in healthy"; for potentially non-protective OTUs (more abundant in CMA), they are correlated with genes from group "Up in CMA" or "Down in CMA"; (2) keep the OTUs that show relatively consistent trend of positive correlation (Spearman's ρ>0.20) across at least 60% of the DEGs from the designated group. For potentially protective OTUs, they are correlated with genes from group "Up in healthy" and "Down in CMA" joined; for potentially non-protective OTUs, they are correlated with genes from group "Up in CMA" and "Down in healthy" joined; (3) keep OTUs present in at least 3 CMA and 3 healthy mice. 9 ileal OTUs passed these correlation filters and are shown in FIG. 4A. Correlation between the relative abundance of OTUs and gene expression were calculated using Spearman's correlation method with samples that are above the limit of detection for the assay.

qPCR. Gene expression was measured by qPCR as described in reference 7. In brief, cDNA was prepared from RNA using the iScript cDNA Synthesis kit (BioRad). Gene expression was measured with PowerUp SYBR green master mix (Applied Biosystems) according to the manufacturer's instructions. Primers are listed in Supplementary Table 7 (20, 50-54). Expression of genes of interest was normalized to Hprt. Relative expression was measured using ΔΔCt centered around the geometric mean; GF mice were used as a reference.

The presence of *A. caccae* in fecal and ileal samples was confirmed using qPCR as described in ref (25). Bacterial DNA was extracted using the Power Soil DNA Isolation Kit (MoBio) and qPCR was performed using PowerUp SYBR green master mix (Applied Biosystems) using 4 µl of each primer at 10 µM working dilution and 2 µl of bacterial DNA. Primers are listed in Supplementary Table 6. The cycling conditions for the reaction consisted of an activation cycle of 50° C. for 2 min followed by one cycle of 95° C. for 10 min and 40 cycles at 94° C. for 20 sec, 55° C. for 20 sec and 72° C. for 50 sec. The fluorescent probe was detected in the last step of this cycle. A melt curve was performed at the end of the PCR to confirm specificity of PCR product. Relative abundance is expressed as $2^{-Ct}$ normalized to total 16S rRNA copies per g fecal material and multiplied by a constant ($1\times10^{25}$) to bring all values above 1.

Histopathologic analysis. For histological analysis 3 mm pieces of mid-colon and mid-ileum tissue were fixed in either 10% formalin for H&E staining or Carnoy's fixative for Periodic-acid Schiff (PAS) staining. Sectioning and staining were performed by the Human Tissue Resource Center at the University of Chicago. All sections were reviewed by a GI pathologist in a blinded fashion.

Statistical analysis. Prism 7.0 (GraphPad) was used to perform one-way (FIG. 4F) ANOVA with Bonferroni correction for multiple comparisons and two-sided Student's t-test (FIG. 4D and FIG. 13B), as indicated in the figure legends. DS-FDR method was used to identify significant OTUs (FIG. 2A, FIG. 4C and FIG. 13A) comparing CMA to healthy group. BH-FDR method was used for multiple testing correction in RNA-Seq analysis (FIG. 3A) and GO enrichment analysis (FIG. 3B). Shannon Diversity and Pielou's Evenness were compared using a two-sided non-parametric Mann-Whitney-Wilcoxon test (FIG. 7A, B). Analysis of protective/non-protective OTU ratio in the larger, independent cohort of infants was performed using two-sided Mann-Whitney-Wilcoxon test (FIG. 11). The biological responses of different donor colonized mice to sensitization with BLG (FIG. 1A-D, FIG. 4G, FIG. 8A, FIG. 9A) were explored with linear mixed-effect models (55) based on restricted maximum likelihood (REML) in R (lmerTest v3.0.1) (56). Group (GF, healthy and CMA in FIG. 1A; *A. caccae* and CMA in FIG. 4G; healthy BFD and CMA BFD in FIG. 8A; H₂O and Enfamil® in FIG. 9A) temperature changes across time (both linear and quadratic) were modeled as Temperature Group+Time*Group+ Time*Time*Group with random intercepts and slopes estimated for individual mice. Contrasts of group temperature trends were performed using t-tests with the Benjamini-Hochberg FDR (BH-FDR) adjustment for multiple comparisons. To control for cases where groups contained multiple donors (FIG. 1A), the previous model was updated to include mice nested within each donor as a random effect and repeated the contrasts. Since the results of the two models were concordant, the results from the first model is reported for consistency of methods. For FIG. 1B-D, antibody concentrations were log transformed and modeled as log(Concentration) Group with donors as a random effect. Contrasts for group differences were performed using the previously mentioned methods. For FIG. 4H-I, FIG. 8B-D, FIG. 9B-D, antibody and cytokine concentrations were log transformed and compared using t-tests. The data analysis commands (including the data files and R markdown files for reproducibility) are available from the authors upon request.

D. Tables

Supplementary TABLE 1

| | Healthy | | | | CMA | | | |
|---|---|---|---|---|---|---|---|---|
| Donor ID # | 1 | 2 | 3 | 4 | 5 | 6 | 7 | 8 |
| Sex | Male | Male | Male | Male | Male | Male | Male | Male |
| Mode of Delivery | Cesarean section | Cesarean section | Cesarean section | Cesarean section | Cesarean section | Cesarean section | Cesarean section | Cesarean section |
| Gestational Age | At term | At term | At term | At term | At term | At term | At term | At term |
| Breast-feeding | <14 days | <14 days | <14 days | <14 days | <14 days | <14 days | <14 days | <14 days |
| Age at stool collection | 6 months | 6 months | 6 months | 6 months | 6 months | 6 months | 6 months | 6 months |
| Age at CMA symptoms onset | — | — | — | — | 2 months 12 days | 2 months | 6 months | 5 months 20 days |
| Symptoms at CMA diagnosis | — | — | — | — | Urticaria and vomiting | Urticaria and vomiting | Eczema, urticaria, vomiting | Eczema, vomiting |
| IgE-mediated mechanism | — | — | — | — | Yes | Yes | Yes | Yes |
| Skin prick test value at diagnosis (mm) | | | | | | | | |
| Alphalacto-albumin | — | — | — | — | 5 | 12 | 10 | 4 |
| Betalacto-globulin | — | — | — | — | 3 | 3 | 1 | 10 |
| Casein | — | — | — | — | 3 | 5 | 4 | 8 |
| Whole milk | — | — | — | — | 7 | 6 | 5 | 7 |
| Total serum IgE at diagnosis (kU/L) | — | — | — | — | 340 | 127 | 267 | 358 |

Supplementary Table 2
Patient data for breast-fed infant donors in Supplementary Figure 4

| Description | Healthy infant | Infant with cow's milk allergy |
|---|---|---|
| Donor ID # | 9 | 10 |
| Sex | Female | Female |
| Mode of Delivery | Spontaneous | Spontaneous |
| Gestational Age | At term | At term |
| Breastfeeding | Yes (mother consuming cow's milk protein) | Yes (mother consuming cow's milk protein) |
| Age at stool collection | 6 months | 6 months |
| Age at CMA symptoms onset | | 5 months |
| Symptoms at CMA diagnosis | | Eczema, irritability, vomiting, failure to thrive, diarrhea |
| IgE-mediated mechanism | | Yes |
| Skin prick test value at diagnosis (mm) | | |
| Alphalactoalbumin | — | 15 |
| Betalactoglobulin | — | 1 |
| Casein | — | 7 |
| Whole milk | — | 15 |

-continued

Supplementary Table 2
Patient data for breast-fed infant donors in Supplementary Figure
4

| Description | Healthy infant | Infant with cow's milk allergy |
|---|---|---|
| Total serum IgE at diagnosis (kU/L) | | 334 |

Supplementary Table 3
58 OTUs differentially abundant between CMA- and healthy-donor
fecal samples, shown in FIG. 2a.

| OTU | Change In Direction | DS-FDR Reject | DS-FDR Test Statistic | DS-FDR Raw Pvalues | Taxonomy |
|---|---|---|---|---|---|
| 1111294 | UP in Healthy | TRUE | −0.184530795 | 0.015984016 | k__Bacteria; p__Proteobacteria: c__Gammaproteobacteria; o__Enterobacteriales; f__Enterobacteriaceae; g__; s__ |
| 360015 | UP in Healthy | TRUE | −0.068956969 | 0.001998002 | k__Bacteria; p__Firmicutes; c__Clostridia; o__Clostridiales; f__Lachnospiraceae; g__[Ruminococcus]; s__gnavus |
| New.Reference OTU147 | UP in Healthy | TRUE | −0.039674728 | 0.000999001 | k__Bacteria; p__Firmicutes; c__Clostridia; o__Clostridiales; f__Clostridiaceae; g__; s__ |
| 628226 | UP in Healthy | TRUE | −0.034540622 | 0.000999001 | k__Bacteria; p__Firmicutes; c__Clostridia; o__Clostridiales; f__Clostridiaceae; g__; s__ |
| 349024 | UP in Healthy | TRUE | −0.01594088 | 0.013986014 | k__Bacteria; p__Firmicutes; c__Bacilli; o__Lactobacillales; f__Streptococcaceae; g__Streptococcus; s__ |
| 712677 | UP in Healthy | TRUE | −0.012704055 | 0.027972028 | k__Bacteria; p__Firmicutes; c__Clostridia; o__Clostridiales |
| 780650 | UP in Healthy | TRUE | −0.010383613 | 0.012987013 | k__Bacteria; p__Firmicutes; c__Clostridia; o__Clostridiales; f__Clostridiaceae; g__; s__ |
| 843459 | UP in Healthy | TRUE | −0.009899159 | 0.002997003 | k__Bacteria; p__Firmicutes; c__Clostridia; o__Clostridiales; f__Clostridiaceae; g__; s__ |
| 262095 | UP in Healthy | TRUE | −0.007552857 | 0.01998002 | k__Bacteria; p__Firmicutes; c__Erysipelotrichi; o__Erysipelotrichales; f__Erysipelotrichaceae; g__; s__ |
| New.Reference OTU166 | UP in Healthy | TRUE | −0.005328787 | 0.006993007 | k__Bacteria; p__Firmicutes; c__Clostridia; o__Clostridiales; f__Lachnospiraceae |
| 579851 | UP in Healthy | TRUE | −0.005308631 | 0.022977023 | k__Bacteria; p__Firmicutes; c__Erysipelotrichi; o__Erysipelotrichales; f__Erysipelotrichaceae; g__[Eubacterium]; s__dolichum |

-continued

Supplementary Table 3
58 OTUs differentially abundant between CMA- and healthy-donor
fecal samples, shown in FIG. 2a.

| OTU | Change In Direction | DS-FDR Reject | DS-FDR Test Statistic | DS-FDR Raw Pvalues | Taxonomy |
|---|---|---|---|---|---|
| 551822 | UP in Healthy | TRUE | −0.005216137 | 0.026973027 | k__Bacteria; p__Firmicutes; c__Clostridia; o__Clostridiales; f__Clostridiaceae |
| 298247 | UP in Healthy | TRUE | −0.004133646 | 0.000999001 | k__Bacteria; p__Firmicutes; c__Clostridia; o__Clostridiales; f__Lachnospiraceae; g__Epulopiscium; s |
| 345540 | UP in Healthy | TRUE | −0.003450891 | 0.000999001 | k__Bacteria; p__Protcobactcria: c__Gammaproteobacteria; o__Enterobacteriale s; f__Enterobacteriaceae; g__; s__ |
| 582691 | UP in Healthy | TRUE | −0.002271895 | 0.004995005 | k__Bacteria; p__Firmicutes; c__Clostridia; o__Clostridiales; f__Clostridiaceae; g__; s__ |
| 259772 | UP in Healthy | TRUE | −0.002219727 | 0.016983017 | k__Bacteria; p__Firmicutes; c__Clostridia; o__Clostridiales; f__Lachnospiraceae; g__Coprococcus; s__ |
| 325419 | UP in Healthy | TRUE | −0.001426612 | 0.000999001 | k__Bacteria; p__Firmicutes; c__Clostridia; o__Clostridiales; f__Clostridiaceae; g__; s__ |
| 797229 | UP in Healthy | TRUE | −0.001367202 | 0.000999001 | k__Bacteria; p__Protcobactcria: c__Gammaproteobacteria; o__Enterobacteriale s; f__Enterobacteriaceae; g__; s__ |
| 557627 | UP in Healthy | TRUE | −0.000748282 | 0.000999001 | k__Bacteria; p__Firmicutes; c__Clostridia; o__Clostridiales; f__Clostridiaceae; g__; s__ |
| 828483 | UP in Healthy | TRUE | −0.000737522 | 0.020979021 | k__Bacteria; p__Firmicutes; c__Clostridia; o__Clostridiales; f__Clostridiaceae; g__Clostridium |
| 299267 | UP in Healthy | TRUE | −0.000617653 | 0.026973027 | k__Bacteria; p__Protcobactcria: c__Gammaproteobacteria; o__Enterobacteriale s; f__Enterobacteriaceae; g__; s__ |
| 4448331 | UP in Healthy | TRUE | −0.000531974 | 0.030969031 | k__Bacteria; p__Proteobacteria; c__Gammaproteobacteria; o__Enterobacteriale s; f__Enterobacteriaceae; g__; s__ |
| 3376513 | UP in Healthy | TRUE | −0.000490385 | 0.024975025 | k__Bacteria; p__Firmicutes; c__Clostridia; o__Clostridiales; f__Lachnospiraceae; g__[Ruminococcus]; s__gnavus |
| 813217 | UP in Healthy | TRUE | −0.000418414 | 0.004995005 | k__Bacteria; p__Protcobactcria: c__Gammaproteobacteria; o__Enterobacteriale s__; f__Enterobacteriaceae; g__; s__ |

-continued

Supplementary Table 3
58 OTUs differentially abundant between CMA- and healthy-donor
fecal samples, shown in FIG. 2a.

| OTU | Change In Direction | DS-FDR Reject | DS-FDR Test Statistic | DS-FDR Raw Pvalues | Taxonomy |
|---|---|---|---|---|---|
| New.CleanUp.Reference OTU56927 | UP in Healthy | TRUE | −0.000411459 | 0.001998002 | k__Bacteria; p__Firmicutes; c__Clostridia; o__Clostridiales; f__Lachnospiraceae; g__[Ruminococcus]; s__gnavus |
| 335701 | UP in Healthy | TRUE | −0.000408096 | 0.032967033 | k__Bacteria; p__Firmicutes; c__Clostridia; o__Clostridiales; f__Lachnospiraceae; g__[Ruminococcus]; s__gnavus |
| 191999 | UP in Healthy | TRUE | −0.000393548 | 0.008991009 | k__Bacteria; p__Firmicutes; c__Clostridia; o__Clostridiales; f__Lachnospiraceae |
| 183865 | UP in Healthy | TRUE | −0.00036463 | 0.014985015 | k__Bacteria; p__Firmicutes; c__Clostridia; o__Clostridiales; f__Lachnospiraceae; g__ [Ruminococcus]; s__gnavus |
| 231787 | UP in Healthy | TRUE | −0.000362215 | 0.003996004 | k__Bacteria; p__Protcobactcria: c__Gammaproteobacteria; o__Enterobacteriale s__; f__Enterobacteriaceae; g__; s __ |
| 342397 | UP in Healthy | TRUE | −0.000334965 | 0.006993007 | k__Bacteria; p__Firmicutes; c__Clostridia; o__Clostridiales; f__Lachnospiraceae; g__[Ruminococcus]; s__gnavus |
| 581782 | UP in Healthy | TRUE | −0.000327138 | 0.012987013 | k__Bacteria; p__Protcobactcria: c__Gammaproteobacteria; o__Enterobacteriales; f__Enterobacteriaceae; g__; s__ |
| 304641 | UP in Healthy | TRUE | −0.000299547 | 0.014985015 | k__Bacteria; p__Protcobactcria: c__Gammaproteobacteria; o__Enterobacteriale s; f__Enterobacteriaceae; g__; s__ |
| 4389289 | UP in Healthy | TRUE | −0.000274745 | 0.032967033 | k__Bacteria; p__Protcobactcria: c__Gammaproteobacteria; o__Enterobacteriale s; f__Enterobacteriaceae; g__; s__ |
| 541119 | UP in Healthy | TRUE | −0.000220503 | 0.032967033 | k__Bacteria; p__Protcobactcria: c__Gammaproteobacteria; __Enterobacteriale s; f__Enterobacteriaceae; g__; s__ |
| 195258 | UP in CMA | TRUE | 0.000463044 | 0.000999001 | k__Bacteria; p__Bacteroidetes; c__Bacteroidia; o__Bacteroidales; f__Bacteroidaceae; g __Bacteroides; s__ovatus |

-continued

Supplementary Table 3
58 OTUs differentially abundant between CMA- and healthy-donor
fecal samples, shown in FIG. 2a.

| OTU | Change In Direction | DS-FDR Reject | DS-FDR Test Statistic | DS-FDR Raw Pvalues | Taxonomy |
|---|---|---|---|---|---|
| 315846 | UP in CMA | TRUE | 0.0009126 | 0.012987013 | k__Bacteria; p__Bacteroidetes; c__Bacteroidia; o__Bacteroidales; f__[Bamesiellaceael; g__; s__ |
| 551902 | UP in CMA | TRUE | 0.001063128 | 0.002997003 | k__Bacteria; p__Firmicutes; c__Clostridia; o__Clostridiales; f__Ruminococcaceae; g__; s__ |
| 318190 | UP in CMA | TRUE | 0.001133533 | 0.002997003 | k__Bacteria; p__Firmicutes; c__Clostridia; o__Clostridiales; f__Ruminococcaceae; g__; s__ |
| 591635 | UP in CMA | TRUE | 0.001212852 | 0.004995005 | k__Bacteria; p__Firmicutes; c__Clostridia; o__Clostridiales; f__Ruminococcaceae; g__Ruminococcus; s__ |
| 585227 | UP in CMA | TRUE | 0.001492734 | 0.022977023 | k__Bacteria; p__Firmicutes; c__Clostridia; o__Clostridiales; f__Ruminococcaceae; g__Oscillospira; s__ |
| 370225 | UP in CMA | TRUE | 0.001699313 | 0.008991009 | k__Bacteria; p__Actinobactcria; c__Actinobacteria; o__Bifidobacteriales; f__Bifidobacteriaceae; g__Bifidobacterium; s__adolescentis |
| 199354 | UP in CMA | TRUE | 0.003134517 | 0.012987013 | k__Bacteria; p__Bacteroidetes; c__Bacteroidia; o__Bacteroidales; f__ [Bamesiellaceael; g__; s__ |
| 198866 | UP in CMA | TRUE | 0.003516506 | 0.002997003 | k__Bacteria; p__Bacteroidetes; c__Bacteroidia; o__Bacteroidales; f__Porphyromonadaceae; g__Parabacteroides; s__ |
| 583398 | UP in CMA | TRUE | 0.003665419 | 0.000999001 | k__Bacteria; p__Firmicutes; c__Clostridia; o__Clostridiales; f__Lachnospiraceae; g__ [Ruminococcusl; s__ |
| 583656 | UP in CMA | TRUE | 0.003887232 | 0.000999001 | k__Bacteria; p__Bacteroidetes; c__Bacteroidia; o__Bacteroidales; f__Bacteroidaceae; g__Bacteroides; s__ |
| 535375 | UP in CMA | TRUE | 0.004373572 | 0.000999001 | k__Bacteria; p__Bacteroidetes; c__Bacteroidia; o__Bacteroidales; f__Bacteroidaceae; g__Bacteroides; s__ |
| 1111191 | UP in CMA | TRUE | 0.004749497 | 0.021978022 | k__Bacteria; p__Firmicutes; c__Clostridia; o__Clostridiales; |

-continued

Supplementary Table 3
58 OTUs differentially abundant between CMA- and healthy-donor
fecal samples, shown in FIG. 2a.

| OTU | Change In Direction | DS-FDR Reject | DS-FDR Test Statistic | DS-FDR Raw Pvalues | Taxonomy |
|-----|---------------------|---------------|----------------------|---------------------|----------|
| | | | | | f_Lachnospiraceae; g_[Ruminococcus]; s_gnavus |
| 580629 | UP in CMA | TRUE | 0.005200626 | 0.017982018 | k_Bacteria; p_Bacteroidetes; c_Bacteroidia; o_Bacteroidales; f_Bacteroidaceae; g_Bacteroides; s_ |
| 365181 | UP in CMA | TRUE | 0.00614329 | 0.000999001 | k_Bacteria; p_Actinobacteria: c_Coriobacteriia; o_Coriobacteriales; f_Coriobacteriaceae; g_Collinsella; s_aerofaciens |
| 359809 | UP in CMA | TRUE | 0.007206031 | 0.006993007 | k_Bacteria; p_Protcobactcria: c_Betaproteobacteria; o_Burkholderiales; f_Alcaligcnaccac: g_Sutterella; s_ |
| 585914 | UP in CMA | TRUE | 0.007841977 | 0.001998002 | k_Bacteria; p_Bacteroidetes; c_Bacteroidia; o_Bacteroidales; f_Porphyromonadaceae; g_Parabacteroides; s_distasonis |
| 365385 | UP in CMA | TRUE | 0.009299774 | 0.014985015 | k_Bacteria; p_Actinobactcria: c_Actinobactcria: o_Bifidobacteriales; f_Bifidobacteriaceae; g_Bifidobacterium; s_ |
| 583117 | UP in CMA | TRUE | 0.009878272 | 0.000999001 | k_Bacteria; p_Bacteroidetes; c_Bacteroidia; o_Bacteroidales; f_Bacteroidaceae; g_Bacteroides; s_ |
| 180082 | UP in CMA | TRUE | 0.011856764 | 0.002997003 | k_Bacteria; p_Bacteroidetes; c_Bacteroidia; o_Bacteroidales; f_Porphyromonadaceae; g_Parabacteroides; s_ |
| 589071 | UP in CMA | TRUE | 0.016312063 | 0.002997003 | k_Bacteria; p_Bacteroidetes; c_Bacteroidia; o_Bacteroidales; f_Bacteroidaceae; g_Bacteroides; s_uniformis |
| 514272 | UP in CMA | TRUE | 0.029745704 | 0.011988012 | k_Bacteria; p_Firmicutes; c_Clostridia; o_Clostridiales; f_Lachnospiraceae; g_; s_ |
| 484304 | UP in CMA | TRUE | 0.030173538 | 0.004995005 | k_Bacteria; p_Actinobactcria: c_Actinobactcria: o_Bifidobacteriales; f_Bifidobacteriaceae; g_Bifidobacterium; s_ |
| 589277 | UP in CMA | TRUE | 0.052225784 | 0.001998002 | k_Bacteria; p_Bacteroidetes; c_Bacteroidia; o_Bacteroidales; |

-continued

Supplementary Table 3
58 OTUs differentially abundant between CMA- and healthy-donor
fecal samples, shown in FIG. 2a.

| OTU | Change In Direction | DS-FDR Reject | DS-FDR Test Statistic | DS-FDR Raw Pvalues | Taxonomy |
|---|---|---|---|---|---|
| | | | | | f_Bacteroidaceae; g_Bacteroides; s_ |

Supplementary TABLE 4

32 genes differentially expressed in CMA- and healthy-colonized mouse ileal
RNAseq samples, and different from negative control (GF mice), shown in FIG. 3a.

| | | RNAseq | | CMA versus Healthy | | CMA versus GF |
|---|---|---|---|---|---|---|
| Gene | EnsemblGeneID | Average Expression | DEG Group | FDR-adjusted P value | Fold Change | Direction of Change |
| Slc22a13 | ENSMUSG00000074028 | 2.778111515 | UP in Healthy | 0.029753823 | −2.401525743 | NE |
| Fbp1 | ENSMUSG00000069805 | 5.555254563 | UP in Healthy | 8.17E−05 | −2.063132823 | ND |
| Apcdd1 | ENSMUSG00000071847 | 1.494018834 | UP in Healthy | 0.049270498 | −1.609221514 | NE |
| Npl | ENSMUSG00000042684 | 5.041978196 | UP in Healthy | 0.085368856 | −1.559896139 | NE |
| Abcc2 | ENSMUSG00000025194 | 9.209485113 | UP in CMA | 0.010848769 | 1.505881058 | UP in CMA |
| Bhmt | ENSMUSG00000074768 | 1.082085196 | UP in CMA | 0.071649815 | 1.509332678 | UP in CMA |
| Mfsd2b | ENSMUSG00000037336 | 1.777883345 | UP in CMA | 0.061865715 | 1.537225758 | UP in CMA |
| Cyp3a59 | ENSMUSG00000061292 | 2.136791204 | UP in CMA | 0.027389658 | 1.549562876 | UP in CMA |
| Lrrn1 | ENSMUSG00000034648 | 1.595303389 | UP in CMA | 0.013681852 | 1.581394892 | UP in CMA |
| Slc9b2 | ENSMUSG00000037994 | 1.102430337 | UP in CMA | 0.085368856 | 1.605005893 | UP in CMA |
| Mroh7 | ENSMUSG00000047502 | 3.89754756 | UP in CMA | 0.021327414 | 1.617161783 | UP in CMA |
| Grin2a | ENSMUSG00000059003 | 2.458692024 | UP in CMA | 0.085653544 | 1.617995585 | UP in CMA |
| Cntn1 | ENSMUSG00000055022 | 1.148935328 | UP in CMA | 0.014593455 | 1.651618302 | UP in CMA |
| Letm2 | ENSMUSG00000037363 | 1.650075654 | UP in CMA | 0.018797255 | 1.66583385 | UP in CMA |
| Ptafr | ENSMUSG00000056529 | 1.301260118 | UP in CMA | 0.073471735 | 1.694815563 | UP in CMA |
| Me1 | ENSMUSG00000032418 | 4.3922554 | UP in CMA | 0.016384547 | 1.703263564 | UP in CMA |
| Smco1 | ENSMUSG00000046345 | 1.23463105 | UP in CMA | 0.090599686 | 1.755629553 | UP in CMA |
| Cyp2b10 | ENSMUSG00000030483 | 7.581089071 | UP in CMA | 0.029753823 | 1.757005744 | UP in CMA |
| Cyp2j13 | ENSMUSG00000028571 | 4.136663388 | UP in CMA | 0.053930421 | 1.800872438 | UP in CMA |
| Acot12 | ENSMUSG00000021620 | 5.494716849 | UP in CMA | 5.48E−05 | 2.01501538 | UP in CMA |
| Cyp2c29 | ENSMUSG00000003053 | 2.680142327 | UP in CMA | 8.17E−05 | 4.735853239 | UP in CMA |
| Akr1c19 | ENSMUSG00000071551 | 6.653987069 | DOWN in Healthy | 0.007181957 | 1.539241268 | NE |
| Gstm1 | ENSMUSG00000058135 | 3.552920591 | DOWN in Healthy | 0.010848769 | 1.592387077 | NE |
| Ces1f | ENSMUSG00000031725 | 6.194279856 | DOWN in Healthy | 0.027389658 | 1.893583214 | NE |
| Ces1g | ENSMUSG00000057074 | 2.742386148 | DOWN in Healthy | 0.090559257 | 1.907760384 | ND |
| Tgfbr3 | ENSMUSG00000029287 | 1.883866476 | DOWN in CMA | 0.000408545 | −2.74659932 | DOWN in CMA |
| Acta1 | ENSMUSG00000031972 | 1.201617812 | DOWN in CMA | 0.027389658 | −2.50720332 | DOWN in CMA |
| Hist1h2bj | ENSMUSG00000069300 | 1.79373615 | DOWN in CMA | 0.072249982 | −1.935238841 | DOWN in CMA |

Supplementary TABLE 4-continued 32 genes differentially expressed in CMA- and healthy-colonized mouse ileal
RNAseq samples, and different from negative control (GF mice), shown in FIG. 3a.

| Gp2 | ENSMUSG00000030954 | 0.806917328 | DOWN in CMA | 0.070122494 | −1.870775326 | DOWN in CMA |
| Ddit4 | ENSMUSG00000020108 | 3.745786556 | DOWN in CMA | 0.070340591 | −1.576061582 | DOWN in CMA |
| Hist1h2bn | ENSMUSG00000095217 | 3.070162335 | DOWN in CMA | 0.08015986 | −1.565406563 | DOWN in CMA |
| Ror2 | ENSMUSG00000021464 | 2.322930094 | DOWN in CMA | 0.03422688 | −1.545471585 | DOWN in CMA |

| | CMA versus GF | | Healthy versus GF | | |
| Gene | FDR-adjusted P value | Fold Change | Direction of Change | FDR-adjusted P value | Fold Change |
|---|---|---|---|---|---|
| Slc22a13 | 0.063113496 | 3.40496861 | UP in Healthy | 0.005425032 | 8.17711977 |
| Fbp1 | 0.000581517 | 2.373595096 | UP in Healthy | 2.38E−07 | 4.897041951 |
| Apcdd1 | 0.435864462 | 1.265635652 | UP in Healthy | 0.025785895 | 2.03668812 |
| Npl | 0.293803914 | 1.388291017 | UP in Healthy | 0.024969934 | 2.165589797 |
| Abcc2 | 2.04E−05 | 2.175407835 | ND | 0.042313216 | 1.444608007 |
| Bhmt | 0.010731326 | 1.975422585 | NE | 0.410644089 | 1.308805284 |
| Mfsd2b | 0.000867035 | 2.82533517 | NE | 0.075749268 | 1.837944202 |
| Cyp3a59 | 3.05E−05 | 3.39446921 | ND | 0.009662128 | 2.190597918 |
| Lrrn1 | 0.007383553 | 1.714726833 | NE | 0.777501394 | 1.084312869 |
| Slc9b2 | 0.031991401 | 2.02570437 | NE | 0.591859824 | 1.262116469 |
| Mroh7 | 2.72E−03 | 2.033697925 | NE | 0.42241223 | 1.257572339 |
| Grin2a | 0.044336212 | 1.964067568 | NE | 0.676602939 | 1.213889325 |
| Cntn1 | 0.005875115 | 1.875544221 | NE | 0.68375077 | 1.135579703 |
| Letm2 | 0.001104306 | 2.371462071 | NE | 0.242181977 | 1.423588595 |
| Ptafr | 0.021173615 | 2.232120867 | NE | 0.540574153 | 1.317028776 |
| Me1 | 0.03823817 | 1.603254667 | NE | 0.863312513 | −1.062378672 |
| Smco1 | 0.026988488 | 2.508688181 | NE | 0.501298796 | 1.428939367 |
| Cyp2b10 | 0.009227326 | 2.023601722 | NE | 0.699603833 | 1.151733129 |
| Cyp2j13 | 0.001587354 | 3.68957984 | NE | 0.120415488 | 2.048773562 |
| Acot12 | 5.70E−05 | 2.402984772 | NE | 0.462442117 | 1.192539171 |
| Cyp2c29 | 6.17E−03 | 3.403244621 | NE | 0.593296835 | −1.391570036 |
| Akr1c19 | 0.08837154 | −1.323738676 | DOWN in Healthy | 0.000475667 | −2.037553198 |
| Gstm1 | 0.988990596 | −1.002868547 | DOWN in Healthy | 0.020964575 | −1.596954914 |
| Ces1f | 0.186446914 | −1.487066804 | DOWN in Healthy | 0.00373614 | −2.815884739 |
| Ces1g | 0.030963104 | −1.97871865 | DOWN in Healthy | 0.001377 | −3.774921051 |
| Tgfbr3 | 0.007704498 | −2.236046082 | NE | 0.553319278 | 1.228328585 |
| Acta1 | 0.006712918 | −2.803646543 | NE | 0.822471304 | −1.118236611 |
| Hist1h2bj | 0.000113721 | −3.822281003 | ND | 0.039087358 | −1.97509523 |
| Gp2 | 0.001158966 | −2.871474818 | NE | 0.208403405 | −1.534911637 |
| Ddit4 | 0.037955029 | −1.679764946 | NE | 0.861431628 | −1.065799056 |
| Hist1h2bn | 0.000151693 | −2.672909018 | ND | 0.037500512 | −1.707485507 |
| Ror2 | 7.86E−05 | −2.277636991 | NE | 0.05497608 | −1.473748863 |

NE: Not Evaluable; when DEG does not meet the filtering criteria in either comparison "CMA vs GF" or "Healthy vs GF", Change of Direction is not evaluable.
ND: Not Determined; when DEG meets the filtering criteria in both comparison "CMA vs GF" and "Healthy vs GF", the one with higher P value is reset to not determined to resolve conflicts.

Supplementary Table 5
108 OTUs differentially abundant between CMA and healthy mouse ileal samples.

| OTU | Change In Direction | DS-FDR Reject | DS-FDR Test Statistic | DS-FDR Raw Pvalues | Taxonomy |
|---|---|---|---|---|---|
| 349024 | UP in Healthy | TRUE | −0.22217917 | 0.000999001 | k__Bacteria; p__Firmicutes; c__Bacilli; o__Lactobacillales; f__Streptococcaceae; g__Streptococcus; s__ |
| 259772 | UP in Healthy | TRUE | 0.044282455 | 0.000999001 | k__Bacteria; p__Firmicutes; |

Supplementary Table 5
108 OTUs differentially abundant between CMA and healthy mouse ileal samples.

| OTU | Change In Direction | DS-FDR Reject | DS-FDR Test Statistic | DS-FDR Raw Pvalues | Taxonomy |
|---|---|---|---|---|---|
| | | | | | c__Clostridia; o__Clostridiales; f__Lachnospiraceae; g__Coprococcus; s__ |
| 828483 | UP in Healthy | TRUE | 0.017799339 | 0.021978022 | k__Bacteria; p__Firmicutes; c__Clostridia; o__Clostridiales; f__Clostridiaceae; g__Clostridium |
| 262095 | UP in Healthy | TRUE | 0.015344578 | 0.001998002 | k__Bacteria; p__Firmicutes; c__Erysipelotrichi; o__Erysipelotrichales; f__Erysipelotrichaceae; g__; s__ |
| 332718 | UP in Healthy | TRUE | 0.012123767 | 0.001998002 | k__Bacteria; p__Firmicutes; c__Bacilli; o__Lactobacillales; f__Streptococcaceae; g__Streptococcus; s__ |
| 360238 | UP in Healthy | TRUE | 0.007986609 | 0.011988012 | k__Bacteria; p__Firmicutes; c__Erysipelotrichi; o__Erysipelotrichales; __Erysipelotrichaceae; g__; s__ |
| 238205 | UP in Healthy | TRUE | 0.004499814 | 0.000999001 | k__Bacteria; p__Firmicutes; c__Clostridia; o__Clostridiales; f__Clostridiaceae; g__Clostridium; s__butyricum |
| 359750 | UP in Healthy | TRUE | 0.004188868 | 0.021978022 | k__Bacteria; p__Firmicutes; c__Clostridia; o__Clostridiales; f__Clostridiaceae; g__Clostridium; s__perfringens |
| New.ReferenceOTU16 | UP in Healthy | TRUE | 0.004114455 | 0.000999001 | k__Bacteria; p__Firmicutes; c__Bacilli; o__Lactobacillales; f__Streptococcaceae; g__Streptococcus; s__luteciae |
| 309696 | UP in Healthy | TRUE | 0.003306804 | 0.003996004 | k__Bacteria; p__Firmicutes; c__Bacilli; o__Lactobacillales; f__Streptococcaceae; g__Streptococcus; s__ |
| 345540 | UP in Healthy | TRUE | 0.003062398 | 0.000999001 | k__Bacteria; p__Proteobacteria; c__Gammaproteobacteria; o__Enterobacteriales; f__Enterobacteriaceae; g__; s__ |
| 586271 | UP in Healthy | TRUE | 0.002603169 | 0.01998002 | k__Bacteria; p__Firmicutes; c__Clostridia; o__Clostridiales; f__Lachnospiraceae; g__[Ruminococcus]; s__ |
| 356760 | UP in Healthy | TRUE | 0.002063474 | 0.000999001 | k__Bacteria; p__Firmicutes; c__Erysipelotrichi; o__Erysipelotrichales; |

-continued

| | Change In Direction | DS-FDR Reject | DS-FDR Test Statistic | DS-FDR Raw Pvalues | |
|---|---|---|---|---|---|
| OTU | | | | | Taxonomy |
| 303809 | UP in Healthy | TRUE | 0.001887759 | 0.000999001 | f__Erysipelotrichaceae; g__; s__ k__Bacteria; p__Firmicutes; c__Clostridia; o__Clostridiales; f__Clostridiaceae; g__Clostridium; s__butyricum |
| 327851 | UP in Healthy | TRUE | −0.00174762 | 0.001998002 | k__Bacteria; p__Firmicutes; c__Bacilli; o__Lactobacillales; f__Streptococcaceae; g__Streptococcus; s__ |
| New.Reference OTU18 | UP in Healthy | TRUE | 0.001578146 | 0.000999001 | k__Bacteria; p__Firmicutes; c__Clostridia; o__Clostridiales; f__Lachnospiraceae; g__Coprococcus; s__ |
| 291195 | UP in Healthy | TRUE | 0.001382348 | 0.000999001 | k__Bacteria; p__Firmicutes; c__Bacilli; o__Lactobacillales; f__Streptococcaceae; g__Streptococcus; s__ |
| 577710 | UP in Healthy | TRUE | 0.000950458 | 0.010989011 | k__Bacteria; p__Firmicutes; c__Clostridia; o__Clostridiales; f__Lachnospiraceae; g__Blautia; s__producta |
| 292820 | UP in Healthy | TRUE | 0.000949102 | 0.000999001 | k__Bacteria; p__Firmicutes; c__Bacilli; o__Lactobacillales; f__Streptococcaceae; g__Streptococcus; s__ |
| 573157 | UP in Healthy | TRUE | 0.000929379 | 0.011988012 | k__Bacteria; p__Firmicutes; c__Bacilli; o__Lactobacillales |
| 529116 | UP in Healthy | TRUE | 0.000921743 | 0.001998002 | k__Bacteria; p__Firmicutes; c__Clostridia; o__Clostridiales; f__Clostridiaceae; g__Clostridium |
| 579608 | UP in Healthy | TRUE | 0.000882353 | 0.001998002 | k__Bacteria; p__Firmicutes; c__Bacilli; o__Lactobacillales; f__Streptococcaceae; g__Streptococcus; s__ |
| 289925 | UP in Healthy | TRUE | 0.000678999 | 0.000999001 | k__Bacteria; p__Firmicutes; c__Bacilli; o__Lactobacillales; f__Streptococcaceae; g__Streptococcus; s__ |
| 177986 | UP in Healthy | TRUE | 0.000602909 | 0.028971029 | k__Bacteria; p__Firmicutes; c__Clostridia; o__Clostridiales; f__Lachnospiraceae; g__Coprococcus; s__ |
| New.CleanUp.Reference OTU64312 | UP in Healthy | TRUE | 0.000594549 | 0.003996004 | k__Bacteria; p__Firmicutes; c__Erysipelotrichi; o__Erysipelotrichales; |

Supplementary Table 5
108 OTUs differentially abundant between CMA and healthy mouse ileal samples.

-continued

Supplementary Table 5
108 OTUs differentially abundant between CMA and healthy mouse ileal samples.

| OTU | Change In Direction | DS-FDR Reject | DS-FDR Test Statistic | DS-FDR Raw Pvalues | Taxonomy |
|---|---|---|---|---|---|
| 967427 | UP in Healthy | TRUE | 0.000546212 | 0.001998002 | f__Erysipelotrichaceae; g__; s__ k__Bacteria; p__Firmicutes; c__Bacilli; o__Lactobacillales; f__Streptococcaceae; g__Streptococcus; s__ |
| 237444 | UP in Healthy | TRUE | 0.000487754 | 0.000999001 | k__Bacteria; p__Firmicutes; c__Bacilli; o__Lactobacillales; f__Streptococcaceae; g__Streptococcus; s__ |
| 328283 | UP in Healthy | TRUE | 0.000459212 | 0.003996004 | k__Bacteria; p__Firmicutes; c__Bacilli; o__Lactobacillales; f__Streptococcaceae; g__Streptococcus; s__ |
| 145801 | UP in Healthy | TRUE | −0.00045917 | 0.000999001 | k__Bacteria; p__Firmicutes; c__Erysipelotrichi; o__Erysipelotrichales; f__Erysipelotrichaceae; g__; s__ |
| New.ReferenceOTUI9 | UP in Healthy | TRUE | 0.000449108 | 0.026973027 | k__Bacteria; p__Firmicutes; c__Bacilli; o__Lactobacillales; f__Streptococcaceae; g__Streptococcus; s__ |
| 592866 | UP in Healthy | TRUE | 0.000408332 | 0.017982018 | k__Bacteria; p__Firmicutes; c__Clostridia; o__Clostridiales; f__Lachnospiraceae; g__[Ruminococcus]; s__ |
| 4313711 | UP in Healthy | TRUE | −0.00035444 | 0.000999001 | k__Bacteria; p__Firmicutes; c__Bacilli; o__Lactobacillales; f__Streptococcaceae; g__Streptococcus; s__ |
| New.ReferenceOTU26 | UP in Healthy | TRUE | 0.000337736 | 0.004995005 | k__Bacteria; p__Firmicutes; c__Clostridia; o__Clostridiales; f__Lachnospiraceae; g__Coprococcus; s__ |
| 351020 | UP in Healthy | TRUE | 0.000324044 | 0.014985015 | k__Bacteria; p__Firmicutes; c__Clostridia; o__Clostridiales; f__Clostridiaceae; g__Clostridium; s__neonatale |
| 833731 | UP in Healthy | TRUE | 0.000280741 | 0.000999001 | k__Bacteria; p__Proteobacteria; c__Gammaproteobacteria; o__Enterobacteriales; f__Enterobacteriaceae; g__; s__ |
| 392887 | UP in Healthy | TRUE | 0.000260077 | 0.025974026 | k__Bacteria; p__Firmicutes; c__Clostridia; o__Clostridiales; f__Lachnospiraceae; g__; s__ |
| 199301 | UP in Healthy | TRUE | 0.000256085 | 0.01998002 | k__Bacteria; p__Firmicutes; c__Clostridia; |

-continued

| | Supplementary Table 5 | | | | |
|---|---|---|---|---|---|
| | 108 OTUs differentially abundant between CMA and healthy mouse ileal samples. | | | | |
| OTU | Change In Direction | DS-FDR Reject | DS-FDR Test Statistic | DS-FDR Raw Pvalues | Taxonomy |
| New.CleanUp.ReferenceOTU98242 | UP in Healthy | TRUE | 0.000237095 | 0.002997003 | o__Clostridiales; f__Lachnospiraceae; g__; s__ k__Bacteria; p__Firmicutes; c__Clostridia; o__Clostridiales; f__Clostridiaceae; g__; s__ |
| 255359 | UP in Healthy | TRUE | −0.00020765 | 0.007992008 | k__Bacteria; p__Firmicutes; c__Bacilli; o__Lactobacillales; f__Streptococcaceae; g__Streptococcus; s__ |
| New.CleanUp.ReferenceOTU22852 | UP in Healthy | TRUE | 0.000197185 | 0.010989011 | k__Bacteria; p__Firmicutes; c__Clostridia; o__Clostridiales; f__Lachnospiraceae; g__Coprococcus; s__ |
| New.ReferenceOTU72 | UP in Healthy | TRUE | −0.00018357 | 0.021978022 | k__Bacteria; p__Firmicutes; c__Clostridia; o__Clostridiales; f__Lachnospiraceae; g__Coprococcus; s__ |
| 132041 | UP in Healthy | TRUE | 0.000168657 | 0.017982018 | k__Bacteria; p__Actinobactcria: c__Actinobactcria: o__Bifidobactcrialcs: f__Bifidobacteriaceae; g__Bifidobacterium; s__ |
| New.CleanUp.ReferenceOTUI02634 | UP in Healthy | TRUE | 0.000163884 | 0.022977023 | k__Bacteria; p__Firmicutes; c__Bacilli; o__Lactobacillales; f__Streptococcaceae; g__Streptococcus; s__ |
| New.CleanUp.ReferenceOTU48619 | UP in Healthy | TRUE | −7.42886E−05 | 0.014985015 | k__Bacteria; p__Firmicutes; c__Clostridia; o__Clostridiales; f__Lachnospiraceae; g__Coprococcus; s__ |
| New.CleanUp.ReferenceOTU92891 | UP in Healthy | TRUE | −7.35692E−05 | 0.022977023 | k__Bacteria; p__Firmicutes; c__Bacilli; o__Lactobacillales; f__Streptococcaceae; g__Streptococcus; s__ |
| 77514 | UP in CMA | TRUE | 0.000105274 | 0.028971029 | k__Bacteria; p__Firmicutes; c__Clostridia; o__Clostridiales; f__Lachnospiraceae; g__Blautia; s__ |
| 560336 | UP in CMA | TRUE | 0.000118911 | 0.028971029 | k__Bacteria; p__Bacteroidetes; c__Bacteroidia; o__Bacteroidales; f__Bacteroidaceae; g__Bacteroides; s__ |
| 566434 | UP in CMA | TRUE | 0.000132797 | 0.016983017 | k__Bacteria; p__Firmicutes; c__Clostridia; o__Clostridiales; f__;g__; s__ |
| 4352657 | UP in CMA | TRUE | 0.000145962 | 0.022977023 | k__Bacteria; p__Firmicutes; c__Clostridia; o__Clostridiales; |

-continued

Supplementary Table 5
108 OTUs differentially abundant between CMA and healthy mouse ileal samples.

| OTU | Change In Direction | DS-FDR Reject | DS-FDR Test Statistic | DS-FDR Raw Pvalues | Taxonomy |
|---|---|---|---|---|---|
| 367790 | UP in CMA | TRUE | 0.000158719 | 0.028971029 | f__Lachnospiraceae; g__Blautia; s__ k__Bacteria; p__Firmicutes; c__Clostridia; o__Clostridiales; f__Lachnospiraceae; g__Blautia; s__ |
| 3768338 | UP in CMA | TRUE | 0.000171334 | 0.028971029 | k__Bacteria; p__Firmicutes; c__Clostridia; o__Clostridiales; f__Lachnospiraceae; g__Blautia; s__ |
| 311587 | UP in CMA | TRUE | 0.000184786 | 0.007992008 | k__Bacteria; p__Firmicutes; c__Clostridia; o__Clostridiales; f__Lachnospiraceae; g__; s__ |
| 273232 | UP in CMA | TRUE | 0.000198366 | 0.022977023 | k__Bacteria; p__Verrucomicrobia: c__Verrucomicrobiae; o__Verrucomicrobiales; f__Verrucomicrobiaceae; g__Akkermansia; s__muciniphila |
| 804526 | UP in CMA | TRUE | 0.000198943 | 0.021978022 | k__Bacteria; p__Firmicutes; c__Clostridia; o__Clostridiales; f__Lachnospiraceae; g__Coprococcus; s__ |
| 331850 | UP in CMA | TRUE | 0.000211798 | 0.022977023 | k__Bacteria; p__Firmicutes; c__Clostridia; o__Clostridiales; f__Lachnospiraceae; g_Blautia; s__ |
| 4434334 | UP in CMA | TRUE | 0.000236036 | 0.003996004 | k__Bacteria; p__Firmicutes; c__Clostridia; o__Clostridiales; f__Clostridiaceae; g__; s__ |
| 4422039 | UP in CMA | TRUE | 0.000259764 | 0.002997003 | k__Bacteria; p__Firmicutes; c__Clostridia; o__Clostridiales; f__Lachnospiraceae |
| 343047 | UP in CMA | TRUE | 0.000280211 | 0.00999001 | k__Bacteria; p__Firmicutes; c__Clostridia; o__Clostridiales; f__Lachnospiraceae; g__Dorea; s__ |
| 295085 | UP in CMA | TRUE | 0.000318338 | 0.021978022 | k__Bacteria; p__Firmicutes; c__Clostridia; o__Clostridiales; f__Lachnospiraceae; g__Blautia; s__ |
| 195061 | UP in CMA | TRUE | 0.000318762 | 0.011988012 | k__Bacteria; p__Actinobacteria: c__Coriobacteriia; o__Coriobacteriales; f__Coriobacteriaceae; g__Adlercreutzia; s__ |
| 362539 | UP in CMA | TRUE | 0.000376855 | 0.015984016 | k__Bacteria; p__Firmicutes; c__Clostridia; o__Clostridiales; |

-continued

Supplementary Table 5
108 OTUs differentially abundant between CMA and healthy mouse ileal samples.

| OTU | Change In Direction | DS-FDR Reject | DS-FDR Test Statistic | DS-FDR Raw Pvalues | Taxonomy |
|---|---|---|---|---|---|
| New.CleanUp.ReferenceOTU35999 | UP in CMA | TRUE | 0.000385001 | 0.026973027 | f__Lachnospiraceae; g__; s__ k__Bacteria; p__Firmicutes; c__Erysipelotrichi; o__Erysipelotrichales; f__Erysipelotrichaceae; g__[Eubacterium]; s__dolichum |
| 587933 | UP in CMA | TRUE | 0.000403677 | 0.000999001 | k__Bacteria; p__Firmicutes; c__Erysipelotrichi; o__Erysipelotrichales; f__Erysipelotrichaceae; g__Coprobacillus; s__ |
| 3002161 | UP in CMA | TRUE | 0.000470934 | 0.01998002 | k__Bacteria; p__Firmicutes; c__Erysipelotrichi; o__Erysipelotrichales; f__Erysipelotrichaceae; g__[Eubacterium]; s__dolichum |
| 3715618 | UP in CMA | TRUE | 0.000529033 | 0.008991009 | k__Bacteria; p__Firmicutes; c__Clostridia; o__Clostridiales; f__Lachnospiraceae; g__[Ruminococcus]; s__gnavus |
| 591635 | UP in CMA | TRUE | 0.000561008 | 0.000999001 | k__Bacteria; p__Firmicutes; c__Clostridia; o__Clostridiales; f__Ruminococcaceae; g__Ruminococcus; s__ |
| 249142 | UP in CMA | TRUE | 0.000585252 | 0.027972028 | k__Bacteria; p__Firmicutes; c__Clostridia; o__Clostridiales; f__Lachnospiraceae; g__[Ruminococcusl; s__ |
| 634449 | UP in CMA | TRUE | 0.000585747 | 0.018981019 | k__Bacteria; p__Firmicutes; c__Clostridia; o__Clostridiales; f__Lachnospiraceae; g__; s__ |
| 318190 | UP in CMA | TRUE | 0.000620436 | 0.00999001 | k__Bacteria; p__Firmicutes; c__Clostridia; o__Clostridiales; f__Ruminococcaceae; g__; s__ |
| 548587 | UP in CMA | TRUE | 0.000660208 | 0.014985015 | k__Bacteria; p__Firmicutes; c__Erysipelotrichi; o__Erysipelotrichales; f__Erysipelotrichaceae; g__[Eubacterium]; s__dolichum |
| New.ReferenceOTU4 | UP in CMA | TRUE | 0.000693503 | 0.013986014 | k__Bacteria; p__Firmicutes; c__Clostridia; o__Clostridiales; f__Lachnospiraceae; g__[Ruminococcus]; s__gnavus |
| New.CleanUp.ReferenceOTUI1241 | UP in CMA | TRUE | 0.000784602 | 0.002997003 | k__Bacteria; p__Firmicutes; c__Erysipelotrichi; o__Erysipelotrichales; f__Erysipelotrichaceae; |

-continued

Supplementary Table 5
108 OTUs differentially abundant between CMA and healthy mouse ileal samples.

| OTU | Change In Direction | DS-FDR Reject | DS-FDR Test Statistic | DS-FDR Raw Pvalues | Taxonomy |
|---|---|---|---|---|---|
| 535955 | UP in CMA | TRUE | 0.000789934 | 0.002997003 | g__[Eubacterium]; s__dolichum k__Bacteria; p__Firmicutes; c__Clostridia; o__Clostridiales; f__Peptostreptococcaceae; g__; s__ |
| 551902 | UP in CMA | TRUE | 0.000807109 | 0.002997003 | k__Bacteria; p__Firmicutes; c__Clostridia; o__Clostridiales; f__Ruminococcaceae; g__; s__ |
| 535601 | UP in CMA | TRUE | 0.000857422 | 0.002997003 | k__Bacteria; p__Firmicutes; c__Clostridia; o__Clostridiales; f__Lachnospiraceae; g__; s__ |
| 269611 | UP in CMA | TRUE | 0.000862436 | 0.016983017 | k__Bacteria; p__Firmicutes; c__Clostridia; o__Clostridiales; f__Ruminococcaceae; g__; s__ |
| 175508 | UP in CMA | TRUE | 0.000942059 | 0.005994006 | k__Bacteria; p__Actinobacteria; c__Coriobacteriia; o__Coriobacteriales; f__Coriobacteriaceae; g__; s__ |
| 585914 | UP in CMA | TRUE | 0.001135819 | 0.014985015 | k__Bacteria; p__Bacteroidetes; c__Bacteroidia; o__Bacteroidales; f__Porphyromonadaceae; g__Parabacteroides; s__distasonis |
| 587530 | UP in CMA | TRUE | 0.001147768 | 0.004995005 | k__Bacteria; p__Firmicutes; c__Erysipelotrichi; o__Erysipelotrichales; f__Erysipelotrichaceae; g__[Eubacterium]; s__dolichum |
| 659361 | UP in CMA | TRUE | 0.001476101 | 0.002997003 | k__Bacteria; p__Firmicutes; c__Clostridia; o__Clostridiales; f__Lachnospiraceae; g__Dorea; s__ |
| New.ReferenceOTU85 | UP in CMA | TRUE | 0.001499115 | 0.010989011 | k__Bacteria; p__Firmicutes; c__Clostridia; o__Clostridiales; f__Lachnospiraceae; g__Dorea; s__ |
| 193744 | UP in CMA | TRUE | 0.001689778 | 0.017982018 | k__Bacteria; p__Firmicutes; c__Clostridia; o__Clostridiales; f__Lachnospiraceae; g__Blautia; s__ |
| 583656 | UP in CMA | TRUE | 0.001702377 | 0.014985015 | k__Bacteria; p__Bacteroidetes; c__Bacteroidia; o__Bacteroidales; f__Bacteroidaceae; g__Bacteroides; s |
| 631764 | UP in CMA | TRUE | 0.001846097 | 0.002997003 | k__Bacteria; p__Actinobacteria; |

-continued

Supplementary Table 5
108 OTUs differentially abundant between CMA and healthy mouse ileal samples.

| OTU | Change In Direction | DS-FDR Reject | DS-FDR Test Statistic | DS-FDR Raw Pvalues | Taxonomy |
|---|---|---|---|---|---|
| 564188 | UP in CMA | TRUE | 0.001945213 | 0.001998002 | c_Coriobacteriia; o_Coriobacteriales; f_Coriobacteriaceae; g_Adlercreutzia; s_ k_Bacteria; p_Firmicutes; c_Clostridia; o_Clostridiales; f_Lachnospiraceae; g_Dorea; s_ |
| 531675 | UP in CMA | TRUE | 0.001946525 | 0.022977023 | k_Bacteria; p_Firmicutes; c_Clostridia; o_Clostridiales; f_Lachnospiraceae; g_Blautia; s_ |
| New.ReferenceOTU35 | UP in CMA | TRUE | 0.002345204 | 0.024975025 | k_Bacteria; p_Firmicutes; c_Clostridia; o_Clostridiales; f_Lachnospiraceae; g_; s_ |
| 572860 | UP in CMA | TRUE | 0.002838657 | 0.001998002 | k_Bacteria; p_Firmicutes; c_Clostridia; o_Clostridiales; f_Lachnospiraceae; g_[Ruminococcus]; s_gnavus |
| 362342 | UP in CMA | TRUE | 0.00291165 | 0.02997003 | k_Bacteria; p_Firmicutes; c_Clostridia; o_Clostridiales; f_Ruminococcaceae; g_Ruminococcus; s_ |
| 929836 | UP in CMA | TRUE | 0.003147941 | 0.000999001 | k_Bacteria; p_Firmicutes; c_Erysipelotrichi; o_Erysipelotrichales; f_Erysipelotrichaceae; g_Coprobacillus; s_ |
| 1111191 | UP in CMA | TRUE | 0.003451219 | 0.000999001 | k_Bacteria; p_Firmicutes; c_Clostridia; o_Clostridiales; f_Lachnospiraceae; g_[Ruminococcus]; s_gnavus |
| 535375 | UP in CMA | TRUE | 0.003453613 | 0.008991009 | k_Bacteria; p_Bacteroidetes; c_Bacteroidia; o_Bacteroidales; f_Bacteroidaceae; g_Bacteroides; s_ |
| 551822 | UP in CMA | TRUE | 0.004090919 | 0.005994006 | k_Bacteria; p_Firmicutes; c_Clostridia; o_Clostridiales; f_Clostridiaceae |
| 368486 | UP in CMA | TRUE | 0.004218387 | 0.003996004 | k_Bacteria; p_Firmicutes; c_Erysipelotrichi; o_Erysipelotrichales; f_Erysipelotrichaceae; g_[Eubacterium]; s_dolichum |
| 583398 | UP in CMA | TRUE | 0.00561987 | 0.000999001 | k_Bacteria; p_Firmicutes; c_Clostridia; o_Clostridiales; f_Lachnospiraceae; g_[Ruminococcus]; s_ |

-continued

Supplementary Table 5
108 OTUs differentially abundant between CMA and healthy mouse ileal samples.

| OTU | Change In Direction | DS-FDR Reject | DS-FDR Test Statistic | DS-FDR Raw Pvalues | Taxonomy |
|---|---|---|---|---|---|
| New.ReferenceOTUI66 | UP in CMA | TRUE | 0.006055017 | 0.024975025 | k__Bacteria; p__Firmicutes; c__Clostridia; o__Clostridiales; f__Lachnospiraceae |
| 367213 | UP in CMA | TRUE | 0.006097534 | 0.022977023 | k__Bacteria; p__Firmicutes; c__Clostridia; o__Clostridiales; f__Ruminococcaceae; g__; s__ |
| 546876 | UP in CMA | TRUE | 0.009753471 | 0.022977023 | k__Bacteria; p__Firmicutes; c__Clostridia; o__Clostridiales; f__Lachnospiraceae; g__Blautia; s__ |
| 369763 | UP in CMA | TRUE | 0.010722879 | 0.00999001 | k__Bacteria; p__Firmicutes; c__Erysipelotrichi; o__Erysipelotrichales; f__Erysipelotrichaceae; g__Coprobacillus; s__ |
| 829337 | UP in CMA | TRUE | 0.011237604 | 0.011988012 | k__Bacteria; p__Firmicutes; c__Erysipelotrichi; o__Erysipelotrichales; f__Erysipelotrichaceae; g__Coprobacillus; s__ |
| 592616 | UP in CMA | TRUE | 0.013715698 | 0.000999001 | k__Bacteria; p__Firmicutes; c__Erysipelotrichi; o__Erysipelotrichales; f__Erysipelotrichaceae; g__; s__ |
| 582691 | UP in CMA | TRUE | 0.01557264 | 0.002997003 | k__Bacteria; p__Firmicutes; c__Clostridia; o__Clostridiales; f__Clostridiaceae; g__; s__ |
| 628226 | UP in CMA | TRUE | 0.024223372 | 0.004995005 | k__Bacteria; p__Firmicutes; c__Clostridia; o__Clostridiales; f__Clostridiaceae; g__; s__ |
| 1078587 | UP in CMA | TRUE | 0.032792882 | 0.015984016 | k__Bacteria; p__Firmicutes; c__Clostridia; o__Clostridiales; f__Lachnospiraceae; g__Blautia; s__ |
| 370183 | UP in CMA | TRUE | 0.044102787 | 0.01998002 | k__Bacteria; p__Firmicutes; c__Clostridia; o__Clostridiales; f__Lachnospiraceae; g__Blautia; s__ |
| 363731 | UP in CMA | TRUE | 0.055865924 | 0.025974026 | k__Bacteria; p__Verrucomicrobia; c__Verrucomicrobiae; o__Verrucomicrobiales; f__Verrucomicrobiaceae; g__Akkermansia; s__muciniphila |
| 360015 | UP in CMA | TRUE | 0.07274586 | 0.022977023 | k__Bacteria; p__Firmicutes; c__Clostridia; o__Clostridiales; f__Lachnospiraceae; |

-continued

Supplementary Table 5
108 OTUs differentially abundant between CMA and healthy mouse ileal samples.

| OTU | Change In Direction | DS-FDR Reject | DS-FDR Test Statistic | DS-FDR Raw Pvalues | Taxonomy |
|---|---|---|---|---|---|
| 579851 | UP in CMA | TRUE | 0.082564668 | 0.000999001 | g_[Ruminococcus]; s_gnavus k_Bacteria; p_Firmicutes; c_Erysipelotrichi; o_Erysipelotrichales; f_Erysipelotrichaceae; g_[Eubacterium]; s_dolichum |

Supplementary TABLE 6

Primer sequence used for qPCR analysis
of *Anaerostipes caccae*

| | | | |
|---|---|---|---|
| *Anaerostipes caccae* | F | GTTTTCGGATGG ATTTCCTATAT (SEQ ID NO: 1) | Ref 24. |
| | R | CTTTTCACACTGA ATCATGCGATT (SEQ ID NO: 2) | |

SUPPLEMENTARY TABLE 7

Primer sequences used for
qPCR analysis in FIG. 4f

| | | | |
|---|---|---|---|
| Hprt | F | TGAAGAGCTACT GTAATGATCAGT CAAC (SEQ ID NO: 3) | Ref. 50. |
| | R | AGCAAGCTTGCA ACCTTAACCA (SEQ ID NO: 4) | |
| Fbp1 | F | CCATCATAATCG AACCTGAG (SEQ ID NO: 5) | Ref. 51. |
| | R | CTTCTCAGAAGG CTCATCAG (SEQ ID NO: 6) | |
| Tgfbr3 | F | CCGGTGTGAACT GTCACCGATC (SEQ ID NO: 7) | Modified from Ref. 52 |
| | R | CCTGATGAAAAC TGGACCACAG (SEQ ID NO: 8) | |
| Ror2 | F | ATCGACACCTTG GGACAACC (SEQ ID NO: 9) | Ref. 20. |
| | R | AGTGCAGGATTG CCGTCTG (SEQ ID NO: 10) | |
| Acot12 | F | CCGTGGCACTAA GGTCAGTT (SEQ ID | Ref. 53. |

SUPPLEMENTARY TABLE 7-continued

Primer sequences used for
qPCR analysis in FIG. 4f

| | | | |
|---|---|---|---|
| | | NO: 11) | |
| | R | ACGTTACGGTGC ACGAATTG (SEQ ID NO: 12) | |
| Mel | F | AGTATCCATGAAC AAAGGGCAC (SEQ ID NO: 13) | Ref. 54. |
| | R | ATCCCATTACAGC CAAGGTC (SEQ ID NO: 14) | |

Example 2: Isolation and Characterization, In Vitro Fermentation, Initial In Vivo Experimental Design A. *A. Caccae* Isolation and Characterization

*A. caccae* is isolated from healthy infant feces frozen in 30% glycerol stock. First, undiluted fecal glycerol stock from healthy donor #2 is plated on brain heart infusion (BHI) agar supplemented with Vitamin K, hemin, and antibiotics. The antibiotics used are 16 μg/ml ciprofloxacin or a mixture of 16 μg/ml ciprofloxacin, 6 μg/ml gentamicin, 5 μg/ml aztreonam, and 10 μg/ml colistin (58, 60). This donor was chosen because he had the highest relative abundance of *A. caccae* of the four healthy donors from previous sequencing data. Plates are incubated in anaerobic chambers at 37° C. for six days. The plates are then scraped and suspended in 50% glycerol solution. This suspension is then aliquoted and one aliquot is used for qPCR and the other is frozen at −80° C. to be used for future cultures. *A. caccae* abundance is quantified using qPCR with species-specific primers against the 16S rRNA gene (24). The frozen aliquot of the suspension from the plate(s) shown to have the highest abundance of *A. caccae* are diluted and plated on BHI agar and incubated in anaerobic chambers at 37° C. for six days. Single colonies are then selected from the $10^{-5}$ dilution and inoculated into pre-reduced chopped meat and glucose broth (CMG) and incubated in an anaerobic chamber overnight. An aliquot of this broth culture is then then taken for *A. caccae* specific PCR and universal PCR 16S rRNA amplification for Sanger sequencing. Another aliquot is taken and diluted 1:1 with 50% glycerol solution and frozen at −80° C. in cryovials. Colonies that are positive for *A. caccae* by both PCR and Sanger sequencing are then streaked onto BHI agar from the frozen cryovial to increase purity. A single colony from this plate is then inoculated into chopped meat+glucose broth and grown overnight at 37° C. in the anaerobic chamber. Aliquots of this stock culture are diluted 1:1 in 50% glycerol and stored in cryovials at −80° C. for future studies. This isolation is shown in FIG. 15.

Further confirmation of *A. caccae* isolation is analyzed by CosmosID® whole genome analysis. The method described in FIG. 15 produced 7 *A. caccae* isolates, all derived from healthy donor #2. The three colonies that seemed the most different from each other by Sanger sequencing (denoted 66a_Rep_1_1_IonXpress_011_trimmed, D24_colony_4_2_IonXpress_015, D24_colony_5_IonXpress_016) were whole genome sequenced. All three colonies analyzed are highly similar to *A. caccae* 3_2_56FAA and *A. caccae* DSM 14662 but a unique strain from these known references. They are within the cutoff homology to be classified as *A. caccae* (>98.5%) homology, but the SNP distance (>100 SNPs) identifies our isolates as a unique strain from the reference strains 3_2_56FAA and DSM 14662. However, all of our isolates are identical to each other (0 SNPs), so this strain is herein referred to as *A. caccae*_lah. The whole genome analysis by CosmosID® also confirmed the absence of any virulence genes in the isolates and the only antibiotic resistance gene recorded was for the tetracycline class. This is further depicted in the following table, Supplementary Table 8.

SUPPLEMENTARY TABLE 8

Genome analysis

| | Anaerostipes_caccae_DSM_14662_DSM_14662 | Anaerostipes_caccae_3_2_56FAA | D24_colony_4_2_IonXpress_015 | D24_colony_5_IonXpress_016 | 66a_Rep_1_IonXpress_011_trimmed | Anaerostipes_hadrus_27895TDY56088686 | Anaerostipes_hadrus_DSM_3319_DSM_3319 | Anaerostipes_hadrus_PEL_85 | Anaerostipes_hadrus_BPB5 |
|---|---|---|---|---|---|---|---|---|---|
| Anaerostipes_caccae_DSM_14662_DSM_14662 | 0 | 149 | 124 | 124 | 124 | 31351 | 31326 | 31378 | 31363 |
| Anaerostipes_caccae_3_2_56FAA | 149 | 0 | 101 | 101 | 101 | 31365 | 31340 | 31392 | 31377 |
| D24_colony_4_2_IonXpress_015 | 124 | 101 | 0 | 0 | 0 | 31340 | 31315 | 31367 | 31352 |
| D24_colony_5_IonXpress_016 | 124 | 101 | 0 | 0 | 0 | 31340 | 31315 | 31367 | 31352 |
| 66a_Rep_1_IonXpress_011_trimmed | 124 | 101 | 0 | 0 | 0 | 31340 | 31335 | 31367 | 31352 |
| Anaerostipes_hadrus_27895TDY56088686 | 31351 | 31365 | 31340 | 31340 | 31340 | 0 | 140 | 192 | 177 |
| Anaerostipes_hadrus_DSM_3319_DSM_3319 | 31326 | 31340 | 31315 | 31315 | 33315 | 140 | 0 | 124 | 109 |
| Anaerostipes_hadrus_PEL_85 | 31378 | 31392 | 31367 | 31367 | 31367 | 192 | 124 | 0 | 126 |
| Anaerostipes_hadrus_BPB5 | 31363 | 31377 | 31352 | 31352 | 31352 | 177 | 109 | 126 | 0 |

Our isolates:
D24_colony_42;
D24_colony_5; 66a

Antibiotic susceptibility of *A. caccae*_lah was characterized by growth inhibition around antibiotic discs. An ice-chip of the frozen *A. caccae*_lah stock is grown in CMG broth overnight and 100 µl of broth is spread on BHI agar. Antibiotic discs (10 µg streptomycin, 30 µg kanamycin, 30 µg tetracycline and 10 µg ampicillin) are then placed on top of the agar to measure zone of clearance which demonstrates antibiotic susceptibility. Plates are incubated at 37° C. in anaerobic conditions for six days. *A. caccae*_lah is highly susceptible to ampicillin as shown by the large radius of clearance (FIG. 16). It is also somewhat susceptible to tetracycline even though it possesses a tetracycline-resistance gene (FIG. 16).

B. In Vitro Fermentation

*A. caccae*_lah is not able to ferment complex carbohydrates in monoculture but can ferment simple sugars like those in infant formula, including lactose. An ice-chip of the *A. caccae*_lah stock was grown for 24 h in CMG broth at 37° C. in anaerobic conditions. This method of preculture is used for all future in vitro fermentation experiments. Then 10 µl of preculture was transferred into 7 mL minimal peptone yeast (PY) broth alone or supplemented with 10 mg/ml of glucose, sucrose, lactose, cellobiose, or potato starch. All of these variations of PY were pre-reduced anaerobically prepared by Anaerobe Systems. Growth and butyrate production were measured after 48 h. *A. caccae*_lah grew abundantly when PY broth was supplemented with sucrose, glucose, and lactose compared to cellobiose or potato starch as measured by OD600. Butyrate in solution is quantified by HPLC-UV-Vis as described in reference 61 and 62. Similarly to growth, *A. caccae*_lah produced the most butyrate when grown in sucrose, glucose, or lactose. These simple sugars are similar to those found in infant formula. To test the abundance of *A. caccae*_lah and its butyrate production in infant formula, *A. caccae*_lah was grown in PY broth supplemented with Nutramigen® (10 mg/ml carbohydrates), an iron-fortified, hypoallergenic infant formula designed for infants with CMA, or Enfamil® (10 mg/ml carbohydrates), standard infant formula containing cow's milk. These are the same formulas consumed by the healthy (Enfamil®) and CMA (Nutramigen®) infant donors and are also consumed by all mice colonized with these respective microbiomes. *A. caccae*_lah abundance was similar when grown with Enfamil® or Nutramigen® as PY broth, proving that *A. caccae*_lah does not depend on consuming cow's milk for growth. However, butyrate production was highest in Nutramigen® compared to PY broth alone. The majority sugar in Nutramigen® is corn syrup which contains fructose and sucrose, which mirrors the high butyrate production by *A. caccae*_lah when supplemented with sucrose alone. All groups were analyzed by one way ANOVA. *$P<0.05$, $P<0.01$, *$P<0.001$, **$P<0.0001$ versus PY. These results are shown in FIG. 17**.

*A. caccae*_lah is able to use lactate and acetate together to produce butyrate. *A. caccae* and other Clostridia are generally considered as fiber fermenting species, however as seen in previous data *A. caccae*_lah alone is not able to consume complex fibers for growth or butyrate production. Other groups have shown that primary degraders, namely *Bacteroides* species, break down complex fibers and produce metabolites lactate and acetate which Clostridia species can then consume to produce butyrate (59). To examine whether this complex cross-feeding could be mimicked in vitro, PY broth is supplemented with only these metabolites to stimulate butyrate production by *A. caccae*_lah. *A. caccae*_lah preculture was grown from frozen glycerol stock as described above, then 101 was transferred into minimal PY broth supplemented with 33 mM acetate and/or 40 mM lactate (57). Growth and butyrate production were measured after 48 h. As shown in FIG. 18, *A. caccae*_lah had significant growth when supplemented with either or both of the metabolites. Interestingly, the strain only produced significantly high levels of butyrate when supplemented with both lactate and acetate compared to single supplementation. This data supports cross-feeding mechanisms and metabolic cycles described by other publications for bacteria in this family. All groups were analyzed by one way ANOVA. *$P<0.05$, $P<0.01$, *$P<0.001$, ****$P<0.0001$ versus PY alone.

As shown in FIG. 19, *A. caccae*_lah produces substantially greater butyrate from complex carbohydrates in co-culture with a complex bacterial mix from an allergic (CMA) infant donor. *A. caccae*_lah or human CMA fecal sample (frozen glycerol stock from human donor 6) precultures were grown as described above. Then 10 µl total (10 µl *A. caccae*_lah, 10 µl CMA, or 5 µl *A. caccae*_lah+5 µl CMA) was transferred into minimal PY broth alone or supplemented with 10 mg/ml potato starch or cellobiose (Anaerobe Systems). Growth and butyrate production were measured after 48 h. *A. caccae*_lah in monoculture grew similarly across all three media and was below the detection limit in the CMA culture. When *A. caccae*_lah is co-cultured with the CMA bacterial mix, its abundance was similar or slightly higher than that in single culture growth as measured by qPCR. This demonstrates that *A. caccae*_lah is able to compete for substrate and establish a niche in complex co-culture. As shown previously, *A. caccae*_lah in monoculture was not able to produce significant butyrate when grown in either carbohydrate-supplemented media. Butyrate production was also minimal by the CMA culture alone in PY and PY+Starch. However, the co-culture produced significantly higher levels of butyrate compared to *A. caccae*_lah alone or CMA alone when supplemented with either carbohydrate, particularly starch. There is some evidence that potato starch may be a good prebiotic supplement to support growth and butyrate production of *A. caccae*_lah in vivo. When supplemented with cellobiose, CMA and co-culture produced more butyrate than *A. caccae*_lah alone suggesting that the CMA bacterial mix contains some species capable of producing butyrate from the breakdown of fiber, and that the addition of *A. caccae*_lah doesn't contribute any additional butyrate to the system. Thus cellobiose would not be a suitable prebiotic supplement.

The inventors determined if the bacterial mix from the feces of CMA-colonized repository mice would behave similarly to the human CMA mix, because the feces of these repository mice will be used to colonize all future CMA mice. Fecal pellets from repository mice previously colonized from CMA donor 6 were collected, homogenized in sterile PBS, then diluted 1:1 in 50% glycerol solution and frozen at −80° C. in cryovials. Precultures of *A. caccae*_lah, human CMA microbiota (hCMA) and mouse CMA microbiota (msCMA) were prepared as described above. Precultures were then inoculated into PY broth with or without supplements alone (10 ul), together (5 ul *A. caccae*+5 ul CMA), or *A. caccae*_lah and supplements were added 24 h later. The supplements (Nutramigen®, lactate/acetate) were added in the same concentration as previously described, and approximately 10 mg/ml wheat bran was used. Growth and butyrate production were measured at t=48 h or 72 h, to allow full 48 h growth of *A. caccae* in the group in which it was added at the later time point. Neither CMA mix had measurable *A. caccae*, as expected. The bacterial mix from the CMA repository mouse feces produces more butyrate at baseline than freshly thawed human CMA feces, but addition of *A. caccae*_lah with lactate and acetate still results in a notable increase in butyrate concentration (FIG. 20). There are many factors that may contribute to the difference between the two CMA sources including loss of species during transfer into the mouse, an increase in the abundance of butyrate producers in the repository mouse over time, or the difference in the time spent in frozen culture.

*A. caccae*_lah is able to grow when inoculated in lower abundance in vitro. In this series of experiments, the inventors determined if *A. caccae*_lah would still be able to grow in co-culture when inoculated with lower abundance than the CMA mix, as *A. caccae* will be in much lower relative abundance when introduced into a CMA-colonized mouse. This experiment was performed to reflect the reality of introducing *A. caccae*_lah into a CMA-colonized mouse more accurately than a simultaneous, 1:1 inoculation. *A. caccae*_lah or the CMA pre-cultures were performed as described herein, then 10 μl was transferred into minimal PY broth supplemented with 10 mg/ml carbohydrates (10 mg/ml carbohydrates Nutramigen®, Nutramigen® plus 10 mg/ml scFOS (short chain fructo-oligosaccharide, a clinical prebiotic), or Nutramigen® plus LA (40 mM lactate+33 mM acetate)). *A. caccae*_lah and CMA precultures were transferred in to supplemented PY broth or CMG broth in various ratios: 10 ul *A. caccae*_lah:0 ul CMA; 5 ul *A. caccae*_lah: 5 ul CMA; 3 ul *A. caccae*_lah:7 ul CMA; 1 ul *A. caccae*_lah:9 ul CMA. As shown by species-specific qPCR, the volume of *A. caccae*_lah didn't notably affect its expansion or butyrate production. Addition of the scFOS decreased total butyrate concentration compared to media with Nutramigen® alone. The addition of lactate and acetate results in the greatest butyrate concentration. The amount of butyrate in this media is greater in co-culture than in *A. caccae*_lah alone, and in the *A. caccae*_lah monoculture there is no detectable lactate or acetate in the media at 48 h. This suggests that the CMA species in culture are contributing additional lactate and acetate to the system, which may allow continued butyrate production by *A. caccae*_lah after the supplemented metabolites are depleted.

Before beginning in vivo colonization experiments, the presence of *A. caccae* in the healthy repository mice and absence in CMA repository mice was confirmed and measured by qPCR. Repository mice colonized with feces from healthy infant donor 2 show measurable *A. caccae* abundance by qPCR, while repository mice colonized with feces from CMA donor 6 do not. The inventors predict that providing *A. caccae*_lah to CMA colonized mice with the prebiotic supplements will allow the species to grow and establish a niche in the host. Ideally, the inventors would be able to administer *A. caccae*_lah such that the abundance of *A. caccae*_lah in CMA colonized mice reaches a level similar to that detected in healthy colonized mice.

C. Experimental Plan for Initial In Vivo Studies (FIG. 21)

In this experiment, the inventors aim to validate colonization of *A. caccae*_lah into CMA-colonized mice and its dependence on prebiotic supplements. Germ free (GF) C3H/HeN germ free mice are weaned and fed with Nutramigen®. At the same time, mice are given a fecal slurry from CMA repository mouse (human donor 6) by intragastric gavage (I.G.) to establish the CMA-microenvironment in the mouse model. The CMA microbes are given 7 days to colonize. The mice receive a continuous supply of Nutramigen® throughout the experiment. The ad libitum feeding of the mice with Nutramigen®, along with additional lactate/acetate or carbohydrate supplements may provide enough continuous substrate to help *A. caccae* colonize. Beginning on day 7 after weaning, mice receive I.G. gavage of both *A. caccae*_lah and prebiotic or control. Cohorts of mice receive 100 ul of PBS (control) or one prebiotic supplement (10 mg/ml lactate plus 10 mg/ml acetate or 10 mg/ml potato starch) just after fecal collection. Thirty minutes later, mice receive 250 ul of live biotherapeutic product (LBP, i.e. approximately $1 \times 10^6$ CFU *A. caccae*_lah), or the same volume of sterile CMG broth in glycerol as the negative control. After the first week, gavage of the LBP is stopped, but the prebiotic (or control) continues to be administered for another week. This is to determine whether administration of the prebiotic is sufficient to maintain the LBP (*A. caccae*_lah) population in the mouse without introducing more bacteria. Fecals are collected daily during this two week period to analyze abundance of *A. caccae*_lah by qPCR and fecal butyrate concentration by HPLC UV-Vis. Mice are sacrificed at day 42 or at the first timepoint that *A. caccae* abundance is not detected in the feces. After sacrifice, cecal butyrate is measured and expression of the genes Ror2, Fbp1, Tgfbr3, Acot1, and Me1 are analyzed in ileal intestinal epithelial cells (iIECs) by qPCR. Cecal butyrate is normally a more sensitive measure than fecal butyrate, and may be a better measure of butyrate production by *A. caccae*_lah in vivo because most butyrate produced in the colon is immediately consumed by colonocytes. These specific genes are chosen for analysis in iIECs because they are immunologically relevant and were shown to be differentially expressed between healthy-, CMA-, and *A. caccae*-colonized mice (See FIG. 4*f*).

As an additional experiment, the inventors may aim to enhance the colonization by *A. caccae*_lah by additionally delivering a butyrate carrying compound to the mice by I.G. gavage. Examples of butyrate carrying compounds are described in published PCT application WO 2018/195067 A1, Hubbell et al. A solution of 80 mg/mL of the butyrate delivering polymer pHPMA-b-pBMA is prepared and diluted to 53.3 mg/mL as described in Hubbell et al. In the experiment described directly above [paragraph 129], the cohorts of mice receiving the prebiotic supplement also receive 125 μL of this diluted butyrate delivering polymer solution by I.G. gavage immediately after receiving the prebiotic supplement. The remainder of the experiment is carried out as described above.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Sicherer, S. H., et al. Critical Issues in Food Allergy: A National Academies Consensus Report. *Pediatrics* (2017).
2. Iweala, O. I. & Burks, A. W. Food Allergy: Our Evolving Understanding of Its Pathogenesis, Prevention, and Treatment. *Curr Allergy Asthma Rep* 16, 37 (2016).
3. Wesemann, D. R. & Nagler, C. R. The Microbiome, Timing, and Barrier Function in the Context of Allergic Disease. *Immunity* 44, 728-738 (2016).
4. Plunkett, C. H. & Nagler, C. R. The Influence of the Microbiome on Allergic Sensitization to Food. *J Immunol* 198, 581-589 (2017).
5. Berni Canani, R., et al. *Lactobacillus rhamnosus* GG-supplemented formula expands butyrate-producing bacterial strains in food allergic infants. *Isme j* 10, 742-750 (2016).
6. Bunyavanich, S., et al. Early-life gut microbiome composition and milk allergy resolution. *J Allergy Clin Immunol* 138, 1122-1130 (2016).
7. Stefka, A. T., et al. Commensal bacteria protect against food allergen sensitization. *Proc Natl Acad Sci USA* 111, 13145-13150 (2014).
8. Dominguez-Bello, M. G., et al. Delivery mode shapes the acquisition and structure of the initial microbiota across multiple body habitats in newborns. *Proc Natl Acad Sci USA* 107, 11971-11975 (2010).
9. Mueller, N. T., Bakacs, E., Combellick, J., Grigoryan, Z. & Dominguez-Bello, M. G. The infant microbiome development: mom matters. *Trends Mol Med* 21, 109-117 (2015).
10. Blanton, L. V., et al. Gut bacteria that prevent growth impairments transmitted by microbiota from malnourished children. *Science* 351(2016).
11. Cahenzli, J., Koller, Y., Wyss, M., Geuking, M. B. & McCoy, K. D. Intestinal microbial diversity during early-life colonization shapes long-term IgE levels. *Cell Host Microbe* 14, 559-570 (2013).
12. Pabst, O. & Mowat, A. M. Oral tolerance to food protein. *Mucosal Immunol* 5, 232-239 (2012).
13. Honda, K. & Littman, D. R. The microbiota in adaptive immune homeostasis and disease. *Nature* 535, 75-84 (2016).
14. Thaiss, C. A., Zmora, N., Levy, M. & Elinav, E. The microbiome and innate immunity. *Nature* 535, 65-74 (2016).
15. Yanez, A. J., et al. Broad expression of fructose-1,6-bisphosphatase and phosphoenolpyruvate carboxykinase provide evidence for gluconeogenesis in human tissues other than liver and kidney. *J Cell Physiol* 197, 189-197 (2003).
16. Ostroukhova, M., et al. The role of low-level lactate production in airway inflammation in asthma. *Am J Physiol Lung Cell Mol Physiol* 302, L300-307 (2012).
17. Zhu, Y., et al. NPM1 activates metabolic changes by inhibiting FBP1 while promoting the tumorigenicity of pancreatic cancer cells. *Oncotarget* 6, 21443-21451 (2015).
18. Berger, C. N., et al. *Citrobacter rodentium* Subverts ATP Flux and Cholesterol Homeostasis in Intestinal Epithelial Cells In Vivo. *Cell Metab* (2017).
19. Zhang, M., Zola, H., Read, L. & Penttila, I. Identification of soluble transforming growth factor-beta receptor III (sTbetaIII) in rat milk. *Immunol Cell Biol* 79, 291-297 (2001).
20. Miyoshi, H., Ajima, R., Luo, C. T., Yamaguchi, T. P. & Stappenbeck, T. S. Wnt5a potentiates TGF-beta signaling to promote colonic crypt regeneration after tissue injury. *Science* 338, 108-113 (2012).
21. Planer, J. D., et al. Development of the gut microbiota and mucosal IgA responses in twins and gnotobiotic mice. *Nature* 534, 263-266 (2016).
22. Schwiertz, A., et al. *Anaerostipes caccae* gen. nov., sp. nov., a new saccharolytic, acetate-utilising, butyrate-producing bacterium from human faeces. *Systematic and applied microbiology* 25, 46-51 (2002).
23. Duncan, S. H., Louis, P. & Flint, H. J. Lactate-utilizing bacteria, isolated from human feces, that produce butyrate as a major fermentation product. *ApplEnviron Microbiol* 70, 5810-5817 (2004).
24. Kurakawa, T., et al. Diversity of Intestinal *Clostridium coccoides* Group in the Japanese Population, as Demonstrated by Reverse Transcription-Quantitative PCR. *PLoS One* 10, e0126226 (2015).
25. Donohoe, D. R., et al. The microbiome and butyrate regulate energy metabolism and autophagy in the mammalian colon. *Cell Metab* 13, 517-526 (2011).
26. Byndloss, M. X., et al. Microbiota-activated PPAR-gamma signaling inhibits dysbiotic Enterobacteriaceae expansion. *Science* 357, 570-575 (2017).
27. Donohoe, D. R., Wali, A., Brylawski, B. P. & Bultman, S. J. Microbial regulation of glucose metabolism and cell-cycle progression in mammalian colonocytes. *PLoS One* 7, e46589 (2012).
28. Atarashi, K., et al. Induction of colonic regulatory T cells by indigenous *Clostridium* species. *Science* 331, 337-341 (2011).
29. Atarashi, K., et al. Treg induction by a rationally selected mixture of Clostridia strains from the human microbiota. *Nature* 500, 232-236 (2013).
30. Furusawa, Y., et al. Commensal microbe-derived butyrate induces differentiation of colonic regulatory T cells. *Nature* 504, 446-450 (2013).
31. Yano, J. M., et al. Indigenous bacteria from the gut microbiota regulate host serotonin biosynthesis. *Cell* 161, 264-276 (2015).
32. Kim, Y. G., et al. Neonatal acquisition of Clostridia species protects against colonization by bacterial pathogens. *Science* 356, 315-319 (2017).
33. Noval Rivas, M., et al. A microbiota signature associated with experimental food allergy promotes allergic sensitization and anaphylaxis. *J Allergy Clin Immunol* 131, 201-212 (2013).
34. Caporaso, J. G., et al. Ultra-high-throughput microbial community analysis on the Illumina HiSeq and MiSeq platforms. *ISME J* 6, 1621-1624 (2012).
35. Caporaso, J. G., et al. QIIME allows analysis of high-throughput community sequencing data. *Nat Methods* 7, 335-336 (2010).
36. DeSantis, T. Z., et al. Greengenes, a chimera-checked 16S rRNA gene database and workbench compatible with ARB. *Appl Environ Microbiol* 72, 5069-5072 (2006).
37. Caporaso, J. G., et al. PyNAST: a flexible tool for aligning sequences to a template alignment. *Bioinformatics* 26, 266-267 (2010).
38. Edgar, R. C. Search and clustering orders of magnitude faster than BLAST. *Bioinformatics* 26, 2460-2461 (2010).
39. Oksanen, J., et al. vegan: Community Ecology Package. R package version 2.4.5. (2017).
40. Jiang, L., et al. Discrete False-Discovery Rate Improves Identification of Differentially Abundant Microbes. *mSystems* 2(2017).

41. Segata, N., et al. Metagenomic biomarker discovery and explanation. Genome biology 12, R60 (2011).

42. Bashir, M. E., Louie, S., Shi, H. N. & Nagler-Anderson, C. Toll-like receptor 4 signaling by intestinal microbes influences susceptibility to food allergy. J Immunol 172, 6978-6987 (2004).

43. Nik, A. M. & Carlsson, P. Separation of intact intestinal epithelium from mesenchyme. Biotechniques 55, 42-44 (2013).

44. Andrew, S. FastQC: A quality control application for high throughput sequence data. Babraham Institute Project page: on the world wide web at wwwbioinformaticsbabrahamacuk/projects/fastqc (2016).

45. Bray, N. L., Pimentel, H., Melsted, P. & Pachter, L. Near-optimal probabilistic RNA-seq quantification. Nat Biotechnol 34, 525-527 (2016).

46. Soneson, C., Love, M. I. & Robinson, M. D. Differential analyses for RNA-seq: transcript-level estimates improve gene-level inferences. F1000Res 4, 1521 (2015).

47. Law, C. W., Chen, Y., Shi, W. & Smyth, G. K. voom: Precision weights unlock linear model analysis tools for RNA-seq read counts. Genome biology 15, R29 (2014).

48. Benjamini, Y. & Hochberg, Y. Controlling the False Discovery Rate: a Practical and Powerful Approach to Multiple Testing. J. R. Statist. Soc. B 57, 289-300 (1995).

49. Yu, G., Wang, L. G., Han, Y. & He, Q. Y. clusterProfiler: an R package for comparing biological themes among gene clusters. OMICS 16, 284-287 (2012).

50. Upadhyay, V., et al. Lymphotoxin regulates commensal responses to enable diet-induced obesity. Nat Immunol 13, 947-953 (2012).

51. Liu, X., et al. Warburg effect revisited: an epigenetic link between glycolysis and gastric carcinogenesis. Oncogene 29, 442-450 (2010).

52. Roelen, B. A., Lin, H. Y., Knezevic, V., Freund, E. & Mummery, C. L. Expression of TGF-beta s and their receptors during implantation and organogenesis of the mouse embryo. Dev Biol 166, 716-728 (1994).

53. Ellis, J. M., Bowman, C. E. & Wolfgang, M. J. Metabolic and tissue-specific regulation of acyl-CoA metabolism. PLoS One 10, e0116587 (2015).

54. Al-Dwairi, A., Pabona, J. M., Simmen, R. C. & Simmen, F. A. Cytosolic malic enzyme 1 (ME1) mediates high fat diet-induced adiposity, endocrine profile, and gastrointestinal tract proliferation-associated biomarkers in male mice. PLoS One 7, e46716 (2012).

55. Pinheiro, J. C. & Bates, D. M. Mixed-Effects in Models S and S-Plus, (Springer, New York, 2000).

56. Kuznetsova, A., Brockhoff, P. B., Rune, H. & Christensen, B. lmerTest Package: Tests in Linear Mixed Effects Models. Journal of Statistical Software 82, 1-26 (2017).

57. Moens, F., et al. Lactate- and acetate-based cross-feeding interactions between selected strains of lactobacilli, bifidobacteria and colon bacteria in the presence of inulin-type fructans. Int J Food Microbiol 241: 225-236 (2017).

58. Rettedal, E. A., et al. Cultivation-based multiplex phenotyping of human gut microbiota allows targeted recovery of previously uncultured bacteria. Nat Commun 5: 4714 (2014).

59. Riviere, A., et al. Bifidobacteria and Butyrate-Producing Colon Bacteria: Importance and Strategies for Their Stimulation in the Human Gut. Front Microbiol 7: 979 (2016).

60. Surana, N. K. and D. L. Kasper Moving beyond microbiome-wide associations to causal microbe identification. Nature 552(7684): 244-247 (2017).

61. Torii, T., et al. Measurement of short-chain fatty acids in human faeces using high-performance liquid chromatography: specimen stability. Ann Clin Biochem 47(5): 447-452 (2010).

62. Tyagi, A. M., et al. The Microbial Metabolite Butyrate Stimulates Bone Formation via T Regulatory Cell-Mediated Regulation of WNT10B Expression. Immunity 49(6): 1116-1131 e1117 (2018).

The invention claimed is:

1. A method for increasing butyrate production in a subject in a state of dysbiosis, the method consisting of administering a composition consisting of *Anaerostipes caccae* and potato starch to the subject.

2. The method of claim 1 wherein the subject has an atopic disease selected from the group consisting of eczema, atopic dermatitis, asthma, and allergic rhinitis.

3. The method of claim 1, wherein at least 3 grams of potato starch is administered to the subject.

4. The method of claim 1, wherein the subject has a food allergy selected from the group consisting of a cow's milk allergy, egg allergy, peanut allergy, soy allergy, wheat/gluten allergy, shellfish allergy, sesame allergy, and tree nut allergy.

5. The method of claim 1, wherein the subject is a human.

6. The method of claim 5, wherein the subject is less than one year old, less than five years old, less than twelve years old or less than eighteen years old.

7. The method of claim 1, wherein the *A. caccae* and potato starch are administered orally.

8. A method for increasing butyrate production in a subject in a state of dysbiosis, the method consisting of administering a composition consisting of *Anaerostipes caccae*, lactate, and acetate to the subject.

9. The method of claim 8 wherein the subject has an atopic disease selected from the group consisting of eczema, atopic dermatitis, asthma, and allergic rhinitis.

10. The method of claim 8, wherein the subject has a food allergy selected from the group consisting of a cow's milk allergy, egg allergy, peanut allergy, soy allergy, wheat/gluten allergy, shellfish allergy, sesame allergy, and tree nut allergy.

11. The method of claim 8, wherein the subject is a human.

12. The method of claim 11, wherein the subject is less than one year old, less than five years old, less than twelve years old or less than eighteen years old.

13. The method of claim 8, wherein the composition is administered orally.

* * * * *

SEQUENCE LISTING

```
<160> NUMBER OF SEQ ID NOS: 14

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gttttcggat ggatttccta tat                                              23

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cttttcacac tgaatcatgc gatt                                             24
```

-continued

```
<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgaagagcta ctgtaatgat cagtcaac                                        28

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agcaagcttg caaccttaac ca                                              22

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccatcataat cgaacctgag                                                 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cttctcagaa ggctcatcag                                                 20

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccggtgtgaa ctgtcaccga tc                                              22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cctgatgaaa actggaccac ag                                              22

<210> SEQ ID NO 9
```

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atcgacacct tgggacaacc                                                         20

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agtgcaggat tgccgtctg                                                          19

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccgtggcact aaggtcagtt                                                         20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acgttacggt gcacgaattg                                                         20

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agtatccatg aacaaagggc ac                                                      22

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atcccattac agccaaggtc                                                         20
```